(12) United States Patent
Tanaka et al.

(10) Patent No.: US 9,365,836 B2
(45) Date of Patent: Jun. 14, 2016

(54) GLYCOSYLTRANSFERASE GENE AND USE THEREOF

(75) Inventors: Yoshikazu Tanaka, Osaka (JP); Naoko Okitsu, Osaka (JP); Keisuke Matsui, Osaka (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 161 days.

(21) Appl. No.: 13/979,717

(22) PCT Filed: Jan. 11, 2012

(86) PCT No.: PCT/JP2012/050379
§ 371 (c)(1),
(2), (4) Date: Jul. 15, 2013

(87) PCT Pub. No.: WO2012/096307
PCT Pub. Date: Jul. 19, 2012

(65) Prior Publication Data
US 2014/0033369 A1    Jan. 30, 2014

(30) Foreign Application Priority Data

Jan. 14, 2011    (JP) .................................. 2011-006317

(51) Int. Cl.
| | | |
|---|---|---|
| C12N 9/10 | (2006.01) | |
| C12N 15/82 | (2006.01) | |
| C07H 17/07 | (2006.01) | |
| C12P 19/18 | (2006.01) | |
| A23L 1/305 | (2006.01) | |
| A61K 8/60 | (2006.01) | |
| A61Q 19/00 | (2006.01) | |
| C12P 19/46 | (2006.01) | |
| C12P 19/60 | (2006.01) | |

(52) U.S. Cl.
CPC .............. *C12N 9/1048* (2013.01); *A23L 1/3053* (2013.01); *A61K 8/606* (2013.01); *A61Q 19/00* (2013.01); *C07H 17/07* (2013.01); *C12N 15/8245* (2013.01); *C12P 19/18* (2013.01); *C12P 19/46* (2013.01); *C12P 19/60* (2013.01); *C12P 19/605* (2013.01); *Y02P 20/52* (2015.11)

(58) Field of Classification Search
None
See application file for complete search history.

(56) References Cited

U.S. PATENT DOCUMENTS

| 6,596,927 B1 * | 7/2003 | Mizutani et al. ...... C12N 9/0077 435/320.1 |
| 2011/0030090 A1 | 2/2011 | Falco et al. | |

FOREIGN PATENT DOCUMENTS

| EP | 0967283 A1 | 12/1999 |
| EP | 1291418 A1 | 3/2003 |
| EP | 1652916 A1 | 5/2006 |
| EP | 1985704 A1 | 10/2008 |
| EP | 2159283 A1 | 3/2010 |
| EP | 2423312 A1 | 2/2012 |
| JP | 2005-095005 A | 4/2005 |
| JP | 2005-519940 A | 7/2005 |
| JP | 2006-149293 A | 6/2006 |
| WO | WO-99/05287 A1 | 2/1999 |
| WO | WO-01/92509 A1 | 12/2001 |
| WO | WO-03075685 A2 | 9/2003 |
| WO | WO-2005017147 A1 | 2/2005 |
| WO | WO-2006/105598 A1 | 10/2006 |
| WO | WO-2007094521 A1 | 8/2007 |
| WO | WO-2008156211 A1 | 12/2008 |
| WO | WO-2009/062253 A1 | 5/2009 |
| WO | WO-2010/122849 A1 | 10/2010 |

OTHER PUBLICATIONS

Hong et al., 2007, Journal of Biochemistry and Molecular Biology 40: 870-874.*
GenBank/NCBI Sequence With Accession No. XM_002887467.1/ XP_002887513.1, UDP-glucoronosyl/UDP-glucosyl transferase family protein [*Arabidopsis lyrata* subsp. *lyrata*], published Jun. 11, 2010.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Maniatis et al., 1982, Molecular Cloning: A Laboratory Manual, Cold Spring Harbor Laboratory, pp. 324-343 and 387-389.*
Yoshida et al., 2009, Natural Products Reports 26: 857-964.*

(Continued)

*Primary Examiner* — David T Fox
*Assistant Examiner* — Bratislav Stankovic
(74) *Attorney, Agent, or Firm* — Drinker Biddle & Reath LLP

(57) ABSTRACT

Provided is a polynucleotide encoding a protein having an activity to transfer a sugar to the hydroxy groups at the 4'- and 7-positions of a flavone. The polynucleotide is selected from the group consisting of: (a) a polynucleotide which comprises a base sequence represented by SEQ ID NO: 1, 3, or 12; (b) a polynucleotide which hybridizes to a polynucleotide comprising a base sequence complementary to a base sequence represented by SEQ ID NO: 1, 3, or 12 under high stringency conditions, and encodes a protein having an activity to transfer a sugar to the hydroxy groups at the 4'- and 7-positions of a flavone; (c) a polynucleotide which encodes a protein comprising an amino acid sequence represented by SEQ ID NO: 2, 4, or 13; (d) a polynucleotide which encodes a protein comprising an amino acid sequence in which one or more amino acids have been deleted, substituted, inserted, and/or added in an amino acid sequence represented by SEQ ID NO: 2, 4, or 13 and having an activity to transfer a sugar to the hydroxy groups at the 4'- and 7-positions of a flavone; etc.

5 Claims, 22 Drawing Sheets

(56) References Cited

OTHER PUBLICATIONS

Matsuba et al., 2010, The Plant Cell 22: 3374-3389.*
Yuki Matsuba, et al., "A Novel Glucosylation Reaction on Anthocyanins Catalyzed by Acyl-Glucose-Dependent Glucosyltransferase in the Petals of Carnation and Delphinium☒☒," The Plant Cell, vol. 22, Oct. 2010, pp. 3374-3389.
Akio Noguchi, et al., "Local Differentiation of Sugar Donor Specificity of Flavonoid Glycosyltransferase in Lamiales☒," The Plant Cell, vol. 21, May 2009, pp. 1556-1572.
S. Süzgeç-Selçuk, et al., "Flavonoids of *Helichrysum chasmolycicum* and its antioxidant and antimicrobial activities," South African Journal of Botany, 77, 2011, pp. 170-174.
Nigel C. Veitch, et al., "Flavonoid Cellobiosides From *Salvia uliginosa*," Plytochemistry, vol. 48, No. 2, 1998, pp. 389-393.
International Search Report with a mailing date of Mar. 6, 2012 in PCT/JP2012/050379 filed Jan. 11, 2011.
Supplementary European Search Report mailed Aug. 7, 2014 in European Application No. 12734422.4.
Database UniProt [Online] Mar. 24, 2009; "SubName: Full=UDP-glycosyltransferase, putative; EC-2.4.1.115;" XP-002727681; retrieved from EBI accession No. UNIPROT:B9RLH5; Database accession No. B94LH5.
Database UniProt [Online] May 1, 1997; "SubName: Full=Immediate-early salicylate-induced glucosyltransferase;" XP-002727682; retrieved from EBI accession No. UNIPROT: Unreviewed; Database accession No. P93365.
Database UniProt [Online] Jul. 1, 2008; "SubName: Full=UGT73A13;" XP-002727683; retrieved from EBI accession No. UNIPROT:B2NID6; Database accession No. B2NID6.
Database Geneseq [Online] Jun. 8, 1998; "Glucosyl transferase (GTase) encoding wound inducible gene (TWI1);" XP-002727684; retrieved from EBI accession No. GSN:AAV17054; Database accession No. AAV17054.
Database EMBL [Online] May 8, 2008; "Perilla frutescens PfUgT31 mRNA for UGT73A13, complete cds." XP-002727685; retrieved from EBI accession No. EM_STD:AB362995; Database accession No. AB362995.
Hirotani, et al., "Cloning and Expression of UDP-glucose: flavonoid 7-O-glucosyltransferase from hairy root cultures of *Scutellaria baicalensis*", Planta, 2000, 210, pp. 1006-1013.
Katsumoto, et al., "Engineering of the Rose Flavonoid Biosynthetic Pathway Successfully Generated Blue-Hued Flowers Accumulating Delphinidin", Plant Cell Physiol., 2007, 48(11): pp. 1589-1600.
Kim, et al., "Characterization of 7-O-glucosyltransferase from *Arabidopsis thaliana*", Biosci. Biotechnol. Biochem., 2006, 70(6), pp. 1471-1477.
Matsuba, et al., "A Novel Glucosylation Reaction on Anthocyanins Catalyzed by Acyl-Glucose-Dependent Glucosyltransferase in Petals of Carnation and Delphinium", The Plant Cell, Oct. 2010, vol. 22, pp. 3374-3389.
Nakasuka, et al., "Cloning and Characterization of the UDP-glucose:anthocyanin 5-O-glucosyltransferase gene from blue-flowered gentian", Journal of Experimental Botany, 2008, vol. 59, No. 6, pp. 1241-1252.
Tanaka, et al., "Molecular and Biochemical Characterization of Three Anthocyanin Synthetic Enzymes from *Gentiana triflora*", Plant Cell Physiol. 1996, 37(5), pp. 711-716.
Tanaka, et al., "Flower Color Modification by Engineering of the Flavonoid Biosynthetic Pathway: Practical Perspectives", Biosci. Biotechnol. Biochem., 2010, 74(9), pp. 1760-1769.
Vogt, et al., Cloning and expression of a cDNA encoding betanidin 5-O-glucosyltransferase, a betanidin- and flavonoid-specific enzyme with high homology to inducible glucosyltransferase from the Solanaceae, The Plant Journal, 1999, 19(5), pp. 509-519.
Yamazaki, et al., "Molecular Cloning and Biochemical Characterization of a Novel Anthocyanin 5-O-glycosyltransferase by mRNA Differential Display for Plant Forms Regarding Anthocyanin", The Journal of Biological Chemistry, Mar. 12, 1999, vol. 274, No. 11, pp. 7405-7411.
Yamazaki, et al., "Two flavonoid glucosyltransferase from *Petuni hybrida*: molecular cloning, biochemical properties and developmentally regulated expression", Plant Molecular Biology, 2002, 48, pp. 401-411.
Yoshida, et al., "Blue flower color development by anthocyanisn: from chemical structure to cell physiology", Nat. Prod. Rep., 2009, 26, pp. 884-915.
Office Action issued Jan. 28, 2016 in European Patent Application No. 12 734 422.4.

* cited by examiner

Fig.13

| | NmGT3 | NmGT4 | SuGTAK5 | betanidin5GT |
|---|---|---|---|---|
| Api | ◎(Api4'Glc,Api7Glc,Api4'7Glc) | ◎(Api4'Glc,Api7Glc,Api4'7Glc) | ◎(Api4'Glc,Api4'7Glc) | (×) |
| Api7Glc | △(Api4'7Glc) | △(Api4'7Glc) | △(Api4'7Glc) | |
| Lut | ◎(Lut4'Glc,Lut7Glc,Lut4'7Glc) | ◎(Lut4'Glc,Lut7Glc,Lut4'7Glc) | ◎(Lut4'Glc,Lut4'7Glc) | △(Lut4'Glc,Lut7Glc) |
| Lut7Glc | △(Lut4'7Glc) | △(Lut4'7Glc) | △(Lut4'7Glc) | |
| Lut4'Glc | ◎(Lut4'7Glc) | ◎(Lut4'7Glc) | ◎(Lut4'7Glc) | |
| Tri | ◯ | ◯ | ◯ | |
| K | ◎(K3Glc) | ◎(K3Glc) | ◎(K3Glc) | (×)(K4'Glc) |
| K3Glc | ◯ | ◯ | ◯ | |
| Q | ◎(Q3Glc) | ◎(Q3Glc) | ◎(Q3Glc) | ◯(Q4'Glc,Q7Glc) |
| Q3Glc | ◎ | ◎ | ◯ | |
| M | | ◎ | △ | △(M4'Glc,M7Glc) |
| Narigenin | △ | △ | | |
| betanidin | ◯ | ◯ | × | ◯(betanidin5Glc) |

↑ From data in an article
(Thomas Vogt, 1997, 1999)

( ): Biosynthetic reaction product
Api4'Glc : Apigenin 4'-glucoside
Api7Glc : Apigenin 7-glucoside
Api4',7Glc : Apigenin 4',7-diglucoside
Lut4'Glc : Luteonin 4'-glucoside
Lut7Glc : Luteonin 7-glucoside
Lut4',7Glc : Luteonin 4',7-diglucoside
K3Glc : Kaempferol 3-glucoside
K4'Glc : Kaempferol 4'-glucoside
Q3Glc : Quercetin 3-glucoside
Q4'Glc : Quercetin 4'-glucoside
Q7Glc : Quercetin 7-glucoside
M4'Glc : Myricetin 4'-glucoside
M7Glc : Myricetin 7-glucoside
betanidin5Glc : Betanidin 5-glucoside Degree of enzyme reaction
◎ : So vigorous as to use up the substrate
◯ : Reactive
△ : Reactive, but few products
× : Completely nonreactive
(×) : Hardly reactive

Fig. 14

```
NmGT4    1   ----MAAQLHVVFFPFMAAQGHLIPTLEMVKLFSSRGLKTTIVTTKFYAPAVT
NmGT3    1   MPSILSNSAHILLFPFPTSGHIIPILDLANQLLARGLTILITPANLTLLS

NmGT4   97   KSIEKTKHTGNQINIIIKFPSAEVGLPEGSESLDKLKSPDMFMKFFFK       96
NmGT3   88   TQLIELDRLG-SLHTLVLPFPNPPN----------PSETSLAARVH        87

ALSLLQEPFFEQILQELS--PDCIVSDMFFPWTTASAAKFDIPRFVFHGLSL
             ASSQLSNTIIQWFQSHTSPPVAIVSDFFLGWTNSLASQLGIPRLVFWPSGV  194
                                                                   187

FALCVSENMRFYKPFKNLGSESLDSEPVMLPDFPNQIEFSKVQVPEFEV
             QRSSLVDYIWQNDQLSDSDHQIQDNSVISFPDVPNSPAYPKWQACGLST

NmGT4  195   GESKNE-IMELLNQVKESEVKSYGIINSFNELEKDYVDYYRNVWGR-
NmGT3  188   QYKKGDPSWEFFKNGVLANTQSWGAIYNSFRDLEGVYIDYIKKKMGHG

RAWLLGPLSLSNRDDE--VKDQTDEHGSLKWLDSKK--PDSVIYVCFGSVAP  288
             RVWAVGPLLPANDASKRGGSCVMPIDDVMTWLDTKTNSDNSVVYVCFGSRVE 287

NmGT4  289   LSSSQLHEIALGLESSGQQFIWVVKEREDGEKWLPEGFEEERIKDKGLIIRGWAPQV
NmGT3  288   LTTEQLDSLAAALEISGVHFILCVKLHQEIS---KEYEDRVAGRGLIIRGWAPQV

SILEHESTGGFVTHCGWNSVLEAVSAGVVMATLPTFAEQPFNEK      388
             AILRHRAVGAFLTHCGWNSILEGIAAGVVMLTWPMGADQFTNAN      383

NmGT4  389   LLTKVLKIGIPIG-SPLSNRGKSGVKKEEIAEAMKGIMEGEEALEMR
NmGT3  384   LLVDELKVAMKACEGGDSNVPNPAMLANVLAESINGGRAE----R

IRAKSLKEMAWKAVEEG-GSSYNDLTSLIDGVKAYRSQSNKI    475
             ERVTELCDAALKAVQSGNGSSAKDLDSLTNQLNGLKVKIN--    464
```

Fig. 15

```
Dianthus_caryophyllus-chalcononaringenin_2'-GT    1 -MGSEHQQLHVAFFPPFMAHGHMIPTFDLAKLFAGRDVKTTIITTPMNAHAFA
NmGT3                                             1 MPSILSNSAHILLFPFPTSGHIPIDLANQLLARGLTITILITPANLTLLS     95
                                                                                                                 90

Dianthus_caryophyllus-chalcononaringenin_2'-GT   96 KTNVPMN---LEIFTFPAQEAGLPENCENLEQAMSIGLLPAFIKASA
NmGT3                                            91 TQLLELDRLGSLHTLVLPFPNPPNPSETS--------LAARVHAS S    188
                                                                                                               190

Dianthus_caryophyllus-chalcononaringenin_2'-GT  189 MLCDQLERFLE-RSQPNCLVADMFFPWATESARKFNVPRIVFHGTGFLSLC
NmGT3                                           191 QLSNTIIQWFQSHTSPPVAIVSDFFLGWTNSLASQLGIPRLVFWPSGVQRSS AKEVERLYRPFKN---VSSDEVVLPRLPHEVKLTRTQVS--EEEWS
                                                    LVDYIWQNDQLSDSDHQIQDNSVISFPDVPNSPAYPKWQACGLSTQYK Dianthus_caryophyllus-chalcononaringenin_2'-GT  286 DDDNEFNKRSARIKESEVESYGVIVNSFYELEPEFADFFRNELGR-RAWNVGPV
NmGT3                                           286 KGDPSWEFFKNGVLAN-TQSWGAIYNSFRDLEGVYIDYIKKKMGHGRVWAVGPL    285
                                                                                                                  285

SLCNRKTEDKARRGKQANVNEQECLIWLDSKK--CASVVYVCFGST
                                                    LPAN---DASKRGGSCVMPIDDVMTWLDTKTNSDNSVVYVCFGSR

Dianthus_caryophyllus-chalcononaringenin_2'-GT  386 AHYAPAQLHEIANALEASGHNFVWAVGNVDKGSDGEELLPQGFEQRTE
NmGT3                                           286 VELTTEQLDSLAAALEISGVHFILCVKLHQEIS-----KEYEDRVA GRGLIIRGWAPQVLILEHEAVGAFMTHCGWNSTLEGISAGVPMVTWPVFAEQ    385
                                                    GRGLIIRGWAPQVAILRHRAVGAFLTHCGWNSILEGIAAGVMLTWPMGADQ    378

Dianthus_caryophyllus-chalcononaringenin_2'-GT  386 FYNEKLVTQILKIRVEVGAKKWSRTAMIEHKISGDATEKALKEIMEGE
NmGT3                                           379 FTNANLLVDELKVAMKACEGGDS---NVPNPAMLANVLAESINGG KAEEMRNKIARQLKEMAWKAVEEG-GSSYNDLTALISELRNYKA---    475
                                                    RAERERR--VTELLCDAALKAVQSGNGSSAKDLDSLLTNQLNGLKVKIN     464
```

Fig.16

```
Scutellaria_barbata-flavonoid-7GT    1 - M G Q L H I V L V P M I A H G H M I P M L D M A K L F S S R G V K T T I I A T - - - P A F A E P I R
NmGT4                                1 M A Q L H V V F F P F M A Q G H L I P T L E M V K L F S S R G L K T T I V T T K F Y A P A V T K S L E Scutellaria_barbata-flavonoid-7GT   95 K A R E S G H D I G L T T T K F P P K G S S L P D N I R S L D Q V T D - D L L P H F F R A L E L  94
NmGT4                              101 K T K H T G N Q I N I I I K F P P S A E V G L P E G S E S L D K L K S P D M F M K F F K A L S L 100

Scutellaria_barbata-flavonoid-7GT      L Q E P V E E I M E D L K P D C L V S D M F L P W T T D S A A K F G I P R L L F H G T S L F A R C F A
NmGT4                                  L Q E P F E Q I L Q E L S P D C I V S D M F F P W T T A S A A K F D I P R F V F H G L S L F A L C V S Scutellaria_barbata-flavonoid-7GT      E Q M S I Q K P Y K N V S S - - D S E P F V L R G L P H E V S F V R T Q I P D Y E L Q E G G D D  191
NmGT4                                  E N M R F Y K P F K N L G S E S L D S E P V M L P D F P N Q I E F S K V Q V P E F E V G E S - K N  199

Scutellaria_barbata-flavonoid-7GT  192 A F S K M A K Q M R D A D K K S Y G D V I N S F E E L E S E Y A D Y N K N V F G K K A W H I G P L K L
NmGT4                              200 E I M E L L N Q V K E S E V K S Y G I I I N S F N E L E K D Y V D Y R N V W G R R A W L L G P L S L Scutellaria_barbata-flavonoid-7GT      F N N R A E Q K S S Q R G K E S A I D D H E C L A W L N S K K P N S V V Y M C F G S M A T F T P A  291
NmGT4                                  S N R D D E V K D Q T - - - - - D E H G S L K W L D S K K P D S V I Y V C F G S V A P L S S  292

Scutellaria_barbata-flavonoid-7GT  292 Q L H E T A V G L E S S G Q D F I W V V R N G G E N E D W L P Q G F E E E R I K G K G L M I R G W A P Q V
NmGT4                              293 Q L H E I A L G L E S S G Q Q F I W V V K E R E D G E K W L P E G F E E R I K D K G L I I R G W A P Q V Scutellaria_barbata-flavonoid-7GT  392 M I L D H P S T G A F V T H C G W N S T L E G I C A G L P M V T W P V F A E Q F Y N E K L V T E  391
NmGT4                              393 S I L E H E S T G G F V T H C G W N S V L E A V S A G V M A T L P T F A E Q P F N E K L L T K  392

Scutellaria_barbata-flavonoid-7GT      V L K T G V S V G N K K W Q R V G E G V G S E A V K E A V E R V M V G D G A A A E M R S R A L Y Y K E M A
NmGT4                                  V L K I G I P I G S P L S N R G K S G V K K E E I A E A M K G I M E G E E A L E M R I R A K S L K E M A Scutellaria_barbata-flavonoid-7GT      R K A V E E G G S S Y N L N A L I E E L S A Y V P P M K Q G L N  476
NmGT4                                  W K A V E E G G S S Y N D L T S L I D G V K A Y R S Q S N K I - -  475
```

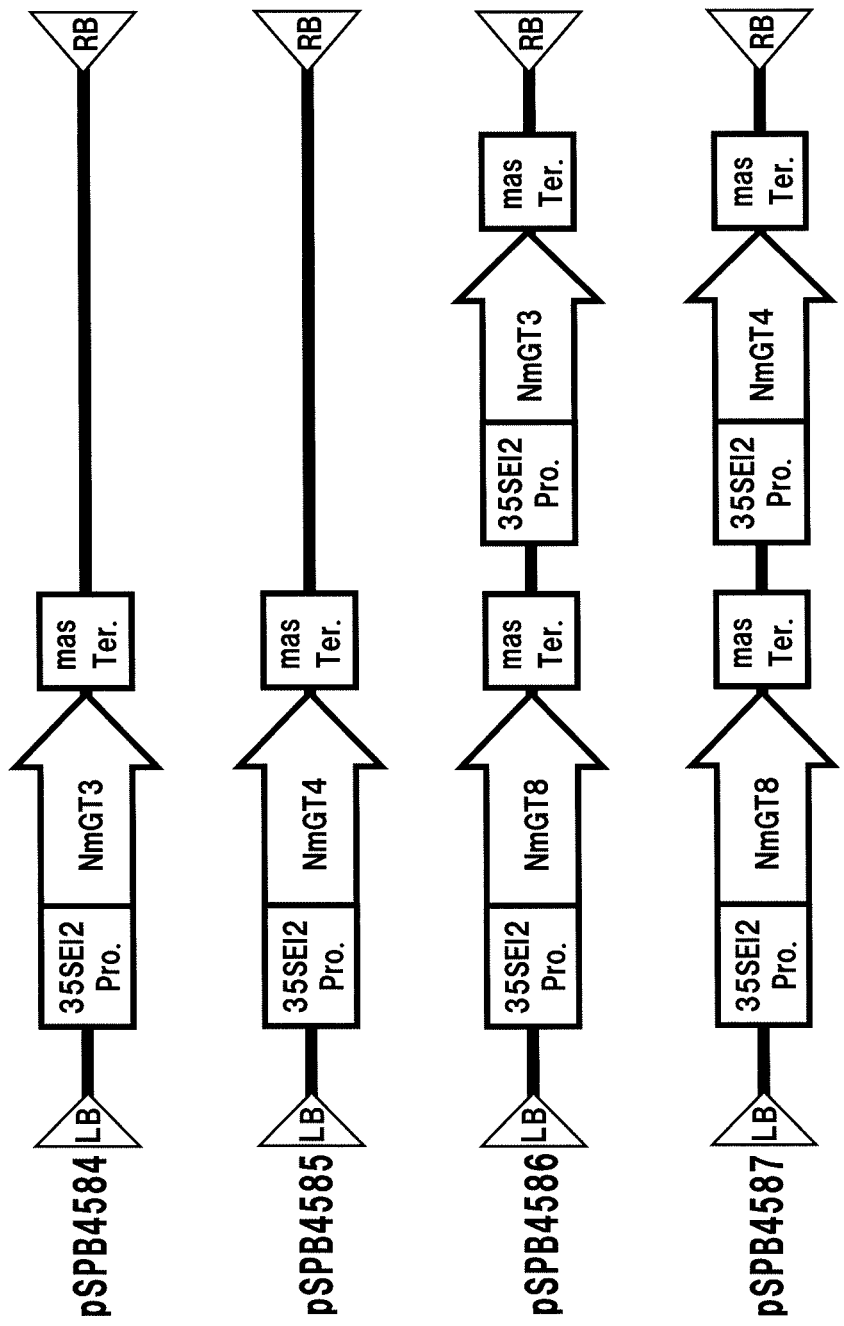

Fig. 23

```
SuGTAK5    1   - - - - - M K Q L H I A L F P S M A H G H M I P M F E L A K L F T S R G L K A T I I A T P A F A A P I
NmGT3      1   M P S I L S N S A H I L L F P F P T S G H I L P I L D L A N Q L L A R G L T I T I L I T P A N L T L L      92
               T K A Q Q S G L D V G - - L A I T P F P P K G S S L P Q N I I A F D Q M T N P D L T T S F L R A           92
               S T Q L I E L D R L G S L H T L V L P F P - N P P N P S E T S L A A R V H A S S Q L S N T I I Q W         99

SuGTAK5    93  M E L L Q E P V E A I L Q E L H P D C L V S D M F L P W T A D S A A K F Q I P R L A F Y G T S Y F S R
NmGT3     100  F Q S H T S P - - - - - - P V A I V S D F F L G W T N S L A S Q L G I P R L V F W P S G V Q R S          188
               C V S E Q V G D K P - - - - F N N V T S D S E P V L V P G L P Q Q I K F V R S Q F S P V L L E E T          188
               S L V D Y I W Q N D Q L S D S D H Q I Q D N S V I S F P D V P N S P A Y P K W Q A C G L S T Q Y K         190

SuGTAK5   189  Q N D - F A K L F K Q M T E A W K K T Y G E V V N S F N E L E S D Y A N H Y K N V I G R - K A W E I
NmGT3     191  K G D P S W E F F K N G V L A N T Q S W G A I Y N S F R D L E G V Y I D Y I K K K M G H G R V W A V
               G P L L C S S S K G G E K N Q Q R G K E S A I D E H E C L A W L D S K N - - P N S V V Y V C A G S         284
               G P L L P A N D A S - - - - - K R G G S C V M P I D D V M T W L D T K T N S D N S V V Y V C F G S         284

SuGTAK5   285  V A S F S Q A Q L R E T A M G L E A S G Q N F V W V R K N K E D D D D W L P V G F E E R V G N
NmGT3     285  R V E L T T E Q L D S L A A L E I S G V H F I L C V K L H Q E I S - - - - - K E Y E D R V A G
               R G L I I R G W A P Q V M I L N H A A V G A F V T H C G W N S T L E G V C A G L P M V T W P V F A E Q F     384
               R G L I I R G W A P Q V A I L R H R A V G A F L T H C G W N S I L E G I A A G V M L T W P M G A D Q F       379

SuGTAK5   385  F N E K L V T E V L G T G V S V G N K R W M L R E S E G V E R D A V A R A V E E I M V G G G A E E
NmGT3     380  T N A N L L V D E L K V A M K A C E G - - - G D S N V P N P A M L A N V L A E S I N G G R A E R
               M R S R A E N Y K E M A K K A V E E G - G S S Y N N L N A L I E E L S N Y V A P T I Q D K N - - - -        478
               E - - R V T E L C D A A L K A V Q S G N G S S A K D L D S L T N Q L N G L K V K I N - - - -                464
```

Fig. 24

```
SuGTAK5    1   -MKQLHIALFPSMAHGHMIPMFELAKLFTSRGLKATIIAT---PAFAAPIT      95
NmGT4      1   MAAQLHVVFFPFMAQGHLIPTLEMVKLFSSRGLKTTTIVTTKFYAPAVTKSL    100
               TKAQQSGLDVGLATPFPPKGSSLPQNIIAFDQMTNPDLTTSFLRAMEL
               EKTKHTGNQINIIIKFPSAEVGLPEGSESLDKLKSPDMFMKFFKALSL

SuGTAK5    96  LQEPVEAILQELHPDCLVSDMFLPWTADSAAKFQIPRLAFYGTSYFSRCVSE    191
NmGT4     101  LQEPFEQILQELSPDCIVSDMFFPWTASAAKFDIPRFVFHGLSLFALCVSE    200
               QVG-DKPFNNVTS---DSEPVLVPGLPDFPPNQIKFVRSQFSPVLLEETQND
               NMRFYKPFKNLGSESLDSEPVMLPDFPPNQIEFSKVQVPEFEVGESKNE

SuGTAK5   192  FAKLFKQMTEAWKKTYGEVVNSFNELESDYANHYKNVIGRKAWEIGPLLLC    291
NmGT4     201  IMELLNQVKESEVKSYGIIINSFNELEKDYVDYYRNVWGRRAWLLGPLSLS    292
               SSSKGGEKNQQRGKESAIDEHECLAWLDSKNPNSVVYVCAGSVASFSQA
               ----NRDDEVKDQTDEHGSLKWLDSKKPDSVIYVCFGSVAPLSSS

SuGTAK5   292  QLRETAMGLEASGQNFVWVVRKNKEDDDDWLPVGFEERVGNRGLIIRGWAPQV    391
NmGT4     293  QLHEIALGLESSGQQFIWVVKE-REDGEKWLPEGFEERIKDKGLIIRGWAPQV    391
               MILNHAAVGAFVTHCGWNSTLEGVCAGLPMVTWPVFAEQFFNEKLVT
               SILEHESTGGFVTHCGWNSVLEAVSAGVVMATLPTFAEQPFNEKLLT

SuGTAK5   392  EVLGTGVSVGNKRWMLRESEGVERDAVARAVEEIMVGGGAEEMRSRAENY    478
NmGT4     392  KVLKIGIPIGSP-LSNRGKSGVKKEEIAEAMKGIMEGEEALEMRIRAKSL    475
               KEMAKKAVEEGGSSYNLNALIEELSNYVAPTIQDKN--
               KEMAWKAVEEGGSSYNDLTSLIDGVKAYRSQSNKI
```

US 9,365,836 B2

SEQUENCE LISTING

```
<160> NUMBER OF SEQ ID NOS: 15

<210> SEQ ID NO 1
<211> LENGTH: 1395
<212> TYPE: DNA
<213> ORGANISM: Nemophila menziesii
<220> FEATURE:
<223> OTHER INFORMATION: NmGT3
<220> FEATURE:
<221> NAME/KEY: CDS
<222> LOCATION: (1)..(1392)

<400> SEQUENCE: 1 atg cca tca atc ctg agc aat agc gca cac att cta ctc ttt cca ttt        48
Met Pro Ser Ile Leu Ser Asn Ser Ala His Ile Leu Leu Phe Pro Phe
1               5                   10                  15 cct act tca gga cat att ata ccc atc ctt gat ctt gcc aac caa tta        96
Pro Thr Ser Gly His Ile Ile Pro Ile Leu Asp Leu Ala Asn Gln Leu
                20                  25                  30 ctt gcc cgt ggc tta acc atc acc atc tta atc aca ccc gca aac cta       144
Leu Ala Arg Gly Leu Thr Ile Thr Ile Leu Ile Thr Pro Ala Asn Leu
            35                  40                  45 act ctt ctc tcc aca cag ttg ata gag ctc gac cgt ctt ggt tcc cta       192
Thr Leu Leu Ser Thr Gln Leu Ile Glu Leu Asp Arg Leu Gly Ser Leu
        50                  55                  60 cat act ttg gtc ctt cct ttt cca aac ccc ccc aac cct tca gag act       240
His Thr Leu Val Leu Pro Phe Pro Asn Pro Pro Asn Pro Ser Glu Thr
65                  70                  75                  80 agt ttg gct gca aga gtt cat gct agt agt caa cta tca aac acc atc       288
Ser Leu Ala Ala Arg Val His Ala Ser Ser Gln Leu Ser Asn Thr Ile
                85                  90                  95 ata caa tgg ttc caa tct cac aca tca ccc cct gtt gcc att gtt tct       336
Ile Gln Trp Phe Gln Ser His Thr Ser Pro Pro Val Ala Ile Val Ser
            100                 105                 110 gat ttt ttc ctt ggc tgg act aac agc tta gca tca caa ttg gga atc       384
Asp Phe Phe Leu Gly Trp Thr Asn Ser Leu Ala Ser Gln Leu Gly Ile
        115                 120                 125 ccg cgt ctt gta ttt tgg cca tcg ggt gtt caa cga tct tcg ctc gta       432
Pro Arg Leu Val Phe Trp Pro Ser Gly Val Gln Arg Ser Ser Leu Val
    130                 135                 140 gat tat ata tgg caa aat gat caa ttg tca gat tcc gac cac caa atc       480
Asp Tyr Ile Trp Gln Asn Asp Gln Leu Ser Asp Ser Asp His Gln Ile
145                 150                 155                 160 caa gac aat tct gtg att tca ttt cct gat gta ccg aac tca cca gca       528
Gln Asp Asn Ser Val Ile Ser Phe Pro Asp Val Pro Asn Ser Pro Ala
                165                 170                 175 tac cca aag tgg caa gcc tgt ggt ctt agt act cag tat aag aaa gga       576
Tyr Pro Lys Trp Gln Ala Cys Gly Leu Ser Thr Gln Tyr Lys Lys Gly
            180                 185                 190 gac cca agc tgg gaa ttt ttc aag aat ggt gtt tta gca aat aca caa       624
Asp Pro Ser Trp Glu Phe Phe Lys Asn Gly Val Leu Ala Asn Thr Gln
        195                 200                 205 agc tgg ggt gct atc tat aat tct ttt agg gac tta gaa gga gtt tat       672
Ser Trp Gly Ala Ile Tyr Asn Ser Phe Arg Asp Leu Glu Gly Val Tyr
    210                 215                 220 att gat tat atc aag aag aaa atg ggc cat gga aga gtt tgg gca gtt       720
```

```
                Ile Asp Tyr Ile Lys Lys Met Gly His Gly Arg Val Trp Ala Val
                225                 230                 235                 240 ggg cca ctt ttg ccc gca aat gat gca tca aaa cgc ggt gga tca tgt           768
Gly Pro Leu Leu Pro Ala Asn Asp Ala Ser Lys Arg Gly Gly Ser Cys
                    245                 250                 255 gta atg ccc att gat gat gta atg aca tgg tta gat acg aaa acc aat           816
Val Met Pro Ile Asp Asp Val Met Thr Trp Leu Asp Thr Lys Thr Asn
                    260                 265                 270 tca gac aat tct gtt gtt tat gtc tgt ttt ggt agt cga gta gag tta           864
Ser Asp Asn Ser Val Val Tyr Val Cys Phe Gly Ser Arg Val Glu Leu
                    275                 280                 285 aca acc gag caa cta gat tct tta gca gct gca ctt gaa atc agt ggg           912
Thr Thr Glu Gln Leu Asp Ser Leu Ala Ala Ala Leu Glu Ile Ser Gly
                    290                 295                 300 gtt cat ttc ata ttg tgt gtg aag tta cat cag gag atc tca aag gag           960
Val His Phe Ile Leu Cys Val Lys Leu His Gln Glu Ile Ser Lys Glu
305                 310                 315                 320 tac gaa gat cga gtg gct gga aga gga ttg atc ata agg gga tgg gca          1008
Tyr Glu Asp Arg Val Ala Gly Arg Gly Leu Ile Ile Arg Gly Trp Ala
                    325                 330                 335 cca caa gtc gcg ata tta agg cat cga gct gtg ggt gcg ttt ttg act          1056
Pro Gln Val Ala Ile Leu Arg His Arg Ala Val Gly Ala Phe Leu Thr
                    340                 345                 350 cat tgt ggg tgg aat tcc ata tta gaa gga ata gct gcg ggt gtg gtg          1104
His Cys Gly Trp Asn Ser Ile Leu Glu Gly Ile Ala Ala Gly Val Val
                    355                 360                 365 atg cta aca tgg cca atg ggt gct gat caa ttt acg aat gct aac tta          1152
Met Leu Thr Trp Pro Met Gly Ala Asp Gln Phe Thr Asn Ala Asn Leu
370                 375                 380 tta gta gat gag tta aag gtg gcg atg aag gct tgt gaa ggc ggt gat          1200
Leu Val Asp Glu Leu Lys Val Ala Met Lys Ala Cys Glu Gly Gly Asp
385                 390                 395                 400 agt aac gtg ccc aac cct gcc atg ttg gct aat gta tta gcc gag tca          1248
Ser Asn Val Pro Asn Pro Ala Met Leu Ala Asn Val Leu Ala Glu Ser
                    405                 410                 415 ata aat ggt ggt agg gct gag agg gag aga gtg acg gag ctg tgt gat          1296
Ile Asn Gly Gly Arg Ala Glu Arg Glu Arg Val Thr Glu Leu Cys Asp
                    420                 425                 430 gct gcc ttg aag gct gtt cag agt gga aac ggt agt tca gca aaa gat          1344
Ala Ala Leu Lys Ala Val Gln Ser Gly Asn Gly Ser Ser Ala Lys Asp
                    435                 440                 445 ttg gac tcg cta act aat caa ctc aat ggt tta aag gta aaa att aac          1392
Leu Asp Ser Leu Thr Asn Gln Leu Asn Gly Leu Lys Val Lys Ile Asn
        450                 455                 460 taa                                                                      1395

<210> SEQ ID NO 2
<211> LENGTH: 464
<212> TYPE: PRT
<213> ORGANISM: Nemophila menziesii

<400> SEQUENCE: 2

Met Pro Ser Ile Leu Ser Asn Ser Ala His Ile Leu Leu Phe Pro Phe
1               5                   10                  15

Pro Thr Ser Gly His Ile Ile Pro Ile Leu Asp Leu Ala Asn Gln Leu
                20                  25                  30

Leu Ala Arg Gly Leu Thr Ile Thr Ile Leu Ile Thr Pro Ala Asn Leu
            35                  40                  45

Thr Leu Leu Ser Thr Gln Leu Ile Glu Leu Asp Arg Leu Gly Ser Leu
```

```
            50                  55                  60
His Thr Leu Val Leu Pro Phe Pro Asn Pro Asn Pro Ser Glu Thr
 65                  70                  75                  80

Ser Leu Ala Ala Arg Val His Ala Ser Ser Gln Leu Ser Asn Thr Ile
                 85                  90                  95

Ile Gln Trp Phe Gln Ser His Thr Ser Pro Pro Val Ala Ile Val Ser
                100                 105                 110

Asp Phe Phe Leu Gly Trp Thr Asn Ser Leu Ala Ser Gln Leu Gly Ile
                115                 120                 125

Pro Arg Leu Val Phe Trp Pro Ser Gly Val Gln Arg Ser Ser Leu Val
                130                 135                 140

Asp Tyr Ile Trp Gln Asn Asp Gln Leu Ser Asp Ser Asp His Gln Ile
145                 150                 155                 160

Gln Asp Asn Ser Val Ile Ser Phe Pro Asp Val Pro Asn Ser Pro Ala
                165                 170                 175

Tyr Pro Lys Trp Gln Ala Cys Gly Leu Ser Thr Gln Tyr Lys Lys Gly
                180                 185                 190

Asp Pro Ser Trp Glu Phe Phe Lys Asn Gly Val Leu Ala Asn Thr Gln
                195                 200                 205

Ser Trp Gly Ala Ile Tyr Asn Ser Phe Arg Asp Leu Glu Gly Val Tyr
210                 215                 220

Ile Asp Tyr Ile Lys Lys Lys Met Gly His Gly Arg Val Trp Ala Val
225                 230                 235                 240

Gly Pro Leu Leu Pro Ala Asn Asp Ala Ser Lys Arg Gly Gly Ser Cys
                245                 250                 255

Val Met Pro Ile Asp Asp Val Met Thr Trp Leu Asp Thr Lys Thr Asn
                260                 265                 270

Ser Asp Asn Ser Val Val Tyr Val Cys Phe Gly Ser Arg Val Glu Leu
                275                 280                 285

Thr Thr Glu Gln Leu Asp Ser Leu Ala Ala Ala Leu Glu Ile Ser Gly
                290                 295                 300

Val His Phe Ile Leu Cys Val Lys Leu His Gln Glu Ile Ser Lys Glu
305                 310                 315                 320

Tyr Glu Asp Arg Val Ala Gly Arg Gly Leu Ile Ile Arg Gly Trp Ala
                325                 330                 335

Pro Gln Val Ala Ile Leu Arg His Arg Ala Val Gly Ala Phe Leu Thr
                340                 345                 350

His Cys Gly Trp Asn Ser Ile Leu Glu Gly Ile Ala Ala Gly Val Val
                355                 360                 365

Met Leu Thr Trp Pro Met Gly Ala Asp Gln Phe Thr Asn Ala Asn Leu
370                 375                 380

Leu Val Asp Glu Leu Lys Val Ala Met Lys Ala Cys Glu Gly Gly Asp
385                 390                 395                 400

Ser Asn Val Pro Asn Pro Ala Met Leu Ala Asn Val Leu Ala Glu Ser
                405                 410                 415

Ile Asn Gly Gly Arg Ala Glu Arg Glu Arg Val Thr Glu Leu Cys Asp
                420                 425                 430

Ala Ala Leu Lys Ala Val Gln Ser Gly Asn Gly Ser Ser Ala Lys Asp
                435                 440                 445

Leu Asp Ser Leu Thr Asn Gln Leu Asn Gly Leu Lys Val Lys Ile Asn
450                 455                 460

<210> SEQ ID NO 3
```

```
<211> LENGTH: 1428
<212> TYPE: DNA
<213> ORGANISM: Nemophila menziesii
<220> FEATURE:
<223> OTHER INFORMATION: NmGT4
<220> FEATURE:
<221> NAME/KEY: CDS
<222> LOCATION: (1)..(1425)

<400> SEQUENCE: 3 atg gca gct cag ctt cat gtt gtc ttc ttt cca ttc atg gct caa ggc      48
Met Ala Ala Gln Leu His Val Val Phe Phe Pro Phe Met Ala Gln Gly
1               5                   10                  15 cac tta ata ccc acc ctt gaa atg gtc aaa ctc ttc tct tct cgt ggt      96
His Leu Ile Pro Thr Leu Glu Met Val Lys Leu Phe Ser Ser Arg Gly
            20                  25                  30 ctt aag acc acc ata gtc acc act aaa ttt tat gct cct gcg gtt aca     144
Leu Lys Thr Thr Ile Val Thr Thr Lys Phe Tyr Ala Pro Ala Val Thr
        35                  40                  45 aaa tcc ata gaa aaa acc aaa cat aca gga aac caa atc aat ata att     192
Lys Ser Ile Glu Lys Thr Lys His Thr Gly Asn Gln Ile Asn Ile Ile
    50                  55                  60 atc ata aaa ttc cct tct gcc gag gtt gga tta ccc gaa gga tct gaa     240
Ile Ile Lys Phe Pro Ser Ala Glu Val Gly Leu Pro Glu Gly Ser Glu
65                  70                  75                  80 agt ctc gac aaa ctg aaa tca cct gac atg ttc atg aaa ttt ttc aag     288
Ser Leu Asp Lys Leu Lys Ser Pro Asp Met Phe Met Lys Phe Phe Lys
                85                  90                  95 gct ctt tct tta tta caa gaa cca ttt gag caa atc tta caa gaa ttg     336
Ala Leu Ser Leu Leu Gln Glu Pro Phe Glu Gln Ile Leu Gln Glu Leu
            100                 105                 110 tct cct gat tgt atc gtt tct gat atg ttc ttc cca tgg act act gct     384
Ser Pro Asp Cys Ile Val Ser Asp Met Phe Phe Pro Trp Thr Thr Ala
        115                 120                 125 tca gct gct aaa ttc gat atc ccg aga ttt gtt ttc cat ggt tta agt     432
Ser Ala Ala Lys Phe Asp Ile Pro Arg Phe Val Phe His Gly Leu Ser
    130                 135                 140 ctt ttc gca ctg tgt gtt tcg gag aat atg aga ttc tac aag cca ttc     480
Leu Phe Ala Leu Cys Val Ser Glu Asn Met Arg Phe Tyr Lys Pro Phe
145                 150                 155                 160 aag aat ctg gga tct gaa tca tta gat tca gaa ccg gtc atg ttg cct     528
Lys Asn Leu Gly Ser Glu Ser Leu Asp Ser Glu Pro Val Met Leu Pro
                165                 170                 175 gat ttc ccg aat cag att gag ttc agt aaa gtt caa gtc cct gaa ttt     576
Asp Phe Pro Asn Gln Ile Glu Phe Ser Lys Val Gln Val Pro Glu Phe
            180                 185                 190 gaa gtt ggt gaa agt aaa aac gag atc atg gag ttg tta aat caa gtt     624
Glu Val Gly Glu Ser Lys Asn Glu Ile Met Glu Leu Leu Asn Gln Val
        195                 200                 205 aag gaa tcc gag gtt aaa agc tat ggg att att atc aat agt ttt aat     672
Lys Glu Ser Glu Val Lys Ser Tyr Gly Ile Ile Ile Asn Ser Phe Asn
    210                 215                 220 gaa ctt gag aaa gat tac gtt gat tac tat aga aac gtt tgg gga aga     720
Glu Leu Glu Lys Asp Tyr Val Asp Tyr Tyr Arg Asn Val Trp Gly Arg
225                 230                 235                 240 cga gca tgg ctt ctt ggt cct tta tcg tta tct aat cgc gat gat gaa     768
Arg Ala Trp Leu Leu Gly Pro Leu Ser Leu Ser Asn Arg Asp Asp Glu
                245                 250                 255 gta aaa gat cag aca gat gaa cac gga tct tta aaa tgg ctt gat tcg     816
Val Lys Asp Gln Thr Asp Glu His Gly Ser Leu Lys Trp Leu Asp Ser
            260                 265                 270
```

| | | |
|---|---|---|
| aag aaa cca gat tca gtt att tac gta tgt ttt gga agt gta gcg cct<br>Lys Lys Pro Asp Ser Val Ile Tyr Val Cys Phe Gly Ser Val Ala Pro<br>275 280 285 | | 864 |
| tta agt agt tcg caa tta cac gag att gct tta gga ctt gaa tct tcg<br>Leu Ser Ser Ser Gln Leu His Glu Ile Ala Leu Gly Leu Glu Ser Ser<br>290 295 300 | | 912 |
| ggt caa cag ttc att tgg gta gtc aag gaa cgt gaa gat ggt gag aaa<br>Gly Gln Gln Phe Ile Trp Val Val Lys Glu Arg Glu Asp Gly Glu Lys<br>305 310 315 320 | | 960 |
| tgg tta cct gaa gga ttt gag gag aga att aag gat aag gga tta atc<br>Trp Leu Pro Glu Gly Phe Glu Glu Arg Ile Lys Asp Lys Gly Leu Ile<br>325 330 335 | | 1008 |
| ata cga ggg tgg gcc cca caa gta tcg att ctt gaa cat gaa tct aca<br>Ile Arg Gly Trp Ala Pro Gln Val Ser Ile Leu Glu His Glu Ser Thr<br>340 345 350 | | 1056 |
| ggg ggt ttc gtg act cat tgt ggg tgg aac tca gtg ctc gag gct gta<br>Gly Gly Phe Val Thr His Cys Gly Trp Asn Ser Val Leu Glu Ala Val<br>355 360 365 | | 1104 |
| tct gca ggg gta gtt atg gca aca ttg cct aca ttt gcg gaa caa cct<br>Ser Ala Gly Val Val Met Ala Thr Leu Pro Thr Phe Ala Glu Gln Pro<br>370 375 380 | | 1152 |
| ttt aac gaa aag ctg tta acg aaa gtt ttg aag att ggg ata cct att<br>Phe Asn Glu Lys Leu Leu Thr Lys Val Leu Lys Ile Gly Ile Pro Ile<br>385 390 395 400 | | 1200 |
| ggt tca cca tta tcg aat aga ggt aag agt ggt gtg aaa aaa gaa gag<br>Gly Ser Pro Leu Ser Asn Arg Gly Lys Ser Gly Val Lys Lys Glu Glu<br>405 410 415 | | 1248 |
| ata gct gag gcg atg aaa ggg att atg gaa ggt gaa gaa gct ctt gaa<br>Ile Ala Glu Ala Met Lys Gly Ile Met Glu Gly Glu Glu Ala Leu Glu<br>420 425 430 | | 1296 |
| atg aga atc cga gca aag agt ttg aaa gag atg gct tgg aaa gct gtt<br>Met Arg Ile Arg Ala Lys Ser Leu Lys Glu Met Ala Trp Lys Ala Val<br>435 440 445 | | 1344 |
| gaa gaa gga ggt tct tct tat aat gat ttg act tct ttg att gat gga<br>Glu Glu Gly Gly Ser Ser Tyr Asn Asp Leu Thr Ser Leu Ile Asp Gly<br>450 455 460 | | 1392 |
| gtc aaa gct tat cgt tca caa tca aac aag ata tga<br>Val Lys Ala Tyr Arg Ser Gln Ser Asn Lys Ile<br>465 470 475 | | 1428 |

<210> SEQ ID NO 4
<211> LENGTH: 475
<212> TYPE: PRT
<213> ORGANISM: Nemophila menziesii

<400> SEQUENCE: 4

Met Ala Ala Gln Leu His Val Val Phe Phe Pro Phe Met Ala Gln Gly
1               5                   10                  15

His Leu Ile Pro Thr Leu Glu Met Val Lys Leu Phe Ser Ser Arg Gly
                20                  25                  30

Leu Lys Thr Thr Ile Val Thr Thr Lys Phe Tyr Ala Pro Ala Val Thr
            35                  40                  45

Lys Ser Ile Glu Lys Thr Lys His Thr Gly Asn Gln Ile Asn Ile Ile
        50                  55                  60

Ile Ile Lys Phe Pro Ser Ala Glu Val Gly Leu Pro Glu Gly Ser Glu
65                  70                  75                  80

Ser Leu Asp Lys Leu Lys Ser Pro Asp Met Phe Met Lys Phe Lys
                85                  90                  95

Ala Leu Ser Leu Leu Gln Glu Pro Phe Glu Gln Ile Leu Gln Glu Leu

```
                100                 105                 110
Ser Pro Asp Cys Ile Val Ser Asp Met Phe Phe Pro Trp Thr Thr Ala
            115                 120                 125

Ser Ala Ala Lys Phe Asp Ile Pro Arg Phe Val Phe His Gly Leu Ser
        130                 135                 140

Leu Phe Ala Leu Cys Val Ser Glu Asn Met Arg Phe Tyr Lys Pro Phe
145                 150                 155                 160

Lys Asn Leu Gly Ser Glu Ser Leu Asp Ser Glu Pro Val Met Leu Pro
                165                 170                 175

Asp Phe Pro Asn Gln Ile Glu Phe Ser Lys Val Gln Val Pro Glu Phe
            180                 185                 190

Glu Val Gly Glu Ser Lys Asn Glu Ile Met Glu Leu Leu Asn Gln Val
        195                 200                 205

Lys Glu Ser Glu Val Lys Ser Tyr Gly Ile Ile Asn Ser Phe Asn
210                 215                 220

Glu Leu Glu Lys Asp Tyr Val Asp Tyr Arg Asn Val Trp Gly Arg
225                 230                 235                 240

Arg Ala Trp Leu Leu Gly Pro Leu Ser Leu Ser Asn Arg Asp Asp Glu
                245                 250                 255

Val Lys Asp Gln Thr Asp Glu His Gly Ser Leu Lys Trp Leu Asp Ser
            260                 265                 270

Lys Lys Pro Asp Ser Val Ile Tyr Val Cys Phe Gly Ser Val Ala Pro
        275                 280                 285

Leu Ser Ser Ser Gln Leu His Glu Ile Ala Leu Gly Leu Glu Ser Ser
    290                 295                 300

Gly Gln Gln Phe Ile Trp Val Val Lys Glu Arg Glu Asp Gly Glu Lys
305                 310                 315                 320

Trp Leu Pro Glu Gly Phe Glu Glu Arg Ile Lys Asp Lys Gly Leu Ile
                325                 330                 335

Ile Arg Gly Trp Ala Pro Gln Val Ser Ile Leu Glu His Glu Ser Thr
            340                 345                 350

Gly Gly Phe Val Thr His Cys Gly Trp Asn Ser Val Leu Glu Ala Val
        355                 360                 365

Ser Ala Gly Val Val Met Ala Thr Leu Pro Thr Phe Ala Glu Gln Pro
    370                 375                 380

Phe Asn Glu Lys Leu Leu Thr Lys Val Leu Lys Ile Gly Ile Pro Ile
385                 390                 395                 400

Gly Ser Pro Leu Ser Asn Arg Gly Lys Ser Gly Val Lys Lys Glu Glu
                405                 410                 415

Ile Ala Glu Ala Met Lys Gly Ile Met Glu Gly Glu Glu Ala Leu Glu
            420                 425                 430

Met Arg Ile Arg Ala Lys Ser Leu Lys Glu Met Ala Trp Lys Ala Val
        435                 440                 445

Glu Glu Gly Gly Ser Ser Tyr Asn Asp Leu Thr Ser Leu Ile Asp Gly
    450                 455                 460

Val Lys Ala Tyr Arg Ser Gln Ser Asn Lys Ile
465                 470                 475

<210> SEQ ID NO 5
<211> LENGTH: 1521
<212> TYPE: DNA
<213> ORGANISM: Viola x wittrockiana
<220> FEATURE:
<223> OTHER INFORMATION: Complete length Pansy F3'5'H cDNA
<220> FEATURE:
```

<221> NAME/KEY: CDS
<222> LOCATION: (1)..(1518)

<400> SEQUENCE: 5

```
atg gca att cta gtc acc gac ttc gtt gtc gcg gct ata att ttc ttg      48
Met Ala Ile Leu Val Thr Asp Phe Val Val Ala Ala Ile Ile Phe Leu
1               5                   10                  15 atc act cgg ttc tta gtt cgt tct ctt ttc aag aaa cca acc cga ccg      96
Ile Thr Arg Phe Leu Val Arg Ser Leu Phe Lys Lys Pro Thr Arg Pro
                20                  25                  30 ctc ccc ccg ggt cct ctc ggt tgg ccc ttg gtg ggc gcc ctc cct ctc     144
Leu Pro Pro Gly Pro Leu Gly Trp Pro Leu Val Gly Ala Leu Pro Leu
            35                  40                  45 cta ggc gcc atg cct cac gtc gca cta gcc aaa ctc gct aag aag tat     192
Leu Gly Ala Met Pro His Val Ala Leu Ala Lys Leu Ala Lys Lys Tyr
        50                  55                  60 ggt ccg atc atg cac cta aaa atg ggc acg tgc gac atg gtg gtc gcg     240
Gly Pro Ile Met His Leu Lys Met Gly Thr Cys Asp Met Val Val Ala
65                  70                  75                  80 tcc acc ccc gag tcg gct cga gcc ttc ctc aaa acg cta gac ctc aac     288
Ser Thr Pro Glu Ser Ala Arg Ala Phe Leu Lys Thr Leu Asp Leu Asn
                85                  90                  95 ttc tcc aac cgc cca ccc aac gcg ggc gca tcc cac cta gcg tac ggc     336
Phe Ser Asn Arg Pro Pro Asn Ala Gly Ala Ser His Leu Ala Tyr Gly
                100                 105                 110 gcg cag gac tta gtc ttc gcc aag tac ggt ccg agg tgg aag act tta     384
Ala Gln Asp Leu Val Phe Ala Lys Tyr Gly Pro Arg Trp Lys Thr Leu
            115                 120                 125 aga aaa ttg agc aac ctc cac atg cta ggc ggg aag gcg ttg gat gat     432
Arg Lys Leu Ser Asn Leu His Met Leu Gly Gly Lys Ala Leu Asp Asp
        130                 135                 140 tgg gca aat gtg agg gtc acc gag cta ggc cac atg ctt aaa gcc atg     480
Trp Ala Asn Val Arg Val Thr Glu Leu Gly His Met Leu Lys Ala Met
145                 150                 155                 160 tgc gag gcg agc cgg tgc ggg gag ccc gtg gtg ctg gcc gag atg ctc     528
Cys Glu Ala Ser Arg Cys Gly Glu Pro Val Val Leu Ala Glu Met Leu
                165                 170                 175 acg tac gcc atg gcg aac atg atc ggt caa gtg ata ctc agc cgg cgc     576
Thr Tyr Ala Met Ala Asn Met Ile Gly Gln Val Ile Leu Ser Arg Arg
                180                 185                 190 gtg ttc gtg acc aaa ggg acc gag tct aac gag ttc aaa gac atg gtg     624
Val Phe Val Thr Lys Gly Thr Glu Ser Asn Glu Phe Lys Asp Met Val
            195                 200                 205 gtc gag ttg atg acg tcc gcc ggg tac ttc aac atc ggt gac ttc ata     672
Val Glu Leu Met Thr Ser Ala Gly Tyr Phe Asn Ile Gly Asp Phe Ile
        210                 215                 220 ccc tcg atc gct tgg atg gat ttg caa ggg atc gag cga ggg atg aag     720
Pro Ser Ile Ala Trp Met Asp Leu Gln Gly Ile Glu Arg Gly Met Lys
225                 230                 235                 240 aag ctg cac acg aag ttt gat gtg tta ttg acg aag atg gtg aag gag     768
Lys Leu His Thr Lys Phe Asp Val Leu Leu Thr Lys Met Val Lys Glu
                245                 250                 255 cat aga gcg acg agt cat gag cgc aaa ggg aag gca gat ttc ctc gac     816
His Arg Ala Thr Ser His Glu Arg Lys Gly Lys Ala Asp Phe Leu Asp
                260                 265                 270 gtt ctc ttg gaa gaa tgc gac aat aca aat ggg gag aag ctt agt att     864
Val Leu Leu Glu Glu Cys Asp Asn Thr Asn Gly Glu Lys Leu Ser Ile
            275                 280                 285 acc aat atc aaa gct gtc ctt ttg aat cta ttc acg gcg ggc acg gac     912
Thr Asn Ile Lys Ala Val Leu Leu Asn Leu Phe Thr Ala Gly Thr Asp
```

```
                 290                 295                 300
aca tct tcg agc ata atc gaa tgg gcg tta acg gag atg atc aag aat        960
Thr Ser Ser Ser Ile Ile Glu Trp Ala Leu Thr Glu Met Ile Lys Asn
305                 310                 315                 320 ccg acg atc tta aaa aag gcg caa gag gag atg gat cga gtc atc ggt       1008
Pro Thr Ile Leu Lys Lys Ala Gln Glu Glu Met Asp Arg Val Ile Gly
                325                 330                 335 cgt gat cgg agg ctg ctc gaa tcg gac ata tcg agc ctc ccg tac cta       1056
Arg Asp Arg Arg Leu Leu Glu Ser Asp Ile Ser Ser Leu Pro Tyr Leu
            340                 345                 350 caa gcc att gct aaa gaa acg tat cgc aaa cac ccg tcg acg cct ctc       1104
Gln Ala Ile Ala Lys Glu Thr Tyr Arg Lys His Pro Ser Thr Pro Leu
        355                 360                 365 aac ttg ccg agg att gcg atc caa gca tgt gaa gtt gat ggc tac tac       1152
Asn Leu Pro Arg Ile Ala Ile Gln Ala Cys Glu Val Asp Gly Tyr Tyr
    370                 375                 380 atc cct aag gac gcg agg ctt agc gtg aac att tgg gcg atc ggt cgg       1200
Ile Pro Lys Asp Ala Arg Leu Ser Val Asn Ile Trp Ala Ile Gly Arg
385                 390                 395                 400 gac ccg aat gtt tgg gag aat ccg ttg gag ttc ttg ccg gaa aga ttc       1248
Asp Pro Asn Val Trp Glu Asn Pro Leu Glu Phe Leu Pro Glu Arg Phe
                405                 410                 415 ttg tct gaa gag aat ggg aag atc aat ccc ggt ggg aat gat ttt gag       1296
Leu Ser Glu Glu Asn Gly Lys Ile Asn Pro Gly Gly Asn Asp Phe Glu
            420                 425                 430 ctg att ccg ttt gga gcc ggg agg aga att tgt gcg ggg aca agg atg       1344
Leu Ile Pro Phe Gly Ala Gly Arg Arg Ile Cys Ala Gly Thr Arg Met
        435                 440                 445 gga atg gtc ctt gta agt tat att ttg ggc act ttg gtc cat tct ttt       1392
Gly Met Val Leu Val Ser Tyr Ile Leu Gly Thr Leu Val His Ser Phe
    450                 455                 460 gat tgg aaa tta cca aat ggt gtc gct gag ctt aat atg gat gaa agt       1440
Asp Trp Lys Leu Pro Asn Gly Val Ala Glu Leu Asn Met Asp Glu Ser
465                 470                 475                 480 ttt ggg ctt gca ttg caa aag gcc gtg ccg ctc tcg gcc ttg gtc agc       1488
Phe Gly Leu Ala Leu Gln Lys Ala Val Pro Leu Ser Ala Leu Val Ser
                485                 490                 495 cca cgg ttg gcc tca aac gcg tac gca acc tga                           1521
Pro Arg Leu Ala Ser Asn Ala Tyr Ala Thr
            500                 505

<210> SEQ ID NO 6
<211> LENGTH: 506
<212> TYPE: PRT
<213> ORGANISM: Viola x wittrockiana

<400> SEQUENCE: 6

Met Ala Ile Leu Val Thr Asp Phe Val Val Ala Ala Ile Ile Phe Leu
1               5                   10                  15

Ile Thr Arg Phe Leu Val Arg Ser Leu Phe Lys Lys Pro Thr Arg Pro
            20                  25                  30

Leu Pro Pro Gly Pro Leu Gly Trp Pro Leu Val Gly Ala Leu Pro Leu
        35                  40                  45

Leu Gly Ala Met Pro His Val Ala Leu Ala Lys Leu Ala Lys Lys Tyr
    50                  55                  60

Gly Pro Ile Met His Leu Lys Met Gly Thr Cys Asp Met Val Val Ala
65                  70                  75                  80

Ser Thr Pro Glu Ser Ala Arg Ala Phe Leu Lys Thr Leu Asp Leu Asn
                85                  90                  95
```

```
Phe Ser Asn Arg Pro Asn Ala Gly Ala Ser His Leu Ala Tyr Gly
            100                 105                 110

Ala Gln Asp Leu Val Phe Ala Lys Tyr Gly Pro Arg Trp Lys Thr Leu
        115                 120                 125

Arg Lys Leu Ser Asn Leu His Met Leu Gly Gly Lys Ala Leu Asp Asp
    130                 135                 140

Trp Ala Asn Val Arg Val Thr Glu Leu Gly His Met Leu Lys Ala Met
145                 150                 155                 160

Cys Glu Ala Ser Arg Cys Gly Glu Pro Val Val Leu Ala Glu Met Leu
                165                 170                 175

Thr Tyr Ala Met Ala Asn Met Ile Gly Gln Val Ile Leu Ser Arg Arg
            180                 185                 190

Val Phe Val Thr Lys Gly Thr Glu Ser Asn Glu Phe Lys Asp Met Val
        195                 200                 205

Val Glu Leu Met Thr Ser Ala Gly Tyr Phe Asn Ile Gly Asp Phe Ile
    210                 215                 220

Pro Ser Ile Ala Trp Met Asp Leu Gln Gly Ile Glu Arg Gly Met Lys
225                 230                 235                 240

Lys Leu His Thr Lys Phe Asp Val Leu Leu Thr Lys Met Val Lys Glu
                245                 250                 255

His Arg Ala Thr Ser His Glu Arg Lys Gly Lys Ala Asp Phe Leu Asp
            260                 265                 270

Val Leu Leu Glu Glu Cys Asp Asn Thr Asn Gly Glu Lys Leu Ser Ile
        275                 280                 285

Thr Asn Ile Lys Ala Val Leu Leu Asn Leu Phe Thr Ala Gly Thr Asp
    290                 295                 300

Thr Ser Ser Ser Ile Ile Glu Trp Ala Leu Thr Glu Met Ile Lys Asn
305                 310                 315                 320

Pro Thr Ile Leu Lys Lys Ala Gln Glu Glu Met Asp Arg Val Ile Gly
                325                 330                 335

Arg Asp Arg Arg Leu Leu Glu Ser Asp Ile Ser Ser Leu Pro Tyr Leu
            340                 345                 350

Gln Ala Ile Ala Lys Glu Thr Tyr Arg Lys His Pro Ser Thr Pro Leu
        355                 360                 365

Asn Leu Pro Arg Ile Ala Ile Gln Ala Cys Glu Val Asp Gly Tyr Tyr
    370                 375                 380

Ile Pro Lys Asp Ala Arg Leu Ser Val Asn Ile Trp Ala Ile Gly Arg
385                 390                 395                 400

Asp Pro Asn Val Trp Glu Asn Pro Leu Glu Phe Leu Pro Glu Arg Phe
                405                 410                 415

Leu Ser Glu Glu Asn Gly Lys Ile Asn Pro Gly Gly Asn Asp Phe Glu
            420                 425                 430

Leu Ile Pro Phe Gly Ala Gly Arg Arg Ile Cys Ala Gly Thr Arg Met
        435                 440                 445

Gly Met Val Leu Val Ser Tyr Ile Leu Gly Thr Leu Val His Ser Phe
    450                 455                 460

Asp Trp Lys Leu Pro Asn Gly Val Ala Glu Leu Asn Met Asp Glu Ser
465                 470                 475                 480

Phe Gly Leu Ala Leu Gln Lys Ala Val Pro Leu Ser Ala Leu Val Ser
                485                 490                 495

Pro Arg Leu Ala Ser Asn Ala Tyr Ala Thr
            500                 505
```

<210> SEQ ID NO 7
<211> LENGTH: 1539
<212> TYPE: DNA
<213> ORGANISM: Trenia fournier
<220> FEATURE:
<223> OTHER INFORMATION: Complete length Trenia FNS
<220> FEATURE:
<221> NAME/KEY: CDS
<222> LOCATION: (1)..(1536)

<400> SEQUENCE: 7

```
atg gac aca gtc tta atc aca ctc tac acc gcc ctg ttc gtc atc acc     48
Met Asp Thr Val Leu Ile Thr Leu Tyr Thr Ala Leu Phe Val Ile Thr
1               5                  10                  15 acc acc ttc ctc ctc ctc ctc cgc cga agg gga cca ccg tct ccg ccc     96
Thr Thr Phe Leu Leu Leu Leu Arg Arg Arg Gly Pro Pro Ser Pro Pro
            20                  25                  30 ggt cct ctc tcc cta ccc ata att ggc cac ctc cac ctc ctc ggc cca    144
Gly Pro Leu Ser Leu Pro Ile Ile Gly His Leu His Leu Leu Gly Pro
        35                  40                  45 aga ctc cac cac acg ttc cat gaa ttc tca ctc aaa tac ggc cca ttg    192
Arg Leu His His Thr Phe His Glu Phe Ser Leu Lys Tyr Gly Pro Leu
 50                  55                  60 atc cag ctc aag ctc ggc tcg atc ccg tgc gtc gtg gcc tcg acg ccc    240
Ile Gln Leu Lys Leu Gly Ser Ile Pro Cys Val Val Ala Ser Thr Pro
65                  70                  75                  80 gag ctc gcg aga gag ttt ctt aag acg aac gag ctc gcg ttc tcc tct    288
Glu Leu Ala Arg Glu Phe Leu Lys Thr Asn Glu Leu Ala Phe Ser Ser
                85                  90                  95 cgc aag cac tct acg gcc ata gac atc gtc acc tac gac tcg tcc ttt    336
Arg Lys His Ser Thr Ala Ile Asp Ile Val Thr Tyr Asp Ser Ser Phe
            100                 105                 110 gct ttc tct ccg tac gga ccc tac tgg aag tac atc aag aaa ctg tgt    384
Ala Phe Ser Pro Tyr Gly Pro Tyr Trp Lys Tyr Ile Lys Lys Leu Cys
        115                 120                 125 acc tac gag ctg ctc gga gcg agg aac ctc gga cac ttt cag ccc att    432
Thr Tyr Glu Leu Leu Gly Ala Arg Asn Leu Gly His Phe Gln Pro Ile
130                 135                 140 agg aat ctc gag gtc agg tcc ttt ctg cag ctt ctg atg cac aag agc    480
Arg Asn Leu Glu Val Arg Ser Phe Leu Gln Leu Leu Met His Lys Ser
145                 150                 155                 160 ttt aag ggc gag agt gtg aat gtg aca gac gag ctg gtg agg ctg acg    528
Phe Lys Gly Glu Ser Val Asn Val Thr Asp Glu Leu Val Arg Leu Thr
                165                 170                 175 agc aat gtg ata tcc cac atg atg ctg agc ata agg tgc tcg gaa gat    576
Ser Asn Val Ile Ser His Met Met Leu Ser Ile Arg Cys Ser Glu Asp
            180                 185                 190 gaa ggc gat gct gag gcg gcg aga aca gtg ata cgc gag gtg acg cag    624
Glu Gly Asp Ala Glu Ala Ala Arg Thr Val Ile Arg Glu Val Thr Gln
        195                 200                 205 ata ttt ggg gaa ttc gat gtt acg gac ata ata tgg ttt tgc aag aaa    672
Ile Phe Gly Glu Phe Asp Val Thr Asp Ile Ile Trp Phe Cys Lys Lys
210                 215                 220 ttc gat ctg cag ggg ata aag aag agg tca gag gat att cag agg agg    720
Phe Asp Leu Gln Gly Ile Lys Lys Arg Ser Glu Asp Ile Gln Arg Arg
225                 230                 235                 240 tat gat gct ttg ctc gag aag att att agt gat aga gag aga tcg agg    768
Tyr Asp Ala Leu Leu Glu Lys Ile Ile Ser Asp Arg Glu Arg Ser Arg
                245                 250                 255 agg caa aat cgt gat aag cat ggt ggc ggt aac aat gag gag gcc aag    816
Arg Gln Asn Arg Asp Lys His Gly Gly Gly Asn Asn Glu Glu Ala Lys
```

```
                260                 265                 270
gat ttt ctt gat atg ttg ctt gat gtg atg gag agt ggg gac acg gag      864
Asp Phe Leu Asp Met Leu Leu Asp Val Met Glu Ser Gly Asp Thr Glu
        275                 280                 285 gtc aaa ttc act aga gag cat ctc aag gct ttg att ctg gat ttc ttc      912
Val Lys Phe Thr Arg Glu His Leu Lys Ala Leu Ile Leu Asp Phe Phe
    290                 295                 300 acg gcc ggt acg gac aca aca gcc ata gcc acc gag tgg gcc atc gcc      960
Thr Ala Gly Thr Asp Thr Thr Ala Ile Ala Thr Glu Trp Ala Ile Ala
305                 310                 315                 320 gag ctc atc aac aac ccg aac gtc ttg aag aag gcc caa gaa gaa ata     1008
Glu Leu Ile Asn Asn Pro Asn Val Leu Lys Lys Ala Gln Glu Glu Ile
                325                 330                 335 tcc cgg atc atc gga acc aag cgg atc gta caa gaa tcc gac gcc cca     1056
Ser Arg Ile Ile Gly Thr Lys Arg Ile Val Gln Glu Ser Asp Ala Pro
            340                 345                 350 gac cta ccc tac ctc cag gcc atc atc aag gag acg ttc cgg ctc cac     1104
Asp Leu Pro Tyr Leu Gln Ala Ile Ile Lys Glu Thr Phe Arg Leu His
        355                 360                 365 cca ccg atc ccg atg ctc tcg cgt aag tcc acc tcc gat tgc acg gtc     1152
Pro Pro Ile Pro Met Leu Ser Arg Lys Ser Thr Ser Asp Cys Thr Val
    370                 375                 380 aac ggc tac aaa atc caa gcc aag agc ctc ttg ttc gtg aac ata tgg     1200
Asn Gly Tyr Lys Ile Gln Ala Lys Ser Leu Leu Phe Val Asn Ile Trp
385                 390                 395                 400 tcc atc ggt cga aac cct aat tac tgg gaa agc cct atg gag ttc agg     1248
Ser Ile Gly Arg Asn Pro Asn Tyr Trp Glu Ser Pro Met Glu Phe Arg
                405                 410                 415 ccc gag cgg ttc ttg gag aag gga cgc gag tcc atc gac gtc aag ggc     1296
Pro Glu Arg Phe Leu Glu Lys Gly Arg Glu Ser Ile Asp Val Lys Gly
            420                 425                 430 cag cac ttt gag ctc ttg cct ttt ggg acg ggc cgc agg ggc tgt ccc     1344
Gln His Phe Glu Leu Leu Pro Phe Gly Thr Gly Arg Arg Gly Cys Pro
        435                 440                 445 ggt atg ttg ctg gct ata caa gag gtg gtc agc atc att ggg acc atg     1392
Gly Met Leu Leu Ala Ile Gln Glu Val Val Ser Ile Ile Gly Thr Met
    450                 455                 460 gtt cag tgc ttc gac tgg aaa ttg gca gat ggt tcg ggc aat aat gtg     1440
Val Gln Cys Phe Asp Trp Lys Leu Ala Asp Gly Ser Gly Asn Asn Val
465                 470                 475                 480 gac atg acc gaa cgg tct gga ttg acc gct ccg aga gcg ttc gat ctg     1488
Asp Met Thr Glu Arg Ser Gly Leu Thr Ala Pro Arg Ala Phe Asp Leu
                485                 490                 495 gtt tgc cgg ttg tat cca cgg gtt gac ccg gcc aca ata tcg ggt gct     1536
Val Cys Arg Leu Tyr Pro Arg Val Asp Pro Ala Thr Ile Ser Gly Ala
            500                 505                 510 tga                                                                 1539

<210> SEQ ID NO 8
<211> LENGTH: 512
<212> TYPE: PRT
<213> ORGANISM: Trenia fournier

<400> SEQUENCE: 8

Met Asp Thr Val Leu Ile Thr Leu Tyr Thr Ala Leu Phe Val Ile Thr
1               5                   10                  15

Thr Thr Phe Leu Leu Leu Leu Arg Arg Arg Gly Pro Pro Ser Pro Pro
            20                  25                  30

Gly Pro Leu Ser Leu Pro Ile Ile Gly His Leu His Leu Leu Gly Pro
```

```
                35                  40                  45
Arg Leu His His Thr Phe His Glu Phe Ser Leu Lys Tyr Gly Pro Leu
 50                  55                  60
Ile Gln Leu Lys Leu Gly Ser Ile Pro Cys Val Val Ala Ser Thr Pro
65                  70                  75                  80
Glu Leu Ala Arg Glu Phe Leu Lys Thr Asn Glu Leu Ala Phe Ser Ser
                85                  90                  95
Arg Lys His Ser Thr Ala Ile Asp Ile Val Thr Tyr Asp Ser Ser Phe
            100                 105                 110
Ala Phe Ser Pro Tyr Gly Pro Tyr Trp Lys Tyr Ile Lys Lys Leu Cys
            115                 120                 125
Thr Tyr Glu Leu Leu Gly Ala Arg Asn Leu Gly His Phe Gln Pro Ile
            130                 135                 140
Arg Asn Leu Glu Val Arg Ser Phe Leu Gln Leu Met His Lys Ser
145                 150                 155                 160
Phe Lys Gly Glu Ser Val Asn Val Thr Asp Glu Leu Val Arg Leu Thr
                165                 170                 175
Ser Asn Val Ile Ser His Met Met Leu Ser Ile Arg Cys Ser Glu Asp
            180                 185                 190
Glu Gly Asp Ala Glu Ala Ala Arg Thr Val Ile Arg Glu Val Thr Gln
            195                 200                 205
Ile Phe Gly Glu Phe Asp Val Thr Asp Ile Ile Trp Phe Cys Lys Lys
210                 215                 220
Phe Asp Leu Gln Gly Ile Lys Lys Arg Ser Glu Asp Ile Gln Arg Arg
225                 230                 235                 240
Tyr Asp Ala Leu Leu Glu Lys Ile Ile Ser Asp Arg Glu Arg Ser Arg
                245                 250                 255
Arg Gln Asn Arg Asp Lys His Gly Gly Asn Glu Glu Ala Lys
            260                 265                 270
Asp Phe Leu Asp Met Leu Leu Asp Val Met Glu Ser Gly Asp Thr Glu
            275                 280                 285
Val Lys Phe Thr Arg Glu His Leu Lys Ala Leu Ile Leu Asp Phe Phe
290                 295                 300
Thr Ala Gly Thr Asp Thr Thr Ala Ile Ala Thr Glu Trp Ala Ile Ala
305                 310                 315                 320
Glu Leu Ile Asn Asn Pro Asn Val Leu Lys Lys Ala Gln Glu Glu Ile
                325                 330                 335
Ser Arg Ile Ile Gly Thr Lys Arg Ile Val Gln Glu Ser Asp Ala Pro
            340                 345                 350
Asp Leu Pro Tyr Leu Gln Ala Ile Ile Lys Glu Thr Phe Arg Leu His
            355                 360                 365
Pro Pro Ile Pro Met Leu Ser Arg Lys Ser Thr Ser Asp Cys Thr Val
            370                 375                 380
Asn Gly Tyr Lys Ile Gln Ala Lys Ser Leu Leu Phe Val Asn Ile Trp
385                 390                 395                 400
Ser Ile Gly Arg Asn Pro Asn Tyr Trp Glu Ser Pro Met Glu Phe Arg
                405                 410                 415
Pro Glu Arg Phe Leu Glu Lys Gly Arg Glu Ser Ile Asp Val Lys Gly
            420                 425                 430
Gln His Phe Glu Leu Leu Pro Phe Gly Thr Gly Arg Arg Gly Cys Pro
            435                 440                 445
Gly Met Leu Leu Ala Ile Gln Glu Val Val Ser Ile Ile Gly Thr Met
450                 455                 460
```

```
Val Gln Cys Phe Asp Trp Lys Leu Ala Asp Gly Ser Gly Asn Asn Val
465                 470                 475                 480

Asp Met Thr Glu Arg Ser Gly Leu Thr Ala Pro Arg Ala Phe Asp Leu
                485                 490                 495

Val Cys Arg Leu Tyr Pro Arg Val Asp Pro Ala Thr Ile Ser Gly Ala
            500                 505                 510

<210> SEQ ID NO 9
<211> LENGTH: 4087
<212> TYPE: DNA
<213> ORGANISM: Perilla frutescens
<220> FEATURE:
<223> OTHER INFORMATION: Perilla 3AT

<400> SEQUENCE: 9
aactattatg atcccacaga gttttttgaca gatgagtctt caggaggaga tgctgaacct      60
tttcactact ctactgaacg catcacaagt ttatcggctt atatgactaa tagggatcaa     120
cttcacaaca gagaggctca tagagctctt aaagaggatt tgatcgagca catatggaaa     180
aaattcggca ctaactaaat atataattta cgttttatgc actcgtaatt taaaatttca     240
tgtgtctcat tgtagtttat ttaattatgt tttcactctt gtaatttta ttttgttgtg      300 aagtaaatta tgaatttata attatatggg taattttttg ataattatgc aattaaaaat     360
aattaatatt ttttaaatgc aagagaaaaa tgttatttta ataacatgtt cttattaaaa     420
aataaaatga taaatatttt atgtaggttg ggagaaaatg aaaaaataat attttatttg     480
aaggttgggt tggatgaggt cactgatggg agtataaata atactccctc cgtcccataa     540
ttattgtcca ttattccttt tgggatgtc ccaaaattat agtcctattc taaattggga      600
ttgtatttaa atattctttt acaaatataa ccctatttga tatagtatga atgcaattaa     660
tatagtaaaa aaataagggc aatataggat aattattgta aattgtatat ttccaataca     720
tattaaatgt gatttcttaa tctgtgtgaa aataggaagt ggactataat tatgggacgg     780
agggagtata aagttggagg ttgtggatgt ggaggagaaa gaaattaata ttttatttaa     840
agattggatt aaaggaggtc actgatgtgg gtagtcttag aggaaatgta gtcttagagg     900
aaatctgccc agcaaaataa aataataagt aaataaataa actaaatatg tattgaatgc     960
gacatctagc aatatagcca catatatagt gcagtagcac gcagcgctcg ttactcgtca    1020
gtcgtcaaag aatggtaagt atagaaaagc atctttaaat aacacaccaa aaaccacagc    1080
tacgttcaac accgccatga ccaccaccgt gatcgaaacg tgtagagttg gccaccgcc     1140 ggactcggtg gcggagcaat cgttgccgct cacattcttc gacatgacgt ggctgcattt    1200
tcatcccatg cttcagctcc tcttctacga attcccttgt tccaagcaac atttctcaga    1260
atccatcatt ccaaaactca acaatctct ctctaaaact ctcatacact tcttccctct     1320
ctcatgcaat ttaatctacc cttcatctcc ggagaaaatg cccgagtttc ggtatctatc    1380
gggggactcg gtttctttca ctatcgcaga atctagcgac gacttcgatg atctcgtcgg    1440
aaatcgcgca gaatctcccg ttaggctcta caacttcgtc cctaaattgc cgcagattgt    1500
cgaagaatct gatagaaaac tcttccaagt tttcgccgtg caggtgactc ttttcccagg    1560
tcgaggcgtc ggtattggaa tagcaacgca tcacaccgtt agcgatgccc cgtcgtttct    1620
cgcctttata acggcttggg cttggatgag caaacacatt gaagatgaag atgaagagtt    1680
taaatctttg ccagttttcg atagatccgt cataaaatat ccgacgaaat ttgactcgat    1740
ttattggaaa aaggcgctaa aatttccttt gcaatctcgt catccctcat taccgacgga    1800
```

```
ccgcattcga accacgttcg ttttcaccca atccgaaatt aagaaattga agggttcgat    1860
tcagtccaga gttccaagtt tagtccatct ctcatctttt gtagcgattg cagcttatat    1920
gtgggctggc gtaacgaaat cactcacagc agatgaagac cacgacgacg gggatgcatt    1980
tttcttgatt ccggtcgatc taaggccacg attagatccg ccagttcccg aaaattactt    2040
cgggaactgc ttatcgtacg cgctgccgag aatgcggcgg cgagagctgg tgggagagaa    2100
aggggtgttt ctggcggctg aggcaatcgc ggcggagatc aaaaaaagga tcaacgacaa    2160
gagaatatta gaaacggtgg agaaatggtc gctggagatt cgtgaagcgt tgcagaaatc    2220 atattttttcg gtggcaggat cgagcaagct agatctttac ggtgcagatt ttggatgggg    2280
gaaggcgaga aagcaagaaa tattgtcgat tgatggggag aaatatgcaa tgacgctttg    2340
taaagccagg gatttcgaag gaggattgga ggtttgcttg tctttgccta aggacaaaat    2400
ggatgctttt gctgcttatt tttcagcggg aattaatggt taataaatgt atgtaattaa    2460
actaatatta ttatgtaaca attaattaag tgttgagtaa cgtgaagaat aatatctttt    2520
acctattata tatttatgag ttggttcaaa taaaatcact tcatttattg tattaaccgt    2580
ttagtgttct tctcaccata ttttggtgct attttttaaa aaatgttttt tttattgtat    2640
tttagtatta attgttttac cactaaaatt acagtaaaat gcaagatagt ttaatttta    2700 catttacata tgaaacacat tctctttata accaacctct ctatatatat aatatgtgtg    2760
tatgtatgta tacacatgta tgaatactag aaatatatct taaaccatcc atccttcaaa    2820
aatttcgggg ccatattgca tggtgacatt ataatatttg ataatttctt cgaacacgtt    2880
attaattcaa tttaataatt ctaataaaaa gacgctcaga caatatatgt agataggatc    2940
ggcccaaagg ggtgtctggg tgggctgtcg cccatgggcc ccgaaatctt aggggcaaaa    3000
aaaaaaaaat tcattatacc tagggcaaaa aaattaccgc tcttcacttc tctgcctctc    3060
tccctcatcc ctcgttcctc ctctctcttc cctatgtacg cctctttcac tccctccccc    3120
tctctcagtt ctctatcact tgtattttgt attgaaaact tgttgaaaac taaaccaaaa    3180
atagaaaaag gtatagaaaa tttgaaaaca aaggttgttt ttttgtgttg ctgcagttcc    3240
caaacttgcc gagttgccga cttgccgtgt tgaattgtta tatatgttaa aagcctaaaa    3300
tatatccttt cagaattgag atggattgtt gtaactatca ggttttttt attgagaatt    3360 ttagatcaat tagttatctt gtaatttttt attcttttta atacaatact ccctccatcc    3420
caatagcaag gtccccttgc tattgggcac gggtattaag gaggaggatt attataatga    3480
aaattaatat aaagtaagtg gattccactt tattaaggaa tattataatc aaaagtaata    3540 taagtaagt ggattccact ttaattagga cactaattat tttctttttt ggtatgagac    3600
tttgctattg ggcatccca aaaggcaaa agagaccttg ctattaggac ggtggacgtg    3660
ctgccgaggc acgcaaatta atttaccttt cctcttctat actaactcgt agtagcggcg    3720
agtaaaggtc gaaccctcaa ggagcaattg aactagatgt gctattagaa ataaaataaa    3780
cacaagtgag aggggagttt ttggtttcaa tttaactaaa actaattatg aaaatgaaaa    3840
aacaaatata aaacataaac aggtagacga aatatgataa agatagaatt ctagttctcg    3900
gttcagttat caccttt ctc caagtatttc atgaataatg caacgcctct tttcatacaa    3960
cttagaatcg atgtccaaag gttaatatca agctttattt acctaattgt ctcgtacgat    4020
tagttaacta aaacaagctc tttaattaac tctactcaat tagataacct agaataagct    4080
ctctaga                                                              4087
```

<210> SEQ ID NO 10
<211> LENGTH: 1356
<212> TYPE: DNA
<213> ORGANISM: Lavender officinallis
<220> FEATURE:
<223> OTHER INFORMATION: Lavender 3AT
<220> FEATURE:
<221> NAME/KEY: CDS
<222> LOCATION: (1)..(1353)

<400> SEQUENCE: 10

```
atg acc acc ctc ctc gaa tcc tcc cga gtg gcg ccg cct cca ggc acg        48
Met Thr Thr Leu Leu Glu Ser Ser Arg Val Ala Pro Pro Pro Gly Thr
1               5                  10                  15 gtg gct gag cag tca ctc ccg ctc acc ttc ttc gac atg acg tgg ctg        96
Val Ala Glu Gln Ser Leu Pro Leu Thr Phe Phe Asp Met Thr Trp Leu
                20                  25                  30 cat ttc cac ccc atg ctt cag ctt ctc ttc tac gaa ctc ccc tgt tcc       144
His Phe His Pro Met Leu Gln Leu Leu Phe Tyr Glu Leu Pro Cys Ser
            35                  40                  45 aaa ccc gcc ttc ctc gaa acc gtc gtt ccg aaa ctc aaa caa tcc tta       192
Lys Pro Ala Phe Leu Glu Thr Val Val Pro Lys Leu Lys Gln Ser Leu
        50                  55                  60 tct cta acc ctc aaa cac ttc ttc ccc ctt tca tgc aat cta atc tac       240
Ser Leu Thr Leu Lys His Phe Phe Pro Leu Ser Cys Asn Leu Ile Tyr
65                  70                  75                  80 cct cta tcg ccg gag aaa atg ccg gag ttc cgg tat cag aac ggt gac       288
Pro Leu Ser Pro Glu Lys Met Pro Glu Phe Arg Tyr Gln Asn Gly Asp
                85                  90                  95 tcg gtt tct ttc acg att atg gag tct agc gac gat tat gaa gat ctc       336
Ser Val Ser Phe Thr Ile Met Glu Ser Ser Asp Asp Tyr Glu Asp Leu
            100                 105                 110 gtc gga gat cat ccg cat tcc gct cat aaa tac tac tgc ttt gcc cct       384
Val Gly Asp His Pro His Ser Ala His Lys Tyr Tyr Cys Phe Ala Pro
        115                 120                 125 cag ctg ccg ccg ata gtc gag gaa tct gat cgg aaa ttg ttt caa gtt       432
Gln Leu Pro Pro Ile Val Glu Glu Ser Asp Arg Lys Leu Phe Gln Val
    130                 135                 140 tta gcc gtg caa gtg act ctg ttt ccc ggt cgc ggg gtg tgc atc gga       480
Leu Ala Val Gln Val Thr Leu Phe Pro Gly Arg Gly Val Cys Ile Gly
145                 150                 155                 160 ata acg acg cac cac acc gtt agc gat gct cca tcg ttt gta ggg ttt       528
Ile Thr Thr His His Thr Val Ser Asp Ala Pro Ser Phe Val Gly Phe
                165                 170                 175 atg aag agt tgg gct tcc atc act aaa ttc gga gga gat gat gaa ttc       576
Met Lys Ser Trp Ala Ser Ile Thr Lys Phe Gly Gly Asp Asp Glu Phe
            180                 185                 190 ttg gac gga aaa ggt gaa tgt ttg ccg gtt ttc gac cga tcg ctc gtg       624
Leu Asp Gly Lys Gly Glu Cys Leu Pro Val Phe Asp Arg Ser Leu Val
        195                 200                 205 aat tat ccg cct aaa ttg gac aca tat tta tgg aac aac gcg cag aaa       672
Asn Tyr Pro Pro Lys Leu Asp Thr Tyr Leu Trp Asn Asn Ala Gln Lys
    210                 215                 220 cgt ccg ttg gaa tcg cag cat cca tct tta ccg acg gat cgg att cga       720
Arg Pro Leu Glu Ser Gln His Pro Ser Leu Pro Thr Asp Arg Ile Arg
225                 230                 235                 240 gct acc tac ctt ttc acc caa tct gaa att aag aaa ttg aag ggt ttg       768
Ala Thr Tyr Leu Phe Thr Gln Ser Glu Ile Lys Lys Leu Lys Gly Leu
                245                 250                 255 att cag aga aaa gcc cca aat gta gtt aat ctc tct tcc ttc gtc gcg       816
Ile Gln Arg Lys Ala Pro Asn Val Val Asn Leu Ser Ser Phe Val Ala
```

```
                    260                 265                 270
atc gca gct tat atc tgg acc ggc atc gcc aaa tcg gtc gga gat tac         864
Ile Ala Ala Tyr Ile Trp Thr Gly Ile Ala Lys Ser Val Gly Asp Tyr
        275                 280                 285 aaa gac gtg gat gac gac aaa cgc gct ttc ttt tta att ccg atc gat         912
Lys Asp Val Asp Asp Asp Lys Arg Ala Phe Phe Leu Ile Pro Ile Asp
    290                 295                 300 tta agg ccg cgt ttg gat ccg ccg gct ccg ggg aac tac ttc gga aac         960
Leu Arg Pro Arg Leu Asp Pro Pro Ala Pro Gly Asn Tyr Phe Gly Asn
305                 310                 315                 320 tgt cta tcg ttt gcg atg gcg aag atc ctg cgg cgg gat ttg gtc gga        1008
Cys Leu Ser Phe Ala Met Ala Lys Ile Leu Arg Arg Asp Leu Val Gly
                325                 330                 335 gat gaa ggg gtg ttt cgg gca gct gag gcg atc gcg gcg gaa ata gag        1056
Asp Glu Gly Val Phe Arg Ala Ala Glu Ala Ile Ala Ala Glu Ile Glu
            340                 345                 350 aag agg acg agc gac aag aag att cta gaa act gtg gag aac tgg ccg        1104
Lys Arg Thr Ser Asp Lys Lys Ile Leu Glu Thr Val Glu Asn Trp Pro
        355                 360                 365 tct gag att cgc gaa gcc ttg caa aac tgt tat ttc tcg gtg gcg gga        1152
Ser Glu Ile Arg Glu Ala Leu Gln Asn Cys Tyr Phe Ser Val Ala Gly
    370                 375                 380 tcg agc agg ctt gat ctt tac ggc gcg gat ttt gga tgg ggt aag gcg        1200
Ser Ser Arg Leu Asp Leu Tyr Gly Ala Asp Phe Gly Trp Gly Lys Ala
385                 390                 395                 400 gtg aag caa gag ata ctg tcg att gat gga gag aag ttt acg atg tcg        1248
Val Lys Gln Glu Ile Leu Ser Ile Asp Gly Glu Lys Phe Thr Met Ser
                405                 410                 415 ttg tgt aaa ccg agg gat gct gcc gga gga ttg gag gtt gga ttg tct        1296
Leu Cys Lys Pro Arg Asp Ala Ala Gly Gly Leu Glu Val Gly Leu Ser
            420                 425                 430 ttg cca aag gag gaa ttg caa gct ttt gat gat tat ttt gcg gag gga        1344
Leu Pro Lys Glu Glu Leu Gln Ala Phe Asp Asp Tyr Phe Ala Glu Gly
        435                 440                 445 ata aag ggt tga                                                        1356
Ile Lys Gly
    450

<210> SEQ ID NO 11
<211> LENGTH: 451
<212> TYPE: PRT
<213> ORGANISM: Lavender officinallis

<400> SEQUENCE: 11

Met Thr Thr Leu Leu Glu Ser Ser Arg Val Ala Pro Pro Gly Thr
1               5                   10                  15

Val Ala Glu Gln Ser Leu Pro Leu Thr Phe Phe Asp Met Thr Trp Leu
            20                  25                  30

His Phe His Pro Met Leu Gln Leu Leu Phe Tyr Glu Leu Pro Cys Ser
        35                  40                  45

Lys Pro Ala Phe Leu Glu Thr Val Val Pro Lys Leu Lys Gln Ser Leu
    50                  55                  60

Ser Leu Thr Leu Lys His Phe Phe Pro Leu Ser Cys Asn Leu Ile Tyr
65                  70                  75                  80

Pro Leu Ser Pro Glu Lys Met Pro Glu Phe Arg Tyr Gln Asn Gly Asp
                85                  90                  95

Ser Val Ser Phe Thr Ile Met Glu Ser Ser Asp Asp Tyr Glu Asp Leu
            100                 105                 110
```

Val Gly Asp His Pro His Ser Ala His Lys Tyr Tyr Cys Phe Ala Pro
115                 120                 125

Gln Leu Pro Pro Ile Val Glu Glu Ser Asp Arg Lys Leu Phe Gln Val
130                 135                 140

Leu Ala Val Gln Val Thr Leu Phe Pro Gly Arg Gly Val Cys Ile Gly
145                 150                 155                 160

Ile Thr Thr His His Thr Val Ser Asp Ala Pro Ser Phe Val Gly Phe
                165                 170                 175

Met Lys Ser Trp Ala Ser Ile Thr Lys Phe Gly Gly Asp Asp Glu Phe
            180                 185                 190

Leu Asp Gly Lys Gly Glu Cys Leu Pro Val Phe Asp Arg Ser Leu Val
        195                 200                 205

Asn Tyr Pro Pro Lys Leu Asp Thr Tyr Leu Trp Asn Asn Ala Gln Lys
210                 215                 220

Arg Pro Leu Glu Ser Gln His Pro Ser Leu Pro Thr Asp Arg Ile Arg
225                 230                 235                 240

Ala Thr Tyr Leu Phe Thr Gln Ser Glu Ile Lys Lys Leu Lys Gly Leu
                245                 250                 255

Ile Gln Arg Lys Ala Pro Asn Val Val Asn Leu Ser Ser Phe Val Ala
            260                 265                 270

Ile Ala Ala Tyr Ile Trp Thr Gly Ile Ala Lys Ser Val Gly Asp Tyr
        275                 280                 285

Lys Asp Val Asp Asp Lys Arg Ala Phe Phe Leu Ile Pro Ile Asp
290                 295                 300

Leu Arg Pro Arg Leu Asp Pro Pro Ala Pro Gly Asn Tyr Phe Gly Asn
305                 310                 315                 320

Cys Leu Ser Phe Ala Met Ala Lys Ile Leu Arg Arg Asp Leu Val Gly
                325                 330                 335

Asp Glu Gly Val Phe Arg Ala Ala Glu Ala Ile Ala Ala Glu Ile Glu
            340                 345                 350

Lys Arg Thr Ser Asp Lys Lys Ile Leu Glu Thr Val Glu Asn Trp Pro
        355                 360                 365

Ser Glu Ile Arg Glu Ala Leu Gln Asn Cys Tyr Phe Ser Val Ala Gly
370                 375                 380

Ser Ser Arg Leu Asp Leu Tyr Gly Ala Asp Phe Gly Trp Gly Lys Ala
385                 390                 395                 400

Val Lys Gln Glu Ile Leu Ser Ile Asp Gly Glu Lys Phe Thr Met Ser
                405                 410                 415

Leu Cys Lys Pro Arg Asp Ala Ala Gly Gly Leu Glu Val Gly Leu Ser
            420                 425                 430

Leu Pro Lys Glu Glu Leu Gln Ala Phe Asp Asp Tyr Phe Ala Glu Gly
        435                 440                 445

Ile Lys Gly
450

<210> SEQ ID NO 12
<211> LENGTH: 1437
<212> TYPE: DNA
<213> ORGANISM: Salvia uliginousa
<220> FEATURE:
<223> OTHER INFORMATION: SuGT5 complete cDNA
<220> FEATURE:
<221> NAME/KEY: CDS
<222> LOCATION: (1)..(1434)

<400> SEQUENCE: 12

```
atg aaa cag cta cac atc gcc ctc ttc cca tcc atg gcc cat ggc cac        48
Met Lys Gln Leu His Ile Ala Leu Phe Pro Ser Met Ala His Gly His
1               5                   10                  15 atg atc ccc atg ttt gaa ctg gcg aag ctc ttc acc tca aga ggc ctc        96
Met Ile Pro Met Phe Glu Leu Ala Lys Leu Phe Thr Ser Arg Gly Leu
            20                  25                  30 aaa gcc acc atc atc gcc acc cca gcc ttc gca gcc ccc atc acc aaa       144
Lys Ala Thr Ile Ile Ala Thr Pro Ala Phe Ala Ala Pro Ile Thr Lys
        35                  40                  45 gcc caa caa tcc ggc ctc gat gtc ggc ctc gcc atc acc cca ttc cct       192
Ala Gln Gln Ser Gly Leu Asp Val Gly Leu Ala Ile Thr Pro Phe Pro
50                  55                  60 cca aag ggc tcc tcc ctg ccc cag aac atc att gct ttc gac caa atg       240
Pro Lys Gly Ser Ser Leu Pro Gln Asn Ile Ile Ala Phe Asp Gln Met
65                  70                  75                  80 acc aat ccc gat ctc acc acc agc ttc ctc cgg gcg atg gag ctg ctt       288
Thr Asn Pro Asp Leu Thr Thr Ser Phe Leu Arg Ala Met Glu Leu Leu
                85                  90                  95 cag gag ccc gtc gag gca atc ctg caa gag ctc cac ccc gac tgc ctc       336
Gln Glu Pro Val Glu Ala Ile Leu Gln Glu Leu His Pro Asp Cys Leu
            100                 105                 110 gtc tct gac atg ttc ctg ccg tgg act gcc gac tct gcc gcc aaa ttc       384
Val Ser Asp Met Phe Leu Pro Trp Thr Ala Asp Ser Ala Ala Lys Phe
        115                 120                 125 caa atc cca cgg ctg gcc ttc tac ggc acc agc tac ttc tca cgg tgt       432
Gln Ile Pro Arg Leu Ala Phe Tyr Gly Thr Ser Tyr Phe Ser Arg Cys
130                 135                 140 gtg tcg gag caa gtg ggt gac aag ccc ttc aac aac gtg acg tcg gat       480
Val Ser Glu Gln Val Gly Asp Lys Pro Phe Asn Asn Val Thr Ser Asp
145                 150                 155                 160 tcg gag cct gtt ctt gtg cct ggt ctt cct cag caa atc aag ttt gta       528
Ser Glu Pro Val Leu Val Pro Gly Leu Pro Gln Gln Ile Lys Phe Val
                165                 170                 175 agg tca caa ttt tct cca gtt ctt ctt gaa gaa act cag aat gac ttc       576
Arg Ser Gln Phe Ser Pro Val Leu Leu Glu Glu Thr Gln Asn Asp Phe
            180                 185                 190 gcc aaa ctg ttc aag caa atg act gaa gct tgg aag aag aca tac gga       624
Ala Lys Leu Phe Lys Gln Met Thr Glu Ala Trp Lys Lys Thr Tyr Gly
        195                 200                 205 gag gtt gtg aat agc ttc aac gag ctc gaa tcc gat tac gcc aat cac       672
Glu Val Val Asn Ser Phe Asn Glu Leu Glu Ser Asp Tyr Ala Asn His
210                 215                 220 tac aag aat gtt att ggg agg aag gca tgg gag att ggc cct ctt ctg       720
Tyr Lys Asn Val Ile Gly Arg Lys Ala Trp Glu Ile Gly Pro Leu Leu
225                 230                 235                 240 cta tgc agc agc agc aaa ggc ggc gaa aag aat cag cag aga gga aag       768
Leu Cys Ser Ser Ser Lys Gly Gly Glu Lys Asn Gln Gln Arg Gly Lys
                245                 250                 255 gaa tcc gcc att gat gag cac gag tgc ttg gct tgg ctc gac tcg aag       816
Glu Ser Ala Ile Asp Glu His Glu Cys Leu Ala Trp Leu Asp Ser Lys
            260                 265                 270 aat ccc aac tcc gtc gtc tac gtt tgt gcc ggc agc gtc gcc tcc ttc       864
Asn Pro Asn Ser Val Val Tyr Val Cys Ala Gly Ser Val Ala Ser Phe
        275                 280                 285 agc caa gca cag ctg cgc gag acc gcg atg ggg ctg gag gcg tcc ggc       912
Ser Gln Ala Gln Leu Arg Glu Thr Ala Met Gly Leu Glu Ala Ser Gly
290                 295                 300 caa aat ttc gtc tgg gtc gtg agg aaa aac aaa gaa gat gac gac gac       960
Gln Asn Phe Val Trp Val Val Arg Lys Asn Lys Glu Asp Asp Asp Asp
305                 310                 315                 320
```

```
tgg ctg ccg gta gga ttt gag gag aga gtg ggg aac aga ggg ctg atc     1008
Trp Leu Pro Val Gly Phe Glu Glu Arg Val Gly Asn Arg Gly Leu Ile
            325                 330                 335 ata agg ggg tgg gct cct caa gtg atg att ctc aat cat gcg gcg gta     1056
Ile Arg Gly Trp Ala Pro Gln Val Met Ile Leu Asn His Ala Ala Val
    340                 345                 350 ggg gct ttt gtg acg cac tgt gga tgg aac tcg act ctg gaa ggg gta     1104
Gly Ala Phe Val Thr His Cys Gly Trp Asn Ser Thr Leu Glu Gly Val
355                 360                 365 tgc gct ggc ttg ccg atg gtg aca tgg cca gtt ttc gca gag cag ttt     1152
Cys Ala Gly Leu Pro Met Val Thr Trp Pro Val Phe Ala Glu Gln Phe
    370                 375                 380 ttc aat gaa aag ctg gtg aca gag gtg ttg ggg acg ggg gtg tct gtt     1200
Phe Asn Glu Lys Leu Val Thr Glu Val Leu Gly Thr Gly Val Ser Val
385                 390                 395                 400 ggg aat aag agg tgg atg ctt agg gag agc gag gga gtc gag cgg gat     1248
Gly Asn Lys Arg Trp Met Leu Arg Glu Ser Glu Gly Val Glu Arg Asp
                405                 410                 415 gcg gtg gca agg gcg gtg gag gag atc atg gtg ggc gga gga gcg gag     1296
Ala Val Ala Arg Ala Val Glu Glu Ile Met Val Gly Gly Gly Ala Glu
            420                 425                 430 gag atg aga agc aga gct gag aat tat aag gaa atg gca aag aag gct     1344
Glu Met Arg Ser Arg Ala Glu Asn Tyr Lys Glu Met Ala Lys Lys Ala
        435                 440                 445 gtt gaa gaa ggt gga tct tca tat aat aat ttg aat gct ctc att gag     1392
Val Glu Glu Gly Gly Ser Ser Tyr Asn Asn Leu Asn Ala Leu Ile Glu
    450                 455                 460 gaa ttg agc aac tat gtt gct ccc acc ata caa gac aaa aat tag        1437
Glu Leu Ser Asn Tyr Val Ala Pro Thr Ile Gln Asp Lys Asn
465                 470                 475

<210> SEQ ID NO 13
<211> LENGTH: 478
<212> TYPE: PRT
<213> ORGANISM: Salvia uliginousa

<400> SEQUENCE: 13

Met Lys Gln Leu His Ile Ala Leu Phe Pro Ser Met Ala His Gly His
1               5                   10                  15

Met Ile Pro Met Phe Glu Leu Ala Lys Leu Phe Thr Ser Arg Gly Leu
            20                  25                  30

Lys Ala Thr Ile Ile Ala Thr Pro Ala Phe Ala Ala Pro Ile Thr Lys
        35                  40                  45

Ala Gln Gln Ser Gly Leu Asp Val Gly Leu Ala Ile Thr Pro Phe Pro
    50                  55                  60

Pro Lys Gly Ser Ser Leu Pro Gln Asn Ile Ile Ala Phe Asp Gln Met
65                  70                  75                  80

Thr Asn Pro Asp Leu Thr Thr Ser Phe Leu Arg Ala Met Glu Leu Leu
                85                  90                  95

Gln Glu Pro Val Glu Ala Ile Leu Gln Glu Leu His Pro Asp Cys Leu
            100                 105                 110

Val Ser Asp Met Phe Leu Pro Trp Thr Ala Asp Ser Ala Ala Lys Phe
        115                 120                 125

Gln Ile Pro Arg Leu Ala Phe Tyr Gly Thr Ser Tyr Phe Ser Arg Cys
    130                 135                 140

Val Ser Glu Gln Val Gly Asp Lys Pro Phe Asn Asn Val Thr Ser Asp
145                 150                 155                 160
```

```
Ser Glu Pro Val Leu Val Pro Gly Leu Pro Gln Gln Ile Lys Phe Val
            165                 170                 175

Arg Ser Gln Phe Ser Pro Val Leu Leu Glu Glu Thr Gln Asn Asp Phe
        180                 185                 190

Ala Lys Leu Phe Lys Gln Met Thr Glu Ala Trp Lys Lys Thr Tyr Gly
        195                 200                 205

Glu Val Val Asn Ser Phe Asn Glu Leu Glu Ser Asp Tyr Ala Asn His
    210                 215                 220

Tyr Lys Asn Val Ile Gly Arg Lys Ala Trp Glu Ile Gly Pro Leu Leu
225                 230                 235                 240

Leu Cys Ser Ser Ser Lys Gly Gly Glu Lys Asn Gln Gln Arg Gly Lys
                245                 250                 255

Glu Ser Ala Ile Asp Glu His Glu Cys Leu Ala Trp Leu Asp Ser Lys
            260                 265                 270

Asn Pro Asn Ser Val Val Tyr Val Cys Ala Gly Ser Val Ala Ser Phe
        275                 280                 285

Ser Gln Ala Gln Leu Arg Glu Thr Ala Met Gly Leu Glu Ala Ser Gly
        290                 295                 300

Gln Asn Phe Val Trp Val Val Arg Lys Asn Lys Glu Asp Asp Asp
305                 310                 315                 320

Trp Leu Pro Val Gly Phe Glu Glu Arg Val Gly Asn Arg Gly Leu Ile
                325                 330                 335

Ile Arg Gly Trp Ala Pro Gln Val Met Ile Leu Asn His Ala Ala Val
            340                 345                 350

Gly Ala Phe Val Thr His Cys Gly Trp Asn Ser Thr Leu Glu Gly Val
        355                 360                 365

Cys Ala Gly Leu Pro Met Val Thr Trp Pro Val Phe Ala Glu Gln Phe
        370                 375                 380

Phe Asn Glu Lys Leu Val Thr Glu Val Leu Gly Thr Gly Val Ser Val
385                 390                 395                 400

Gly Asn Lys Arg Trp Met Leu Arg Glu Ser Glu Gly Val Glu Arg Asp
                405                 410                 415

Ala Val Ala Arg Ala Val Glu Gly Ile Met Val Gly Gly Gly Ala Glu
            420                 425                 430

Glu Met Arg Ser Arg Ala Glu Asn Tyr Lys Glu Met Ala Lys Lys Ala
        435                 440                 445

Val Glu Glu Gly Gly Ser Ser Tyr Asn Asn Leu Asn Ala Leu Ile Glu
        450                 455                 460

Glu Leu Ser Asn Tyr Val Ala Pro Thr Ile Gln Asp Lys Asn
465                 470                 475

<210> SEQ ID NO 14
<211> LENGTH: 475
<212> TYPE: PRT
<213> ORGANISM: Dianthus caryophyllus

<400> SEQUENCE: 14

Met Gly Ser Glu His Gln Gln Leu His Val Ala Phe Phe Pro Phe Met
1               5                   10                  15

Ala His Gly His Met Ile Pro Thr Phe Asp Leu Ala Lys Leu Phe Ala
            20                  25                  30

Gly Arg Asp Val Lys Thr Thr Ile Thr Thr Pro Met Asn Ala His
        35                  40                  45

Ala Phe Ala Lys Thr Asn Val Pro Met Asn Leu Glu Ile Phe Thr Phe
    50                  55                  60
```

-continued

```
Pro Ala Gln Glu Ala Gly Leu Pro Glu Asn Cys Glu Asn Leu Glu Gln
 65                  70                  75                  80

Ala Met Ser Ile Gly Leu Leu Pro Ala Phe Ile Lys Ala Ser Ala Met
                 85                  90                  95

Leu Cys Asp Gln Leu Glu Arg Phe Leu Glu Arg Ser Gln Pro Asn Cys
                100                 105                 110

Leu Val Ala Asp Met Phe Phe Pro Trp Ala Thr Glu Ser Ala Arg Lys
                115                 120                 125

Phe Asn Val Pro Arg Ile Val Phe His Gly Thr Gly Phe Leu Ser Leu
                130                 135                 140

Cys Ala Lys Glu Val Glu Arg Leu Tyr Arg Pro Phe Lys Asn Val Ser
145                 150                 155                 160

Ser Asp Asp Glu Val Val Leu Pro Arg Leu Pro His Glu Val Lys
                    165                 170                 175

Leu Thr Arg Thr Gln Val Ser Glu Glu Trp Ser Asp Asp Asn
                180                 185                 190

Glu Phe Asn Lys Arg Ser Ala Arg Ile Lys Glu Ser Glu Val Glu Ser
                195                 200                 205

Tyr Gly Val Ile Val Asn Ser Phe Tyr Glu Leu Glu Pro Glu Phe Ala
                210                 215                 220

Asp Phe Arg Asn Glu Leu Gly Arg Arg Ala Trp Asn Val Gly Pro
225                 230                 235                 240

Val Ser Leu Cys Asn Arg Lys Thr Glu Asp Lys Ala Arg Arg Gly Lys
                245                 250                 255

Gln Ala Asn Val Asn Glu Gln Glu Cys Leu Ile Trp Leu Asp Ser Lys
                260                 265                 270

Lys Cys Ala Ser Val Val Tyr Val Cys Phe Gly Ser Thr Ala His Tyr
                275                 280                 285

Ala Pro Ala Gln Leu His Glu Ile Ala Asn Ala Leu Glu Ala Ser Gly
                290                 295                 300

His Asn Phe Val Trp Ala Val Gly Asn Val Asp Lys Gly Ser Asp Gly
305                 310                 315                 320

Glu Glu Leu Leu Pro Gln Gly Phe Glu Gln Arg Thr Glu Gly Arg Gly
                325                 330                 335

Leu Ile Ile Arg Gly Trp Ala Pro Gln Val Leu Ile Leu Glu His Glu
                340                 345                 350

Ala Val Gly Ala Phe Met Thr His Cys Gly Trp Asn Ser Thr Leu Glu
                355                 360                 365

Gly Ile Ser Ala Gly Val Pro Met Val Thr Trp Pro Val Phe Ala Glu
                370                 375                 380

Gln Phe Tyr Asn Glu Lys Leu Val Thr Gln Ile Leu Lys Ile Arg Val
385                 390                 395                 400

Glu Val Gly Ala Lys Lys Trp Ser Arg Thr Ala Met Ile Glu His Lys
                405                 410                 415

Ile Ser Gly Asp Ala Ile Glu Lys Ala Leu Lys Glu Ile Met Glu Gly
                420                 425                 430

Glu Lys Ala Glu Glu Met Arg Asn Lys Ala Arg Gln Leu Lys Glu Met
                435                 440                 445

Ala Trp Lys Ala Val Glu Glu Gly Gly Ser Ser Tyr Asn Asp Leu Thr
                450                 455                 460

Ala Leu Ile Ser Glu Leu Arg Asn Tyr Lys Ala
465                 470                 475
```

<210> SEQ ID NO 15
<211> LENGTH: 476
<212> TYPE: PRT
<213> ORGANISM: Scutellaria barbata

<400> SEQUENCE: 15

```
Met Gly Gln Leu His Ile Val Leu Val Pro Met Ile Ala His Gly His
1               5                   10                  15

Met Ile Pro Met Leu Asp Met Ala Lys Leu Phe Ser Ser Arg Gly Val
            20                  25                  30

Lys Thr Thr Ile Ile Ala Thr Pro Ala Phe Ala Glu Pro Ile Arg Lys
        35                  40                  45

Ala Arg Glu Ser Gly His Asp Ile Gly Leu Thr Thr Thr Lys Phe Pro
50                  55                  60

Pro Lys Gly Ser Ser Leu Pro Asp Asn Ile Arg Ser Leu Asp Gln Val
65                  70                  75                  80

Thr Asp Asp Leu Leu Pro His Phe Phe Arg Ala Leu Glu Leu Leu Gln
                85                  90                  95

Glu Pro Val Glu Glu Ile Met Glu Asp Leu Lys Pro Asp Cys Leu Val
            100                 105                 110

Ser Asp Met Phe Leu Pro Trp Thr Thr Asp Ser Ala Ala Lys Phe Gly
        115                 120                 125

Ile Pro Arg Leu Leu Phe His Gly Thr Ser Leu Phe Ala Arg Cys Phe
130                 135                 140

Ala Glu Gln Met Ser Ile Gln Lys Pro Tyr Lys Asn Val Ser Ser Asp
145                 150                 155                 160

Ser Glu Pro Phe Val Leu Arg Gly Leu Pro His Glu Val Ser Phe Val
                165                 170                 175

Arg Thr Gln Ile Pro Asp Tyr Glu Leu Gln Glu Gly Gly Asp Asp Ala
            180                 185                 190

Phe Ser Lys Met Ala Lys Gln Met Arg Asp Ala Asp Lys Lys Ser Tyr
        195                 200                 205

Gly Asp Val Ile Asn Ser Phe Glu Glu Leu Glu Ser Glu Tyr Ala Asp
210                 215                 220

Tyr Asn Lys Asn Val Phe Gly Lys Lys Ala Trp His Ile Gly Pro Leu
225                 230                 235                 240

Lys Leu Phe Asn Asn Arg Ala Glu Gln Lys Ser Ser Gln Arg Gly Lys
                245                 250                 255

Glu Ser Ala Ile Asp Asp His Glu Cys Leu Ala Trp Leu Asn Ser Lys
            260                 265                 270

Lys Pro Asn Ser Val Val Tyr Met Cys Phe Gly Ser Met Ala Thr Phe
        275                 280                 285

Thr Pro Ala Gln Leu His Glu Thr Ala Val Gly Leu Glu Ser Ser Gly
290                 295                 300

Gln Asp Phe Ile Trp Val Val Arg Asn Gly Gly Glu Asn Glu Asp Trp
305                 310                 315                 320

Leu Pro Gln Gly Phe Glu Glu Arg Ile Lys Gly Lys Gly Leu Met Ile
                325                 330                 335

Arg Gly Trp Ala Pro Gln Val Met Ile Leu Asp His Pro Ser Thr Gly
            340                 345                 350

Ala Phe Val Thr His Cys Gly Trp Asn Ser Thr Leu Glu Gly Ile Cys
        355                 360                 365

Ala Gly Leu Pro Met Val Thr Trp Pro Val Phe Ala Glu Gln Phe Tyr
370                 375                 380
```

-continued

```
Asn Glu Lys Leu Val Thr Glu Val Leu Lys Thr Gly Val Ser Val Gly
385                 390                 395                 400

Asn Lys Lys Trp Gln Arg Val Gly Glu Gly Val Gly Ser Glu Ala Val
            405                 410                 415

Lys Glu Ala Val Glu Arg Val Met Val Gly Asp Gly Ala Ala Glu Met
        420                 425                 430

Arg Ser Arg Ala Leu Tyr Tyr Lys Glu Met Ala Arg Lys Ala Val Glu
    435                 440                 445

Glu Gly Gly Ser Ser Tyr Asn Asn Leu Asn Ala Leu Ile Glu Glu Leu
    450                 455                 460

Ser Ala Tyr Val Pro Pro Met Lys Gln Gly Leu Asn
465                 470                 475
```

GLYCOSYLTRANSFERASE GENE AND USE THEREOF

CROSS REFERENCE TO RELATED APPLICATIONS

This application is the National Stage of International Application No. PCT/JP2012/050379, filed Jan. 11, 2012, and claims benefit of Japanese Application No. 2011-006317, filed on Jan. 14, 2011, all of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Oct. 2, 2013, is named 047237-5033-00-US-501115 SL.txt and is 81,965 bytes in size.

TECHNICAL FIELD

The present invention relates to a polynucleotide which encodes a protein having an activity of transferring a glycosyl to both of the hydroxyl groups at the 4'- and 7-positions of a flavone, as well as uses thereof.

BACKGROUND ART

In the flower industry, flowers having a new trait are always highly valued. In particular, the development of plants having a different "color", the most important trait of flowers, is industrially very important, and so far flowers of a variety of colors have been developed by cultivar improvement using classical breeding methods. With these methods are effective in cultivar improvement, there are restrictions on the gene pool inherent to each plant, and thus the methods can be applied to gene resources owned by closely related species that are amenable to breeding. For example, despite long years of breeding efforts, no purple to blue varieties for roses, carnations, chrysanthemums or lilies, no bright red varieties for gentians or irises, and no yellow varieties for geranium or morning glories have been created.

Flower color results from four types of pigments, i.e., flavonoids, carotenoids, chlorophylls, and betalains. Among them, flavonoids contribute to a variety of colors such as yellow, red, purple and blue. The group of pigments that develop red, purple and blue colors is collectively termed anthocyanins, and the diversity of anthocyanin structures is one reason for the wide variety of flower colors. Considering the biosynthetic pathway, anthocyanins are roughly divided into three groups depending on the aglycon structure. Bright red-colored flowers such as carnation and geranium often contain pelargonidin-type anthocyanins, and blue- and purple-colored flowers often contain delphinidin-type anthocyanins. The absence of blue or purple varieties of roses, carnations, chrysanthemums and lilies is because they have no ability of synthesizing the delphinidin-type anthocyanins.

In order for flowers to have a blue color, in addition to the accumulation of delphinidins, it has been thought that either one of the following is required: (i) the modification of anthocyanins with one or a plurality of aromatic acyl group(s), (ii) coexistence of anthocyanins with copigments such as flavones and flavonols, (iii) coexistence of anthocyanins with iron ions or aluminum ions, (iv) the increase in pH of anthocyanin-localized vacuoles from neutral to weak alkali, and (v) complex formation by anthocyanins, copigments and metal ions (such anthocyanins are termed metalloanthocyanins) (Non-patent document 1 below).

Biosynthesis of flavonoids and anthocyanins has been well studied, and relevant biosynthetic enzymes and genes encoding them have been identified (see Non-patent document 2, FIG. 1 below). For example, genes of flavonoid 3',5'-hydroxylase (F3'5'H), which hydroxylates the B ring of flavonoids required in delphinidin biosynthesis, have been obtained from many plants. Also, by introducing these F3'5'H genes into carnations (see Patent document 1 below), roses (see Non-patent document 3 and Patent documents 2 and 3 below), and chrysanthemums (see Patent document 4 below), gene recombinant plants in which delphinidins are accumulated in petals and flower color is changed to blue have been generated (see Non-patent document 4 below). Such carnations and roses are commercially available.

Flavones, a family of organic compounds, are cyclic ketones of flavane derivatives. In a narrower sense, it indicates 2,3-didehydroflavan-4-one, a compound having a chemical formula $C_{15}H_{10}O_2$ and a molecular weight of 222.24. In a broader sense, derivatives belonging to flavanes are termed "flavone". Flavonesas defined in the broader sense (flavones) constitute one category of flavonoids. Those flavonoids that have the flavone structure as the basic skeleton and have no hydroxyl groups at the 3-position are classified into "flavones". Representative examples of "flavones" include apigenin (4',5,7-trihydroxyflavone) and luteolin (3',4',5,7-tetrahydroxyflavone). As used herein the term "flavone" refers to a flavone as defined in the broader sense, i.e., a derivative belonging to flavone.

Genes of flavone synthase (FNS) required for flavone biosynthesis have also been obtained from many plants. Flavone, when coexistent with anthocyanin, is known to have an effect of making the color of anthocyanin bluer, and these FNS genes attracted attention in the modification of flower colors. By introducing the FNS gene together with F3'5'H into roses having no ability of synthesizing flavones, the flower petals accumulated delphinidin simultaneously with the accumulation of flavone, making flower color bluer (see Patent document 5 below). Since flavone absorbsan ultraviolet ray in addition to making flower color bluer, it protects plants against the ultraviolet ray or serves as a signal to vision of insects in insect-pollinated flowers. Flavone is also involved in interaction with soil microorganisms. Furthermore, flavone is used in materials for foods or cosmetics as ingredients good for health. For example, flavone is said to have an anti-cancer effect, and it has also been demonstrated that by taking flavone-rich food materials, cancer can be treated or prevented.

Genes that modify anthocyanin and flavone have also been obtained from many plants. There are glycosyltransferase, acyl transferase, methyl transferase etc., and, among them, glycosyltransferase (GT) that catalyzes glycosylation is described herein. For example, genes encoding a protein having an activity of transferring glucose to the hydroxyl group at the 3-position of anthocyanin have been isolated from gentian, *perilla, petunia*, rose, *antirrhinum* and the like (see Non-patent documents 4 to 6 and Patent Document 6). Genes encoding a protein having an activity of transferring glucose to a hydroxyl group at the 5-position of anthocyanin have been isolated from *perilla, petunia*, rose, gentian, *verbena, torenia* and the like (see Non-patent documents 5 to 7, and Patent document 7 below). A gene encoding a protein having an activity of transferring glucose to the hydroxyl group at the 7-position of flavone has been isolated from *arabidopsis* (see Non-patent document 8 below). A gene encoding a protein having an activity of transferring glucose to the hydroxyl group at the 7-position of baicalin has been isolated from Scutellaria baicalensis, and it is also reported that a protein obtained by expressing the gene in Escherichia coli catalyzes a reaction that exhibits an activity of transferring glucose to the hydroxyl group at the 7-position of flavonoid (see Non-patent document 9 below). A gene encoding a protein having an activity of transferring glucose to the hydroxyl group at the 3'-position of anthocyanin has been isolated from gentian, butterfly pea, and cineraria (see Patent document 8 below). Also, a gene encoding a protein having an activity of transferring glucose to hydroxyl groups at two different positions on the A and C rings of anthocyanin has been isolated from rose (see Patent document 9 below). A gene encoding a protein having an activity of transferring glucose to hydroxyl groups at two different positions of the B ring of anthocyanin has been isolated from butterfly pea (see Patent document 10 below).

While the glycosyltransferases mentioned above rely on UDP-glucose as a glycosyl donor, a glycosyltransferase whose glycosyl donor is acyl glucose has been identified recently. A gene encoding a protein having an activity of transferring glucose to the hydroxyl group at the 5-position of anthocyanin-3 glucoside has been isolated from carnation, and a gene encoding a protein having an activity of transferring glucose to a hydroxyl group at the 7-position has been isolated from delphinium (see, Non-patent document 10 below).

Thus, a multitude of proteins having an activity of transferring glucose to various hydroxyl groups are known as glycosyltransferases.

However, it is believed that there are still many glycosyltransferases of which functions have not been identified. For example, a gene encoding a protein having an activity of transferring a glycosyl to the 4'-position of a flavonoid, or a gene encoding a protein having an activity of transferring glycosyl sequentially to hydroxyl groups at two sites on the A and B rings of a flavonoid has not been identified yet. It is reported that a protein obtained by expressing a glycosyltransferase gene derived from Livingstone daisy in Escherichia coli exhibits an activity of transferring glucose to either one of the hydroxyl groups at the 4'-position and the 7-position of a flavonoid, but the original activity of the glycosyltransferase in plants is to transfer glucose to the hydroxyl group at the 5-position of betanidine (see Non-patent document 11 below).

A metalloanthocyanins, which is represented by pigments of Commelina, Centaurea, Salvia, and Nemophila, is composed of six molecules of anthocyanin, six molecules of flavone, and two metal atoms, which components aggregate to form a stable blue pigment (see FIG. 2, Non-patent document 1). For example, anthocyanin of Nemophila is composed of nemophilin (see FIG. 3), malonyl apigenin 4',7-diglucoside (see FIG. 4), $Mg^{2+}$ and $Fe^{3+}$. Metalloanthocyanin of Salvia is composed of cyanosalvianin (see FIG. 5), and apigenin 4',7-diglucoside (see FIG. 6) and $Mg^{2+}$. Studies so far have demonstrated that in all blue flowers forming metalloanthocyanins, flavone in which a glycosyl has been added to both of the hydroxyl groups at the 4'-position and the 7-position, and the glycosyl added to the flavone has been shown to play an important role in molecular recognition in metalloanthocyanin formation. The glycosyl coordinated at the 4'-position of a flavone is important in molecular recognition during the formation, and the glycosyl at the 7-position has been indicated to contribute to its stability (see Non-patent document 1 below). Only after the addition of these two glycosyls, metalloanthocyanin is formed thereby expressing a beautiful blue color. In Dutch iris petals, flavone in which a glycosyl has been added to the 4'-position is contained. Since the addition of two glycosyls to a flavone leads to increased solubility and altered properties, the expansion of uses as materials for health food products, pharmaceutical products and cosmetic products can be expected.

CITATION LIST

Patent Documents

Patent document 1: WO2006/105598A
Patent document 2: WO2010/122849A
Patent document 3: WO2005/017147A
Patent document 4: WO2009/062253A
Patent document 5: WO2008/156211A
Patent document 6: WO2007/094521A
Patent document 7: WO99/05287A
Patent document 8: WO01/092509A
Patent document 9: JP2006-149293A
Patent document 10: JP2005-095005A Non-Patent Documents Non-patent document 1: Natural Product Reports (2009), 26, 884-915
Non-patent document 2: Bioscience, Biotechnology, and Biochemistry (2010), 74(9), 1760-1769
Non-patent document 3: Plant Cell Physiology (2007), 48(11), 1589-1600
Non-patent document 4: Plant Cell Physiology (1996), 37(5), 711-716
Non-patent document 5: The Journal of Biological Chemistry (1999), 274(11), 7405-7411
Non-patent document 6: Plant Molecular Biology (2002), 48, 401-411
Non-patent document 7: Journal of Experimental Botany (2008), 59(6), 1241-1252
Non-patent document 8: Bioscience, Biotechnology, and Biochemistry (2006), 70(6), 1471-1477
Non-patent document 9: Planta (2000), 210, 1006-1013
Non-patent document 10: Plant Cell (2010), 22(10), 3374-89
Non-patent document 11: The Plant Journal (1999), 19(5), 509-519

SUMMARY OF INVENTION

Problems to be Solved by the Invention

Changing the properties of flavone is necessary to change flower colors and to develop materials for food products, pharmaceutical products and cosmetic products. For example, while the color of carnation, rose and chrysanthemum in which delphinidin is accumulated is blue purple, research is going on to make the color further bluer.

Under such circumstances, the problem the present invention intends to solve is to provide a polynucleotide encoding a protein having an activity of transferring a glycosyl to both of the hydroxyl groups at the 4'-position and 7-position of a flavone, and use thereof.

Means to Solve the Problems

After intensive and extensive research to solve the above problem, the applicants of the present application have confirmed that a polynucleotide encoding a protein having an activity of transferring a glycosyl to both of the hydroxyl groups at the 4'-position and 7-position of a flavone can be isolated and used, and therefore have completed the present invention.

Thus, the present invention is as follows:

[1] A polynucleotide selected from the group consisting of:
(a) a polynucleotide comprising a base sequence defined in SEQ ID NO: 1, 3 or 12;
(b) a polynucleotide which hybridizes with a polynucleotide comprising a base sequence complementary to a base sequence defined in SEQ ID NO: 1, 3 or 12 under a stringent condition and encodes a protein having an activity of transferring a glycosyl to both of the hydroxyl groups at the 4'- and 7-positions of a flavone;
(c) a polynucleotide which encodes a protein comprising an amino acid sequence defined in SEQ ID NO: 2, 4 or 13;
(d) a polynucleotide which encodes a protein comprising an amino acid sequence in which one or several amino acids have been deleted, substituted, inserted, and/or added in an amino acid sequence defined in SEQ ID NO: 2, 4 or 13 and having an activity of transferring a glycosyl to both of the hydroxyl groups at the 4'- and 7-positions of a flavone; and
(e) a polynucleotide which encodes a protein having an amino acid sequence which has an identity of 90% or more to an amino acid sequence defined in SEQ ID NO: 2, 4 or 13 and having an activity of transferring a glycosyl to both of the hydroxyl groups at the 4'- and 7-positions of a flavone.
[2] The polynucleotide according to the above [1], which is (a) a polynucleotide comprising a base sequence defined in SEQ ID NO: 1, 3 or 12.
[3] The polynucleotide according to the above [1], which is (c) a polynucleotide which encodes a protein comprising an amino acid sequence defined in SEQ ID NO: 2, 4 or 13.
[4] The polynucleotide according to the above [1], which is (f) a polynucleotide which encodes a protein having an amino acid sequence which has an identity of 95% or more to an amino acid sequence defined in SEQ ID NO: 2, 4 or 13 and having an activity of transferring a glycosyl to both of the hydroxyl groups at the 4'- and 7-positions of a flavone.
[5] The polynucleotide according to the above [4], which is (g) a polynucleotide which encodes a protein having an amino acid sequence which has an identity of 97% or more to an amino acid sequence defined in SEQ ID NO: 2, 4 or 13 and having an activity of transferring a glycosyl to both of the hydroxyl groups at the 4'- and 7-positions of a flavone.
[6] The polynucleotide according to the above [5], which is (h) a polynucleotide which encodes a protein having an amino acid sequence which has an identity of 98% or more to an amino acid sequence defined in SEQ ID NO: 2, 4 or 13 and having an activity of transferring a glycosyl to both of the hydroxyl groups at the 4'- and 7-positions of a flavone.
[7] The polynucleotide according to any one of the above [1] to [6], which is DNA.
[8] A protein encoded by the polynucleotide according to any one of the above [1] to [7].
[9] A vector comprising the polynucleotide according to any one of the above [1] to [7].
[10] A non-human host according to the above [9] into which the vector according to the above [9] has been introduced.
[11] A method of adding a glycosyl to both of the hydroxyl groups at the 4'- and 7-positions of a flavone using the polynucleotide according to any one of the above [1] to [7].
[12] A plant or a progeny thereof, or a part or tissue thereof, into which the polynucleotide according to any one of the above [1] to [7] has been introduced and which contains the polynucleotide.
[13] The part of a plant according to the above [12], which is a cut flower.
[14] A cut flower artifact using the cut flower according to the above [13].
[15] A process of producing a protein having an activity of transferring a glycosyl to both of the hydroxyl groups at the 4'- and 7-positions of a flavone, comprising the steps of:
culturing or growing the non-human host according to the above [10]; and
collecting a protein having an activity of transferring a glycosyl to both of the hydroxyl groups at the 4'- and 7-positions of a flavone from the non-human host.
[16] A process of producing a flavone in which a glycosyl has been added to both of the hydroxyl groups at 4'- and 7-positions thereof, comprising the steps of:
culturing or growing the non-human host according to the above [10]; and
collecting a flavone in which a glycosyl has been added to both of the hydroxyl groups at 4'- and 7-positions thereof from the non-human host.
[17] A food product comprising a flavone which has been produced by the process according to the above [16] and in which a glycosyl has been added to both of the hydroxyl groups at 4'- and 7-positions thereof.
[18] A pharmaceutical product comprising a flavone which has been produced by the process according to the above [16] and in which a glycosyl has been added to both of the hydroxyl groups at 4'- and 7-positions thereof.
[19] A cosmetic product comprising a flavone which has been produced by the process according to the above [16] and in which a glycosyl has been added to both of the hydroxyl groups at 4'- and 7-positions thereof.

Effects of the Invention

By expressing the polynucleotide of the present invention in a suitable host cell, a protein having an activity of specifically transferring a glycosyl to both of the hydroxyl groups at the 4'- and 7-positions of a flavone can be produced. In accordance with the present invention, a protein having an activity of specifically transferring a glycosyl to both of the hydroxyl groups at the 4'- and 7-positions of a flavone can be used in altering flower color by expressing it in a constitutive and tissue-specific manner in plants. Also, in accordance with the present invention, there are provided a method for producing a flavone in which a glycosyl has been added to both of the hydroxyl groups at 4'- and 7-positions thereof, and foods, pharmaceuticals, and cosmetics obtained by the production method.

Figure 1:
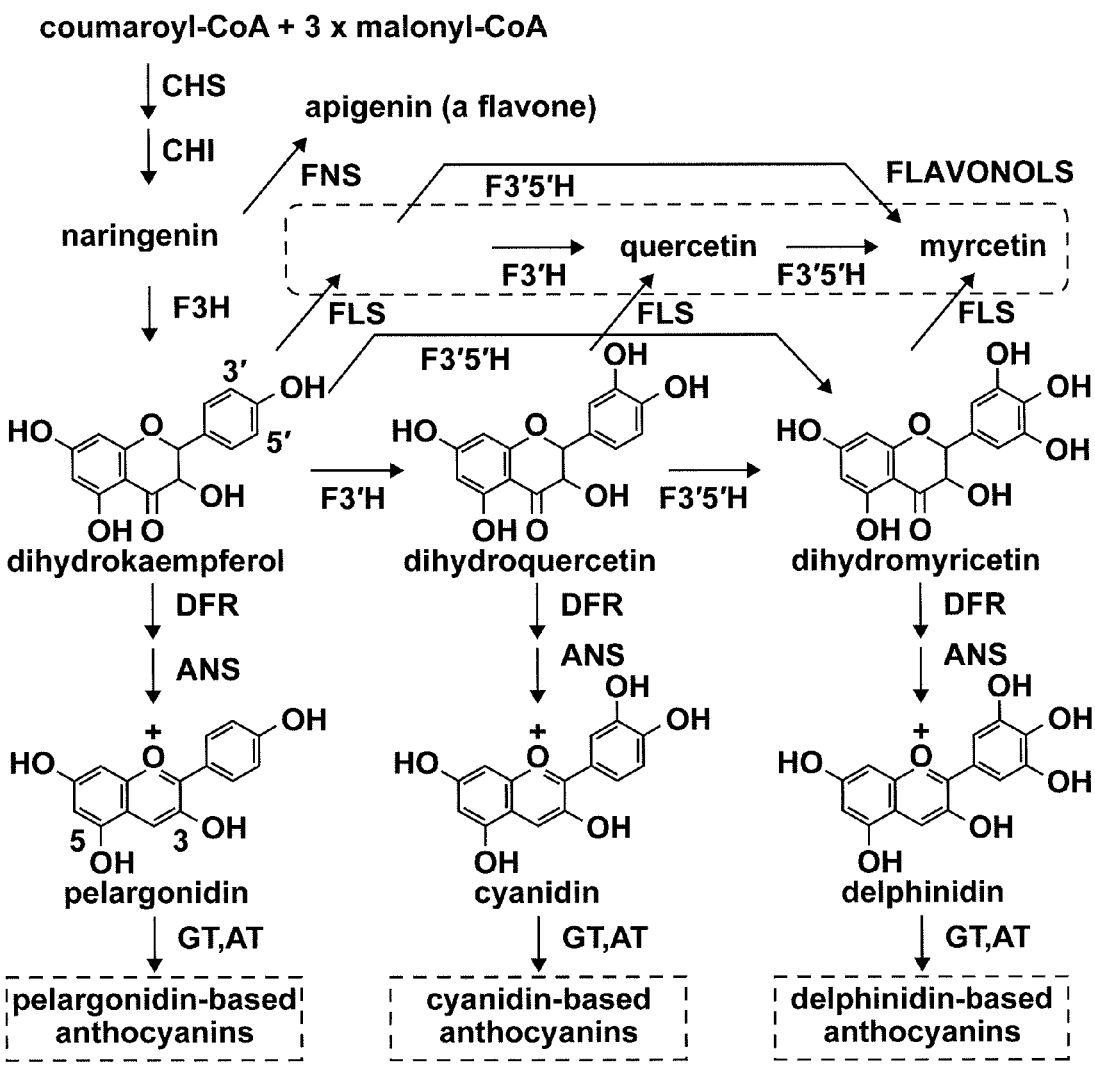
FIG. 1
A drawing that explains the biosynthetic pathway of anthocyanin.
Figure 2:
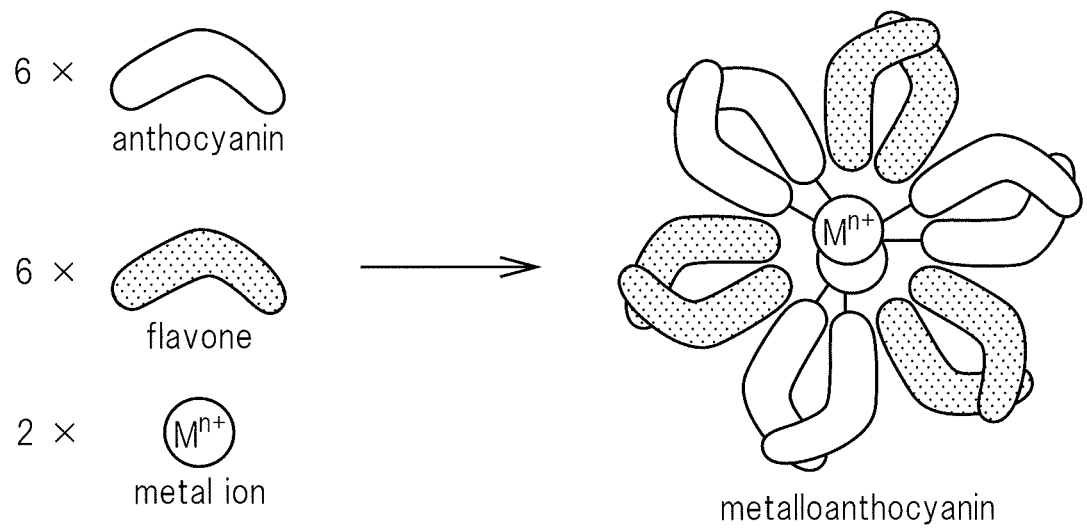
FIG. 2
A schematic diagram of the structure of metalloanthocyanin.
Figure 3:
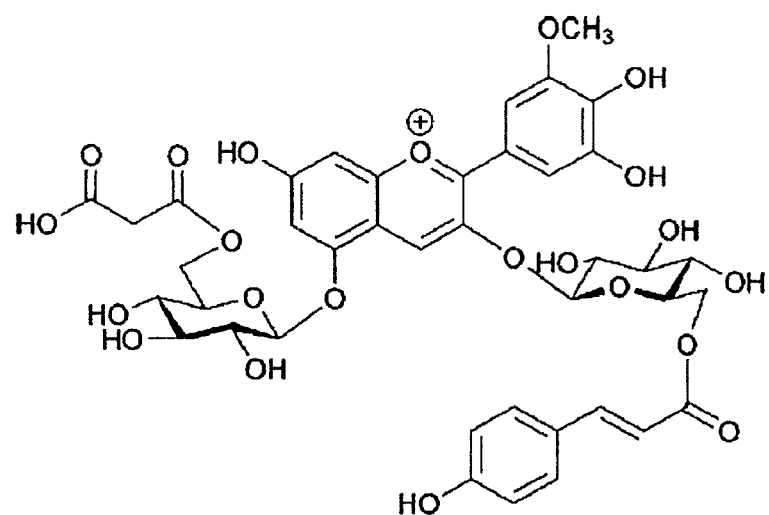
FIG. 3
A structural formula of an anthocyanin (nemophilin) derived from *Nemophila*.
Figure 4:
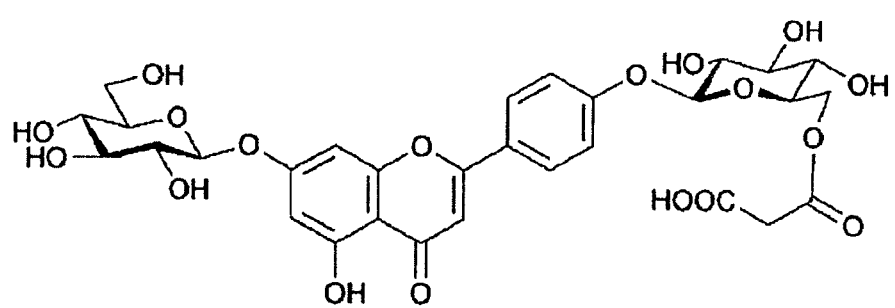
FIG. 4
A structural formula of a flavone (malonyl apigenin 4',7-diglucoside) derived from *Nemophila*.
Figure 5:
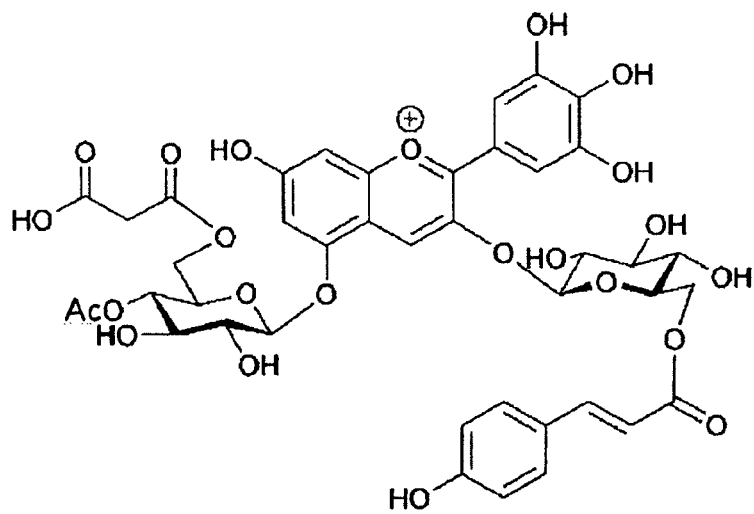
FIG. 5
A structural formula of an anthocyanin (cyanosalvianin) derived from *Salvia*.

A structural formula of a flavone (apigenin 4',7-diglucoside) derived from *Salvia*.

FIG. 7

A high performance liquid chromatogram of a reaction mixture in which a petal extract and apigenin were enzymatically reacted.

FIG. 8

A drawing that explains the biosynthetic pathway of apigenin 4',7-diglucoside.

FIG. 9

A high performance liquid chromatogram of a reaction mixture in which an NmGT3 protein solution and apigenin were enzymatically reacted.

FIG. 10

A high performance liquid chromatogram of a reaction mixture in which an NmGT4 protein solution and apigenin were enzymatically reacted,

FIG. 11

A high performance liquid chromatogram of a reaction mixture in which an NmGT3 protein solution and apigenin 7-glucoside were enzymatically reacted.

FIG. 12

A high performance liquid chromatogram of a reaction mixture in which an NmGT4 protein solution and apigenin 7-glucoside were enzymatically reacted.

FIG. 13

A drawing that summarizes the reactivity of an enzyme that adds a glycosyl to the 5-gene therapy of the NmGT3 protein, the NmGT4 protein, the SuGT5 protein, and baicalin for various flavonoids.

FIG. 14

An alignment diagram that compares the amino acid sequences of NmGT3 (SEQ ID NO: 2) and NmGT4 (SEQ ID NO: 4) (an identity of 31%, an identity on the nucleic acid level of 51%).

FIG. 15

An alignment diagram that compares the amino acid sequences of NmGT3 (SEQ ID NO: 2) and an enzyme that adds a glycosyl to the 2'-position of chalcononaringenin (SEQ ID NO: 14) (an identity of 32%, an identity on the nucleic acid level of 47%).

FIG. 16

An alignment diagram that compares the amino acid sequences of NmGT4 (SEQ ID NO: 4) and an enzyme that adds a glycosyl to the 7-position of flavonoid (SEQ ID NO: 15) (an identity of 52%, an identity on the nucleic acid level of 60%).

FIG. 17

A construct (pSPB4584 through 4587) comprising NmGT3 and NmGT4 introduced into a *torenia*.

FIG. 18

A construct (pSPB5414 and 5427) comprising NmGT3 and NmGT4 introduced into a *petunia*.

FIG. 19

A construct (pSPB5433) comprising NmGT3 introduced into a carnation.

FIG. 20

A construct (pSPB4581, 4582, 5437, and 5440) comprising NmGT3 introduced into a rose.

FIG. 21

A high performance liquid chromatogram of a reaction mixture in which a SuGT5 protein solution and apigenin were enzymatically reacted.

FIG. 22

A high performance liquid chromatogram of a reaction mixture in which a SuGT5 protein solution and apigenin 7-glucoside were enzymatically reacted.

FIG. 23

An alignment diagram that compares the amino acid sequences of SuGT5 (SEQ ID NO: 13) and NmGT3 (SEQ ID NO: 2) (an identity of 38%, an identity on the nucleic acid level of 47%).

FIG. 24

An alignment diagram that compares the amino acid sequences of SuGT5 (SEQ ID NO: 13) and NmGT4 (SEQ ID NO: 4) (an identity of 51%, an identity on the nucleic acid level of 58%).

DESCRIPTION OF EMBODIMENTS

The present invention relates to a polynucleotide selected from the group consisting of:

(a) a polynucleotide comprising a base sequence defined in SEQ ID NO: 1, 3 or 12;

(b) a polynucleotide which hybridizes with a polynucleotide comprising a base sequence complementary to a base sequence defined in SEQ ID NO: 1, 3 or 12 under a stringent condition and encodes a protein having an activity of transferring a glycosyl to both of the hydroxyl groups at the 4'- and 7-positions of a flavone;

(c) a polynucleotide which encodes a protein comprising an amino acid sequence defined in SEQ ID NO: 2, 4 or 13;

(d) a polynucleotide which encodes a protein comprising an amino acid sequence in which one or several amino acids have been deleted, substituted, inserted, and/or added in an amino acid sequence defined in SEQ ID NO: 2, 4 or 13 and having an activity of transferring a glycosyl to both of the hydroxyl groups at the 4'- and 7-positions of a flavone; and (e) a polynucleotide which encodes a protein having an amino acid sequence which has an identity of 90% or more to an amino acid sequence defined in SEQ ID NO: 2, 4 or 13 and having an activity of transferring a glycosyl to both of the hydroxyl groups at the 4'- and 7-positions of a flavone.

As used herein the term "polynucleotide" means DNA or RNA.

As used herein the term "stringent condition" means a condition that permits a selective and detectable specific bonding between a polynucleotide or an oligonucleotide and genomic DNA. The stringent condition may be defined by the suitable combination of salt concentration, organic solvent (e.g., formamide), temperature, and other known conditions. Thus, by reducing the salt concentration, increasing the organic solvent concentration, or increasing the hybridization temperature, stringency can be increased. Furthermore, the washing condition after hybridization can also affect stringency. The washing condition also can be defined by salt concentration and temperature, and by reducing the salt concentration and increasing the temperature, the stringency of washing can be increased. Thus, the term "stringent condition" means a condition under which specific hybridization only occurs between highly homologous base sequences as in cases where the degree of "identity" or "homology" between the base sequences is on the average about 80% or more, preferably about 90% or more, more preferably about 95% or more, still more preferably 97% or more, and most preferably 98% or more. As a "stringent condition", for example, there can be mentioned conditions in which, at a temperature of 60° C. to 68° C., the sodium concentration is 150 to 900 mM, preferably 600 to 900 mM, and pH 6 to 8. As a specific example, there can be mentioned a case wherein hybridization is performed at a condition of 5×SSC (750 mM NaCl, 75 mM trisodium citrate), 1% SDS, 5×Denhardt's solution, 50% formaldehyde, and 42° C., followed by washing at a condition of 0.1×SSC (15 mM NaCl, 1.5 mM trisodium citrate), 0.1% SDS and 55° C.

Hybridization may be performed according to, for example, a method described in Current Protocols in Molecular Biology (edited by Frederick M. Ausubel et al., 1987)), a method known in the art, or an equivalent method. When a commercially available library is used, hybridization may be performed according to a method described in the attached instruction for use. A gene selected for such hybridization may be of natural origin, such as derived from plants, or from other than plants. Also a gene selected by hybridization may be cDNA, genomic DNA, or a chemically synthesized DNA.

The statement "amino acid sequence in which one or several amino acids have been deleted, substituted, inserted, and/or added" above means an amino acid sequence in which 1 to 20, preferably 1 to 5, and more preferably 1 to 3 amino acids have been deleted, substituted, inserted, and/or added. Since site-directed mutagenesis, which is one of the gene engineering methods, can introduce specific mutation into a specific site, it is useful, and may be performed according to a method described in Molecular Cloning: A Laboratory Manual, 2nd Ed., Cold Spring Harbor Laboratory Press, Cold Spring Harbor, N.Y., 1989, etc. By allowing this mutated DNA to be expressed using a suitable expression system, a protein consisting of an amino acid sequence in which one or several amino acids have been deleted, substituted, inserted, and/or added can be obtained.

DNA according to the present invention can be obtained by any method known to a person skilled in the art, such as chemical synthesis using, e.g., a phosphoramidite method, or a nucleic acid amplification using a primer designed based on the nucleotide sequence of the gene of interest and also using a nucleic acid sample of a plant as a template.

As used herein the terms "identity" and "homology" mean that, in two chains of polypeptide sequences (or amino acid sequences) or of polynucleotide sequences (or base sequences), the quantities (numbers) of respective amino acid residues or respective bases constituting the chains are such that they may be determined to be identical in the compatibility of the two chains, and mean the degree of sequence correlation between two polypeptide sequences or two polynucleotide sequences. The "identity" and "homology" can be easily calculated. Many methods for determining homology between two polynucleotide sequences or polypeptide sequences are known, and the terms "identity" and "homology" are well known to a person skilled in the art (see, for example, Lesk, A. M. (Ed.), Computational Molecular Biology, Oxford University Press, New York, (1988); Smith, D. W. (Ed.), Biocomputing: Informatics and Genome Projects, Academic Press, New York, (1993); Grifin, A. M. & Grifin, H. G. (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991), etc.).

While, unless otherwise specified, the numerical values of "identity" and "homology" described herein may be values calculated using a homology search program known to a person skilled in the art, they may preferably be numerical values calculated using the Clustal W program of MacVector application (version 9.5, Oxford Molecular Ltd., Oxford, England).

The polynucleotide (nucleic acid, gene) of the present invention may "encode" a protein of interest. As used herein "encode" means that the protein of interest may be expressed in a form in which it retains the activity. Also "encode" has the meaning of both of encoding the protein of interest as a contiguous structural sequence (exon) or encoding it via intervening sequences (introns).

A gene having the original base sequence can be obtained using, for example, analysis with a DNA sequencer as described in the Examples below. DNA encoding an enzyme having a modified amino acid sequence can also be synthesized using a common site-directed mutagenesis or a PCR method based on the DNA having the original base sequence. For example, a DNA fragment desired to be modified may be obtained by restriction treatment of the original cDNA or genomic DNA, and with this fragment as the template, site-directed mutagenesis or a PCR reaction may be performed using primers in which the desired mutation has been introduced to obtain the desired modified DNA fragment. Thereafter, this mutation-introduced DNA fragment may be linked to a DNA fragment encoding the other part of the enzyme of interest.

Alternatively, in order to obtain a DNA encoding an enzyme comprising a shortened amino acid sequence, a DNA encoding an amino acid sequence longer than the amino acid sequence of interest, such as DNA encoding the full-length amino acid sequence, may be cleaved with the desired restriction enzyme, and when the resulting DNA fragment does not encode the entire amino acid sequence of interest, a DNA fragment comprising the sequence of the lacking part may be synthesized and linked.

Also, by expressing the polynucleotide obtained using an expression system in *Escherichia coli* and yeast and determining the enzyme activity, the polynucleotide obtained can be confirmed to encode a protein having an activity of transferring a glycosyl to both of the hydroxyl groups at the 4'-position and 7-position of a flavone. Furthermore, by expressing this polynucleotide, a polynucleotide product, a protein having an activity of transferring a glycosyl to both of the hydroxyl groups at the 4'-position and 7-position of a flavone, can be obtained. Alternatively, a protein having an activity of transferring a glycosyl to both of the hydroxyl groups at the 4'-position and 7-position of a flavone can also be obtained using an antibody against a polypeptide comprising an amino acid sequence described in SEQ ID NO: 2, 4 or 13, and, using such an antibody, a polynucleotide encoding a protein having an activity of transferring a glycosyl to both of the hydroxyl groups at the 4'-position and 7-position of a flavone derived from another organism can be cloned.

The present invention also relates to a (recombinant) vector, specifically an expression vector, comprising the above-mentioned polynucleotide, and furthermore to a host transformed with the vector.

As the host, a prokaryotic or a eukaryotic organism can be used. As the prokaryotic organism, bacteria, for example, commonly used hosts such as bacteria belonging to genus *Escherichia* such as *Escherichia coli* and bacteria belonging to genus *Bacillus* such as *Bacillus subtilis* can be used. As the eukaryotic organism, lower eukaryotic organisms such as eukaryotic microorganisms including, for example, yeast or fungi can be used.

Examples of yeast include microorganisms belonging to genus *Saccharomyces* such as *Saccharomyces cereviceae*, and examples of fungi include microorganisms belonging to genus *Aspergillus* such as *Aspergillus oryzae* and *Aspergillus niger*, and microorganisms belonging to genus *Penicillium*. Animal cells or plant cells also can be used as a host. Examples of animal cells that can be used include cell lines of mouse, hamster, monkey, human, etc., as well as insect cells such as silkworm cells and adult silkworm per se.

Depending on the type of a host into which the expression vector of the present invention is introduced, the vector may contain expression regulatory regions such as a promoter, a terminator, and an origin of replication. As the promoter for bacterial expression vectors, commonly used promoters such as the trc promoter, the tac promoter and the lac promoter may be used. As the promoter for yeasts, glyceraldehyde-3-phosphate dehydrogenase promoter, the PH05 promoter etc. may be used. As the promoter for fungi, the amylase promoter, the trpC promoter etc. may be used. As the promoter for animal cell hosts, viral promoters such as the SV40 early promoter, the SV40 late promoter etc. may be used. As examples of promoters for constitutively expressing a polynucleotide in plant cells, there can be mentioned, for example, the 35S RNA promoter of cauliflower mosaic virus, the rd29A gene promoter, the rbcS promoter, the mac-1 promoter, etc. Also, for tissue-specific gene expression, the promoter of the gene to be specifically expressed in the tissue can be used.

Construction of an expression vector may be performed using a restriction enzyme, ligase etc. according to a standard method. The transformation of a host with an expression vector can also be performed according to a standard method.

A protein of interest can be obtained by culturing, cultivating or growing a host transformed with the above expression vector, and then by recovering and/or purifying the culture or the culture medium according to a standard method, such as filtration, centrifugation, cell disruption, gel filtration chromatography, ion exchange chromatography and the like.

Herein, a gene encoding a protein having an activity of transferring a glycosyl to both of the hydroxyl groups at the 4'-position and 7-position of a flavone derived from *Nemophila* or *Salvia* may be mentioned, but the polynucleotide claimed in the present invention is not limited to gene derived from *Nemophila* or *Salvia*. The origin of the gene encoding a protein having an activity of transferring a glycosyl to both of the hydroxyl groups at the 4'-position and 7-position of a flavone may be a plant, an animal or a microorganism, and as long as it has an activity of transferring a glycosyl to both of the hydroxyl groups at the 4'-position and 7-position of a flavone, it can be used in changing flower colors of plants, regardless of the origin of the gene.

The present invention also relates to a plant or a progeny thereof, or a part or tissue thereof obtained by introducing an exogenous polynucleotide encoding a protein having an activity of transferring a glycosyl to both of the hydroxyl groups at the 4'-position and 7-position of a flavone into the plant, and by allowing it to be contained in said plant. The form of the above part or tissue may be a cut flower. By using a polynucleotide encoding a protein having an activity of transferring a glycosyl to both of the hydroxyl groups at the 4'-position and 7-position of a flavone, both of the 4'-position and 7-position of a flavone can be glycosylated or the glycosylation of both of the 4'-position and 7-position of a flavone can be suppressed, with a result that the flower color of the plant can be changed.

According to today's state of the art, a technology of introducing a polynucleotide into a plant and allowing the polynucleotide to be expressed in a constitutive or tissue-specific manner can be used. The introduction of DNA into a plant can be performed according to a method known to a person skilled in the art, such as an *Agrobacterium* method, a binary vector method, an electroporation method, a PEG method, a particle gun method and the like.

As examples of plants that can be transformed, there can be mentioned, but not limited to, rose, carnation, *chrysanthemum*, snapdragon, *cyclamen*, orchids, Turkey homecoming, *freesia*, *gerbera*, *gladiolus*, baby's breath, *kalanchoe*, lily, *Pelargonium*, *geranium*, *petunia*, *torenia*, tulip, *anthurium*, *phalaenopsis*, rice, barley, wheat, rapeseed, potato, tomato, poplar, banana, eucalyptus, sweet potato, soybean, Arufarusa, Rubin, corn, cauliflower, dahlia etc.

The present invention also relates to processed products (processed cut flowers) using the above-mentioned cut flowers. Here, the processed cut flowers include, but not limited to, pressed flowers, preserved flowers, dried flowers, resin-sealed flowers etc.

A flavone, produced by a production method of the present invention, having a glycosyl added to the 4'-position and 7-position thereof can be used in applications such as food products, pharmaceutical products, cosmetic products, and the like.

In accordance with the present invention, the expression of a gene of interest in a plant can also be suppressed by, e.g., an antisense method, a cosuppression method, or an RNAi method. The method of suppressing the expression of a gene of interest can be performed by a method known to a person skilled in the art, such as an antisense RNA/DNA technology [Biotechnology, 9, 358 (1992), Trends in Biotechnology, 10, 87 (1992), Trends in Biotechnology, 10, 152 (1992)], and a triple helix technology [Trends in Biotechnology, 10, 132 (1992)]. For example, the suppression of gene expression can be performed using a single stranded nucleic acid molecule comprising all or part of a nucleotide sequence identical with the antisense chain of the gene of the present invention. Such a method is known as an antisense method. In the antisense method, RNA having a sequence complementary to the gene of which expression is desired to be suppressed may be expressed at a high level in order to suppress the expression of the target gene. In this method, a single stranded RNA comprising all of a nucleotide sequence identical with the antisense chain of the polynucleotide (gene) of the present invention can be used. Also, in the above method, a single stranded RNA comprising a part of a nucleotide sequence identical with the antisense chain of the polynucleotide (gene) of the present invention can be used. Such a partial single stranded RNA may be any RNA that can suppress the expression of the gene of the present invention. While it can be designed as appropriate by a person skilled in the art, it may preferably be specific to the gene of the present invention, and the chain length thereof may preferably be 5 to 100 nucleotides, more preferably 5 to 50 nucleotides, and still more preferably 10 to 20 nucleotides.

The suppression of gene expression may be performed using a single stranded nucleic acid molecule comprising all or a part of a nucleotide sequence identical with the sense chain of the gene of the present invention. Thus, this sense single stranded nucleic acid, similarly to the above antisense single stranded nucleic acid, can be used in suppressing the expression of the gene of the present invention. In this method, a single stranded RNA comprising all of a nucleotide sequence identical with the sense chain of the gene of the present invention can be used. Also, in the above method, a single stranded RNA comprising part of a nucleotide sequence identical with the sense chain of the gene of the present invention can be used. Such a partial single stranded RNA may be any RNA that can suppress the expression of the gene of the present invention. While it can be designed as appropriate by a person skilled in the art, it may preferably be specific to the gene of the present invention, and the chain length thereof may preferably be 5 to 100 nucleotides, more preferably 5 to 50 nucleotides, and still more preferably 10 to 20 nucleotides.

Furthermore, the suppression of gene expression may be performed using a double stranded nucleic acid molecule comprising all or a part of a nucleotide sequence identical with the gene of the present invention. For example, by using this double stranded nucleic acid molecule, an antisense or a sense single stranded nucleic acid of the present invention can be expressed in angiosperms. The double stranded nucleic acid molecule of the present invention may preferably be DNA, and its chain length and a specific nucleotide sequence should correspond to the chain length and the nucleotide sequence of the single stranded nucleic acid molecule of interest. For example, when the above antisense single stranded nucleic acid is to be expressed, the double stranded nucleic acid molecule of the present invention should contain the antisense chain of the gene of the present invention as a coding chain. Also, when the above sense single stranded nucleic acid is to be expressed, the double stranded nucleic acid molecule of the present invention should contain the sense chain of the gene of the present invention as a coding chain.

A double stranded nucleic acid molecule can be expressed in plants using a method known to a person skilled in the art. For example, by introducing an expression vector comprising a promoter, a double stranded nucleic acid molecule of the present invention, and a transcription terminator etc. into a plant of interest and cultivating the plant obtained, the double stranded nucleic acid molecule can be expressed. The introduction of an expression vector into a plant can be performed according to a method known to a person skilled in the art, such as an *Agrobacterium* method, a binary vector method, an electroporation method, a PEG method, a particle gun method and the like.

As other examples for suppressing gene expression using the nucleic acid molecule of the present invention, the cosuppression method can be mentioned. In this method, a sense double stranded DNA having the entire nucleotide sequence of the gene of the present invention may be introduced into a plant of interest. By so doing, a sense single stranded RNA of the present invention may be expressed, and thus the expression of this RNA may be extremely suppressed (Plant Cell 9: 1357-1368, 1997).

EXAMPLES

The present invention will now be explained specifically with reference to examples.

Example 1

Detection of an Activity of Transferring a Glycosyl to Hydroxyl Groups at the 4'-Position and 7-Position of a Flavone in *Nemophila* Petals Petals of *Nemophila menziessi* were collected at each development stage defined below, frozen in liquid nitrogen, and stored in a −80° C. freezer:
Stage 1: Uncolored, hard and folded buds (about 2-5 mm):
Stage 2: Colored, hard and folded buds (about 2-5 mm):
Stage 3: Colored and folded buds, and sepals are about to unfold (about 5-10 mm);
Stage 4: Buds of which petals are about to unfold (about 10-15 mm);
Stage 5: Completely unfolded flowers
<Preparation of *Nemophila* Petal Extract>
In petals at stages 1 and 2 before the biosynthesis of anthocyanin, the detection of the glycosyltransferase activity of a flavone can be expected. Thus, using petals at stages 1 and 2, petal extracts were prepared. 500 mg of petal samples (250 mg each of samples of stages 1 and 2 that had been stored at −80° C.) were mashed in a mortar while cooling in liquid nitrogen, and dissolved in 1.5 ml of an extraction buffer (composition: potassium phosphate buffer (pH 7.5): 100 mM, dithiothreitol (DTT); 1 mM, polyvinyl pyrrolidone 40; 50 mg/ml, sucrose; 10 mg/ml). The protein solution obtained was centrifuged (10,000 rpm, 4° C., 10 minutes), and to the supernatant collected, ammonium sulfate was added to a 30% saturation concentration. After stirring at 4° C. for 1 hour, it was centrifuged (10,000 rpm, 4° C., 10 minutes) to collect the supernatant. To the supernatant collected, ammonium sulfate was added to a 70% saturation concentration, which was then stirred at 4° C. for 1 hour, and then centrifuged (10,000 rpm, 4° C., 10 minutes) to collect the precipitate. The precipitate was dissolved in 500 µl of an elution buffer (composition: Tirs HCl (pH 7.5): 2.5 mM, DTT: 1 mM, amidinophenyl methanesulfonyl fluoride hydrochloride (APMSF): 10 µM), and column-purified using the NAP-5 Columns Sephadex G-25 DNA Grade (GE Healthcare) to remove ammonium sulfate. This solution was set as a "petal extract". For centrifugation, the Avanti HP-26 XP (rotor: JA-2) was used (BECKMAN COULTER).
<Determination of Enzyme Activity>
40 µl of the petal extract, 20 µl of 5 mM UDP-glucose, 20 µl of 1M Tris HCl (pH 7.5), and 1 µl of 500 ng/µl apigenin were mixed and prepared to 200 µl in water to obtain a reaction mixture, and the reaction mixture was maintained at 30° C. for 1 hour. Subsequently, 200 µl of a stopping buffer (a 90% acetonitrile aqueous solution containing 0.1% TFA) was added to stop the reaction, and the reaction mixture was analyzed with a high performance liquid chromatography (Prominence (Shimadzu)). The detector used is Shimadzu PDA SPD-M10AVP, and the flavone was detected at 330 nm. The column used is Shim-Pack ODS 150 mm×4.6 mm (Shimadzu). In elution, solution A (0.1% TFA aqueous solution) and solution B (a 90% acetonitrile aqueous solution containing 0.1% TFA) were used. A linear gradient from a 8:2 mixture of the two solutions to a 3:7 mixture over 10 minutes and then a 3:7 mixture over 5 minutes were used in elution. The flow rate was set at 0.6 ml/minute. As a control, a reaction mixture obtained by heat treating the petal extract and then subjecting it to an enzyme reaction under the same condition was used.

Figure 7:
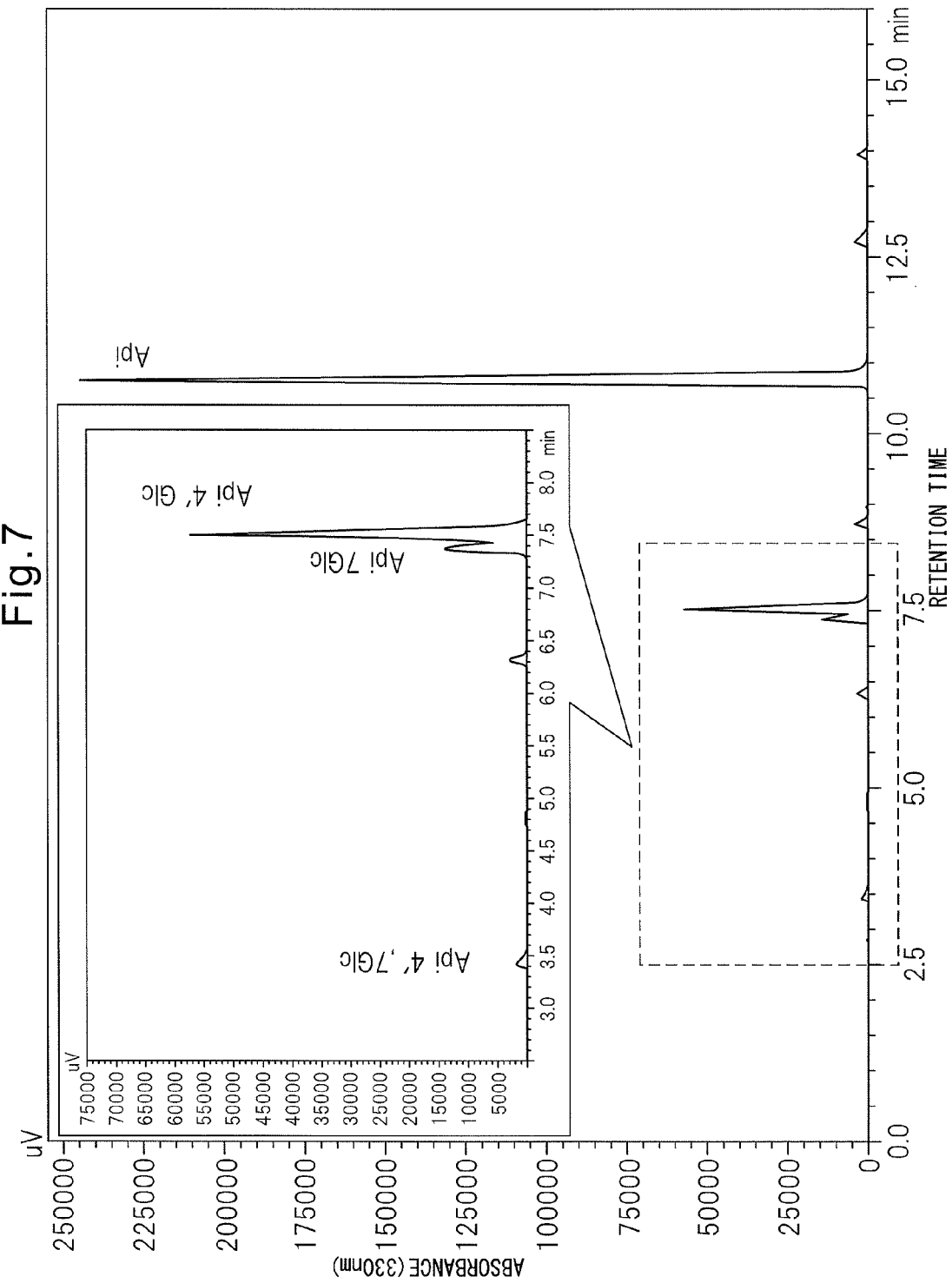

As a result, a flavone that exhibits the same retention time and the same absorption maximum as the purified apigenin 4',7-diglucoside product was biosynthesized (see FIG. 7). When UDP-glucose was not added in the enzyme reaction, none was biosynthesized. These results revealed the UDP-glucose-dependent presence of a protein having an activity of transferring a glycosyl to the hydroxyl groups of the 4'-position and 7-position of a flavone.

Example 2

Determination of the Retention Time and Absorption Maximum of Apigenin 4'-Glucoside In order to clarify the biosynthetic pathway of flavone 4',7-diglucoside, the retention time and absorption maximum of apigenin 4'-glucoside were determined.

Figure 8:
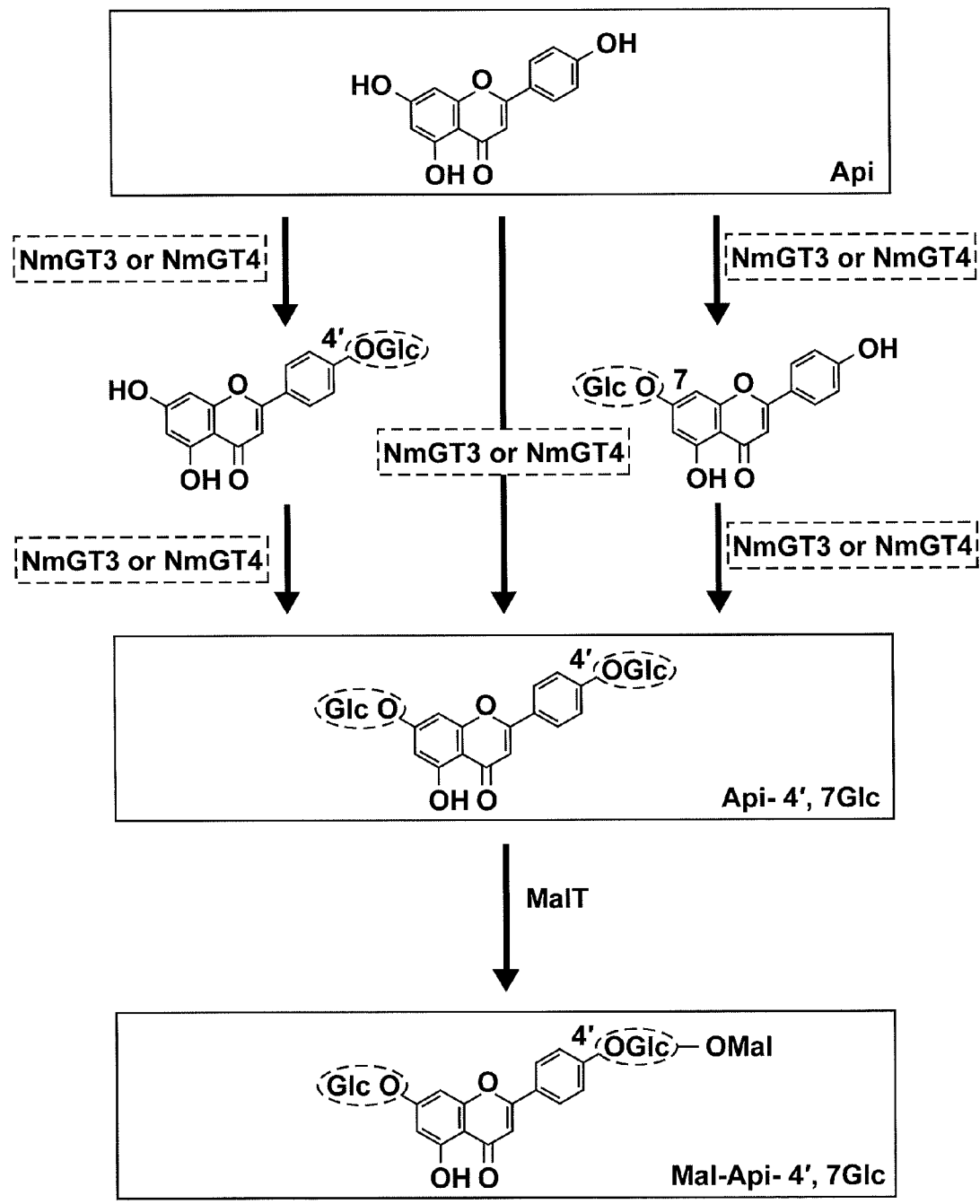

During the process of biosynthesis of apigenin 4',7-diglucoside in Example 1, apigenin 4'-glucoside and apigenin 7-glucoside should be biosynthesized as intermediate products (see FIG. 8). In the result of analysis of Example 1, the appearance of peaks of a product other than apigenin 7-glucoside and apigenin 4',7-diglucoside that are samples was expected.

As a result, a flavone exhibiting a retention time close to that of apigenin 7-glucoside was found to have been biosynthesized, which was judged to be apigenin 4'-glucoside (see FIG. 7). Thus the retention time and absorption maximum of apigenin 4'-glucoside was determined.

Example 3

Acquisition of Candidate Genes of a Gene Encoding a Protein Having an Activity of Transferring a Glycosyl to Both of the Hydroxyl Groups at the 4'- and 7-Positions of a Flavone <Isolation of Total RNA>

Using Plant RNAeasy Kit (QIAGEN), total RNA was isolated from the petals of stages 1 and 2 of *Nemophila* according to a protocol recommended by the manufacturer.

<Expression Analysis of cDNA Derived from *Nemophila* Petals>

After 30 μg of total RNA derived from *Nemophila* petals was subjected to a reverse transcription reaction, a uniform cDNA library was generated. The library generated was amplified clone by clone by an emulsion PCR, and then the base sequence was determined using the Genome Sequencer FLX (Roche Diagnostics Japan). The sequence data obtained were translated into amino acid sequences, and the sequences exhibiting homology with the amino acid sequence of anthocyanin 3'-glycosyltransferase of gentian were extracted. These sequences were assembled to obtain candidate genes encoding the glycosyltransferase.

Example 4

Preparation of Full-Length cDNA of Candidate Genes of a Gene Encoding a Protein Having an Activity of Transferring a Glycosyl to Both of the Hydroxyl Groups at the 4'- and 7-Positions of a Flavone In Example 3, 25 sequences of glycosyltransferase were obtained. Ten genes (NmGT0 through NmGT9) among them were subjected to experiments for obtaining full-length cDNA sequences.

A full-length cDNA sequence was obtained using a cDNA amplification kit, the GeneRacer Kit® (Invitrogen), according to a protocol recommended by the manufacturer. From among the cDNA partial sequences obtained in Example 3, regions specific to the clones were selected, and based on the sequences of the regions RACE primers were designed to obtain 5',3' end sequences by RACE PCR. Based on the sequences, primers for amplifying the full-length cDNA sequences were designed, and a PCR reaction was performed on 50 IA with *Nemophila* cDNA as the template using the KOD-plus polymerase (TOYOBO) according to a protocol recommended by the manufacturer (94° C. is maintained for 2 minutes, and a cycle comprising 94° C. for 15 seconds, 55° C. for 30 seconds and 68° C. for 2 minutes was repeated for 30 cycles, and then maintained at 4° C.). *Nemophila* cDNA was synthesized using a reverse transcriptase, the SuperScript II® Reverse Transcriptase (Invitrogen), with the total RNA isolated in Example 2 as the template according to a protocol recommended by the manufacturer. The primers were designed so that restriction sites can be included on both ends of the full-length cDNA in order to insert the NmGT0 through NmGT9 genes into an *Escherichia coli* expression vector pET15b (Novagen). Using the PCR product, plasmids (pTOPO-NmGT0 through pTOPONmGT9) containing the full-length NmGT gene were obtained using a one-step cloning kit, the Zero Blunt® TOPO® PCR Cloning kit for sequencing (Invitrogen), according to a protocol recommended by the manufacturer. By analyzing the base sequences inserted into the plasmids, the full-length cDNA sequences of the candidate genes (NmGT0 through NmGT9) encoding a protein having an activity of transferring a glycosyl to both of the hydroxyl groups at the 4'-position and 7-position of a flavone were obtained (NmGT3: SEQ ID NO: 1, NmGT4: SEQ ID NO: 3).

Example 5

Experiment of Determining the Enzyme Activity of Candidate Proteins Having an Activity of Transferring a Glycosyl to Both of the Hydroxyl Groups at the 4'-Position and 7-Position of a Flavone (when Crude Enzyme was Used)

<Creation of an *Escherichia coli* Expression Construct>

3 μg each of pTOPO-NmGT0 through pTOPO-NmGT9 was treated with the corresponding restriction enzymes, and about 1.5 kb DNA fragments obtained were collected. 2 μg of the vector pET15b was also treated with the restriction enzymes, and was ligated to the DNA fragments obtained to create *Escherichia coli* expression constructs (pET-NmGT0 through pET-NmGT9).

<Expression of Glycosyltransferase in *Escherichia coli*> pET-NmGT0 through pET-NmGT9 were introduced into *Escherichia coli* strain BL2 using the One Shot BL21 (DE3) (Invitrogen) according to a protocol recommended by the manufacturer to obtain transformed *Escherichia coli*. The *Escherichia coli* was cultured, using the Overnight Express Autoinduction System 1 (Novagen) according to a protocol recommended by the manufacturer. With 2 ml of the culture liquid prepared, the transformed *Escherichia coli* was cultured at 37° C. (about 4 hours) until the OD600 value reached 0.5. To this *Escherichia coli* solution as the preculture, 50 ml of the culture liquid was added and then subjected to the main culture overnight at 27° C.

The overnight-cultured *Escherichia coli* solution was centrifuged (3000 rpm, 4° C., 15 minutes), and the cells collected were suspended in 5 ml of a sonic buffer (composition: Tris HCl (pH 7.0): 2.5 mM, dithiothreitol (DTT): 1 mM, amidinophenyl methanesulfonyl fluoride hydrochloride (APMSF): 10 μM), and *Escherichia coli* was disrupted by sonication. The cells were then centrifuged (1500 rpm, 4° C., 10 minutes), and the supernatant was collected. The supernatant was used as a crude enzyme solution. For centrifugation, the Avanti HP-26 XP (rotor: JA-2) was used (BECKMAN COULTER).

<Determination of Enzyme Activity>

80 μl of the crude enzyme solution, 20 μl of 5 mM UDP-glucose, 20 μl of 1M Tris HCl (pH 7.5), and 1 μl of 500 ng/μl apigenin were prepared on ice to 200 μl in water, and the reaction mixture obtained was maintained at 30° C. for 1 hour. Subsequently, 200 μl of the stopping buffer (a 90% acetonitrile aqueous solution containing 0.1% TFA) was added to stop the reaction, and analyzed with a high performance liquid chromatography (Prominence (Shimadzu)). The detector used is Shimadzu PDA SPD-M10AVP, and the flavone was detected at 330 nm. The column used is Shim-Pack ODS 150 mm×4.6 mm (Shimadzu). In elution, solution A (a 0.1% TFA aqueous solution) and solution B (a 90% acetonitrile aqueous solution containing 0.1% TFA) were used. A linear gradient from a 8:2 mixture of the two solutions to a 3:7 mixture over 10 minutes and then a 3:7 mixture over 5 minutes were used in elution. The flow rate was set at 0.6 ml/minute. As a control, the crude enzyme solution of *Escherichia coli* in which no insert-inserted pET vector was introduced and was subjected to an enzyme reaction under the same condition was used.

As a result, peaks other than that of the substrate were observed for NmGT3 and NmGT4. NmGT3 and NmGT4 were contained in the 7,3' GT cluster.

Examples 6 to 10 below will describe NmGT3 and NmGT4 (SEQ ID NO: 1 and 3, respectively).

Example 6

Experiment of Determining the Enzyme Activity of a Protein Having an Activity of Transferring a Glycosyl to Both of the Hydroxyl Groups at the 4'-Position and 7-Position of a Flavone (when the His-Tag-Added Protein was Purified)

<Expression of Glycosyltransferase in *Escherichia coli* and Protein Purification>

The *Escherichia coli* strain BL2 in which pET-NmGT3 or pET-NmGT4 described in Example 5 was introduced was cultured, using the Overnight Express Autoinduction System 1 (Novagen) according to a protocol recommended by the manufacturer. With 8 ml of the culture liquid prepared, the transformed *Escherichia coli* was cultured at 37° C. (about 4 hours) until the OD600 value reached 0.5. To this *Escherichia coli* solution as the preculture, 200 ml of the culture liquid was added and then subjected to the main culture overnight at 25° C.

The overnight-cultured *Escherichia coli* solution was centrifuged (1000×g, 4° C., 10 minutes), and the cells collected were suspended in 20 ml of a buffer (composition: NaCl: 0.5 M, Tris HCl (pH 7.9): 20 mM, imidazole: 5 mM, amidinophenyl methanesulfonyl fluoride hydrochloride (APMSF): 10 μM), and *Escherichia coli* was disrupted by sonication. The cells were then centrifuged (1400×g, 4° C., 20 minutes), and the supernatant was collected. The supernatant was passed through a 0.45 μm filter to His-Tag-purify using the Profinia (Bio-Rad) according to a protocol recommended by the manufacturer. The purified protein solution thus obtained was centrifuged (7500×g, 4° C., 15 minutes) using the Centrifugal filters (Ultracel-10K) (Amicon Ultra), and the concentrated protein solution was termed as "NmGT3 protein solution" and "NmGT4 protein solution". For centrifugation, the Avanti HP-26 XP (rotor: JA-2) was used (BECKMAN COULTER).

<Determination of Enzyme Activity>

20 μl of the protein solution, 20 μl of 5 mM UDP-glucose, 20 μl of 1M Tris HCl (pH 7.5), and 1 μl of 500 ng/μl apigenin were mixed and prepared on ice to 200 μl in water, and the reaction mixture obtained was maintained at 30° C. for 20 minutes. Subsequently, 200 μl of the stopping buffer (a 90% acetonitrile aqueous solution containing 0.1% TFA) was added to stop the reaction, and analyzed with a high performance liquid chromatography (Prominence (Shimadzu)). The detector used is Shimadzu PDA SPD-M10AVP, and the flavone was detected at 330 nm. The column used is Shim-Pack ODS 150 mm×4.6 mm (Shimadzu). In elution, solution A (a 0.1% TFA aqueous solution) and solution B (a 90% methanol aqueous solution containing 0.1% TFA) were used. A linear gradient from a 8:2 mixture of the two solutions to a 3:7 mixture over 10 minutes and then a 3:7 mixture over 6 minutes were used in elution. The flow rate was set at 0.6 ml/minute.

Figure 9:
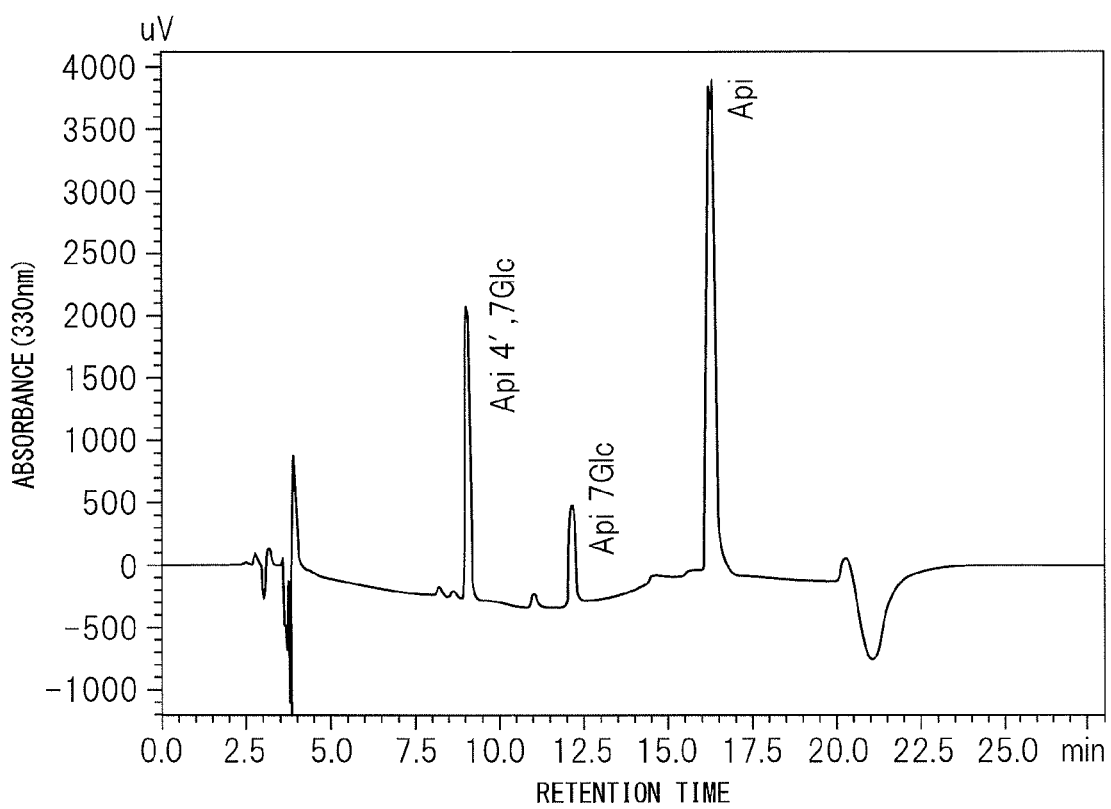
Figure 10:
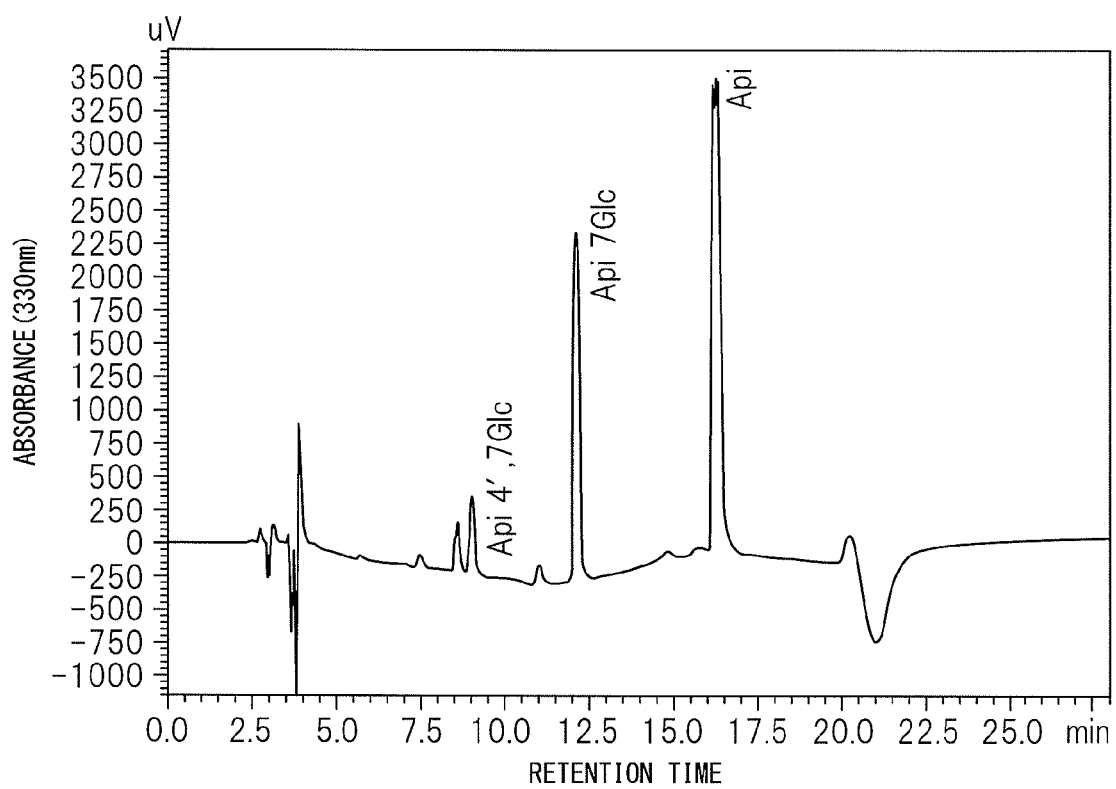
Figure 11:
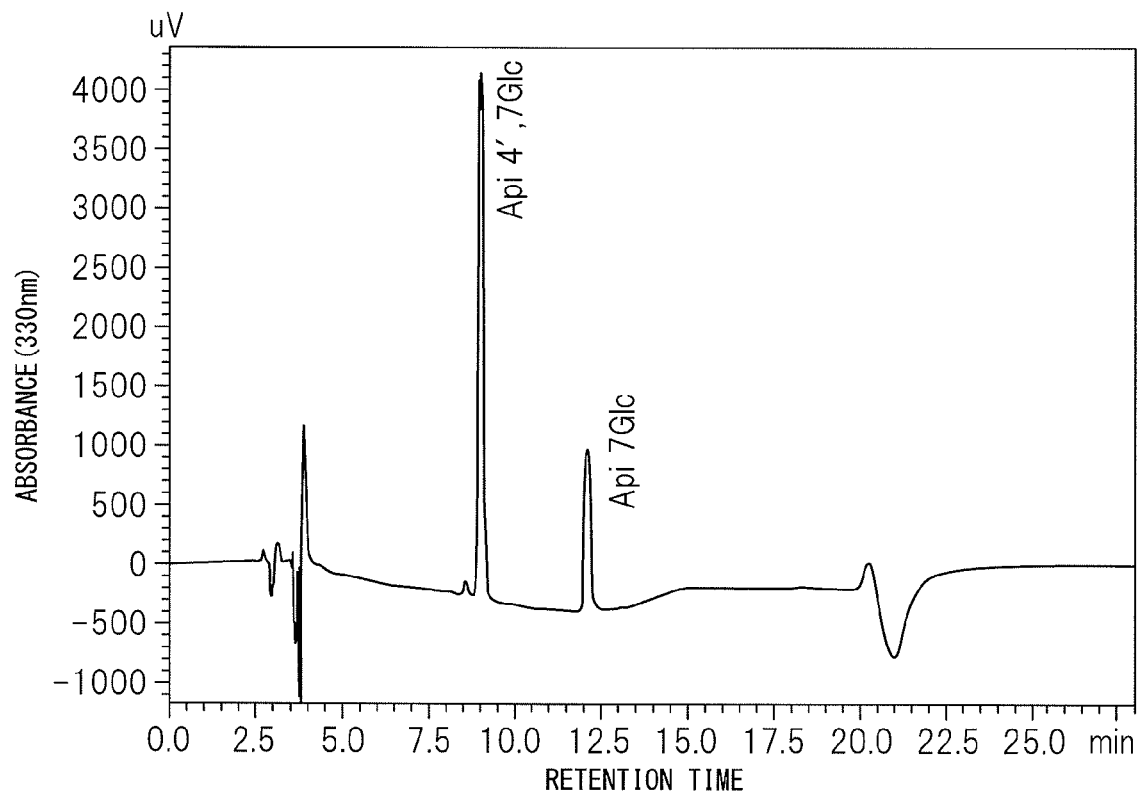
Figure 12:
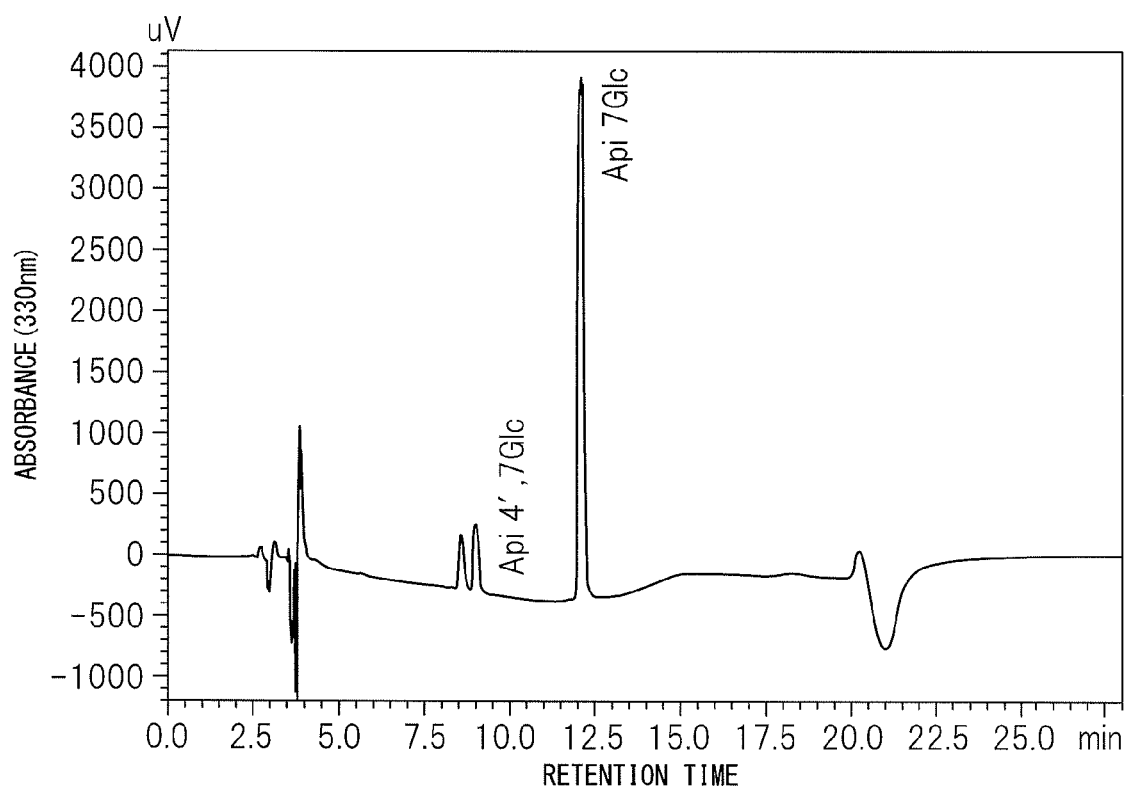

As a result, a flavone exhibiting the same retention time and the same absorption maximum as the purified apigenin 4',7-diglucoside product had been biosynthesized (see FIGS. 9 and 10). Even if the substrate was replaced with 50 ng/μl apigenin 7-glucoside and subjected to an enzyme reaction under the same condition, a flavone exhibiting the same retention time and the same absorption maximum as the purified apigenin 4',7-diglucoside product was biosynthesized (see FIGS. 11 and 12). Furthermore, even if the substrate was replaced with apigenin 4'-glucoside and subjected to an enzyme reaction under the same condition, a flavone exhibiting the same retention time and the same absorption maximum as the apigenin 4',7-diglucoside purified product was biosynthesized (not shown). These results demonstrated that the NmGT3 protein solution and the NmGT4 protein solution are proteins having an activity of transferring a glycosyl to both of the hydroxyl groups at the 4'-position and 7-position of a flavone capable of biosynthesizing apigenin 4',7-diglucoside using apigenin, apigenin 4'-glucoside or apigenin 7-glucoside as the substrate. Furthermore, when the reactivity to various flavonoid compounds and betanidine was examined, as shown in FIG. 13, the NmGT3 and NmGT4 proteins were found to have an activity for not only apigenin and its glycosides but for luteolin and its glycosides and flavonol and its glycosides, and to glycosylate them.

The glycosyltransferase gene (Dbs5GT; betanidin 5GT) derived from Livingstone daisy originally transfers glucose to a hydroxyl group at the 5-position of betanidine, but it is reported that it has an in vitro activity of transferring glucose to either one of the hydroxyl groups at the 4'-position or 7-position of a flavonoid. It was revealed that this glycosyltransferase gene derived from Livingstone daisy has a great different reactivity from the NmGT3 and 4 proteins and flavonoid compounds and betanidine (see FIG. 13).

The identity and the homology of the amino acid sequences (SEQ ID NO: 2 and 4, respectively) of NmGT3 and NmGT4 were 31% and 47% (see FIG. 14). In this analysis, the Clustal W program of the MacVector application (version 9.5, Oxford Molecular Ltd., Oxford, England) was used. The identity of NmGT3 and NmGT4 on the nucleic acid level was 51%.

Among the glycosyltransferases already identified, the amino acid sequence having the highest identity with NmGT3 was an enzyme (GenBank Accession No. BAD52006) that adds a glycosyl to the 2'-position of chalcononaringenin of carnation. The identity of NmGT3 and an enzyme that adds a glycosyl to the 2'-position of chalcononaringenin of carnation was 32% (see FIG. 15). The identity of NmGT3 and an enzyme that adds a glycosyl to the 2'-position of chalcononaringenin of carnation on the nucleic acid level was 47%.

Among the glycosyltransferases already identified, the amino acid sequence having the highest identity with NmGT4 was an enzyme (described in Non-patent document 9) that adds a glycosyl to the 7-position of a flavonoid of *Scutellaria baicalensis*. The identity of NmGT4 and an enzyme that adds a glycosyl to the 7-position of a flavonoid of *Scutellaria baicalensis* was 52% (see FIG. 16). The identity of NmGT4 and an enzyme that adds a glycosyl to the 7-position of a flavonoid of *Scutellaria baicalensis* on the nucleic acid level was 60%.

Example 7

Expression of a Gene Encoding a Protein Having an Activity of Transferring a Glycosyl to Both of the Hydroxyl Groups at the 4'- and 7-Positions of a Flavone in *Torenia*

In order to confirm whether or not the NmGT3 gene and the NmGT4 gene translate a protein having an activity of transferring a glycosyl to both of the hydroxyl groups at the 4'- and 7-positions of a flavone in plants, binary vectors pSPB4584 through 4587 for expressing NmGT3 and NmGT4 were constructed, and introduced into *torenia* (Summer Wave). Details of the constructs introduced are shown below (see FIG. 17).
<Preparation of Constructs> pSPB4584 has the basic skeleton of a binary vector pBIN-PLUS (vanEngel et al., Transgenic Research 4, p 288) for introduction into plants, and comprises the E1235S promoter (Mitsuhara et al., (1996) Plant Cell Physiol. 37, p 49) having two repeats of an enhancer sequence upstream to the cauliflower mosaic virus 35S promoter, the full-length cDNA NmGT3, and the mas terminator.

pSPB4585 has the basic skeleton of pBINPLUS, and comprises the E1235S promoter, the full-length cDNA NmGT4, and the mas terminator.

pSPB4586 has the basic skeleton of pBINPLUS, and comprises two expression cassettes (1. the E1235S promoter, the full-length cDNA NmGT8, and the mas terminator, 2. the E1235S promoter, the full-length cDNA NmGT3, and the mas terminator).

pSPB4587 has the basic skeleton of pBINPLUS, and comprises two expression cassettes (1. the E1235S promoter, the full-length cDNA NmGT8, and the mas terminator, 2. the E1235S promoter, the full-length cDNA NmGT4, and the mas terminator).
<Tissue-Specific Expression Analysis>

In a selective medium containing kanamycin, shoots were formed, and plants in which rooting was noted were acclaimed. Using petals of buds that are not calyx-splitting of each transformant, gene expression analysis was performed. Total RNA was isolated in a method similar to that described in Example 3, and cDNA was synthesized in a method similar to that described in Example 4. The reverse transcription PCR reaction was performed with cDNA as the template using the ExTaq polymerase (Takara) according to a protocol recommended by the manufacturer on 30 μl (94° C. is maintained for 2 minutes, and a cycle comprising 94° C. for 1 minute, 55° C. for 1 minute and 72° C. for 2 minutes was repeated for 25 cycles, and then maintained at 4° C.). Primers were designed so that each full-length cDNA can be specifically amplified. As a result, the transcription of NmGT3 and NmGT4 in *torenia* was confirmed.

Example 8

Expression of a Gene Encoding a Protein Having an Activity of Transferring a Glycosyl to Both of the Hydroxyl Groups at the 4'- and 7-Positions of a Flavone in *Petunia*

Figure 18:
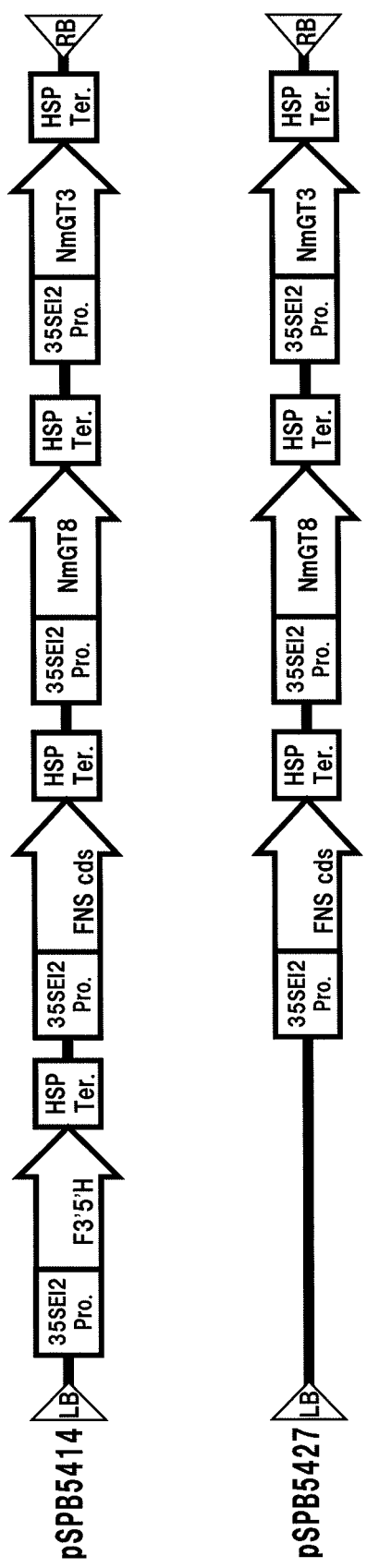

Binary vectors pSPB5414 and 5427 for expressing NmGT3 were constructed, and introduced into *petunia* (Surfinia bouquet red). Details of the constructs introduced are shown below (see FIG. 18).
<Preparation of Constructs> pSPB5414 has the basic skeleton of pBINPLUS, and comprises four expression cassettes (1. the E1235S promoter, the full-length cDNA pansy F3'5'H (described in PCT/JP2004/011958, see SEQ ID NO: 5) and a heat shock protein terminator (HSP terminator) that is very useful in the expression of foreign genes in plants (Plant Cell Physiol (2010) 51, 328-332), 2. the E1235S promoter, the full-length cDNA *torenia* flavone synthase (described in PCT/JP2008/061600, see SEQ ID NO: 7) and the HSP terminator, 3. the E1235S promoter, the full-length cDNA NmGT8 and the HSP terminator, 4. the E1235S promoter, the full-length cDNA NmGT3 and the HSP terminator).

pSPB5427 has the basic skeleton of pBINPLUS, and comprises three expression cassettes (1. the E1235S promoter, the full-length cDNA *torenia* flavone synthase and the HSP terminator, 2. the E1235S promoter, the full-length cDNA NmGT8 and the HSP terminator, 3. the E1235S promoter, the full-length cDNA NmGT3 and the HSP terminator).
<Tissue-Specific Expression Analysis>

In a selective medium containing kanamycin, shoots were formed, and plants in which rooting was noted were acclaimed. Using leaves of each transformant, gene expression analysis was performed in a manner similar to that described in Example 7. The result confirmed the transcription of NmGT3 and NmGT4 in *petunia*.

Example 9

Figure 19:
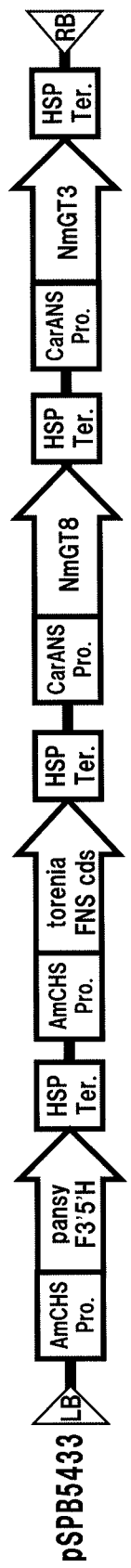

Expression of a Gene Encoding a Protein Having an Activity of Transferring a Glycosyl to Both of the Hydroxyl Groups at the 4'- and 7-Positions of a Flavone in Carnation A binary vector pSPB5433 for expressing NmGT3 was constructed, and introduced into carnation (Cream Cinderella). Details of the construct introduced are shown below (see FIG. 19).

pSPB5433 has the basic skeleton of pWTT2132 (DNA Plant Technologies, USA=DNAP), a binary vector for introduction into plants, and comprises four expression cassettes (1. the chalcone synthase promoter of *Antirrhinum majus* (described in PCT/AU94/00265), the full-length cDNA pansy F3'5'H and the HSP terminator, 2. the chalcone synthase promoter of *Antirrhinum majus*, the full-length cDNA *torenia* flavone synthase and the HSP terminator, 3. carnation anthocyanin synthase promoter (described in PCT/AU/2009/001659), the full-length cDNA NmGT8 and the HSP terminator, 4. carnation anthocyanin synthase promoter, the full-length cDNA NmGT3 and the HSP terminator).

Example 10

Figure 20:
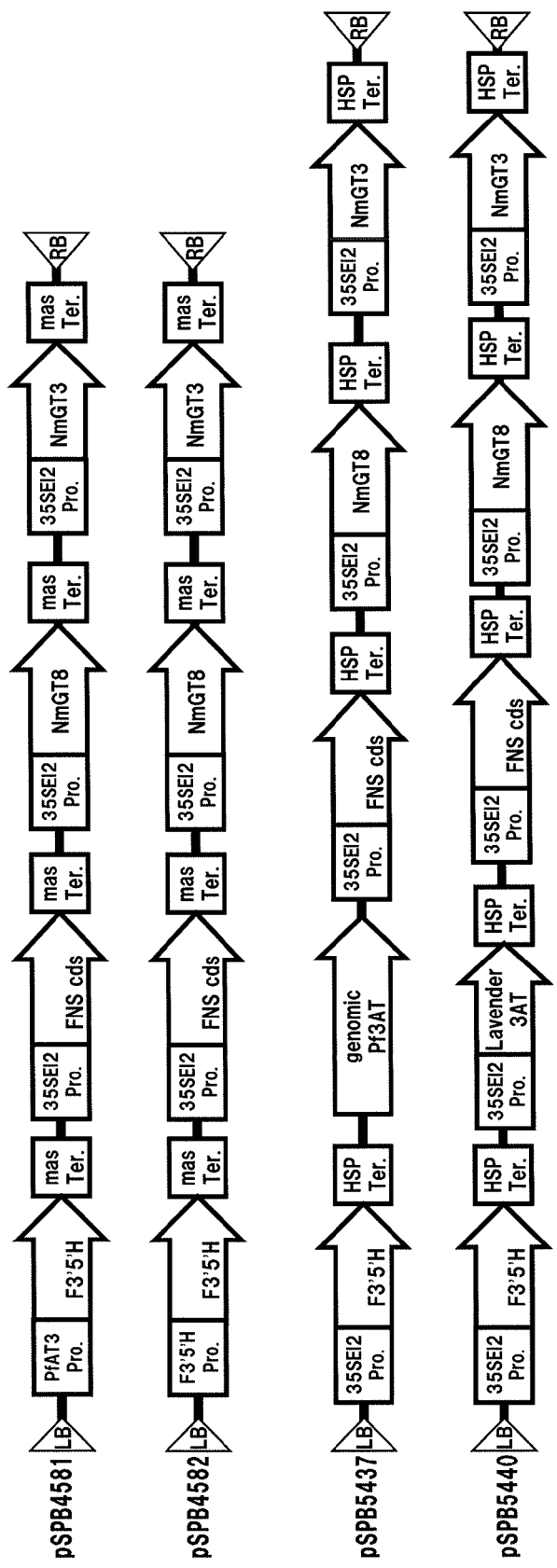

Expression of a Gene Encoding a Protein Having an Activity of Transferring a Glycosyl to Both of the Hydroxyl Groups at the 4'- and 7-Positions of a Flavone in Rose Binary vectors pSPB4581, 4582, 5437 and 5440 for expressing NmGT3 were constructed, and introduced into Rose (Noblesse, Ritapahyumera). Details of the constructs introduced are shown below (see FIG. 20).

pSPB4581 has the basic skeleton of pBINPLUS, and comprises four expression cassettes (1. the *perilla* anthocyanin 3-acyl transferase promoter (described in PCT/JP2010/053909), the full-length cDNA pansy F3'5'H and the mas terminator, 2. the E1235S promoter, the full-length cDNA *torenia* flavone synthase and the mas terminator, 3. the E1235S promoter, the full-length cDNA NmGT8 and the mas terminator, 4. the E1235S promoter, the full-length cDNA NmGT3 and the mas terminator).

pSPB4582 has the basic skeleton of pBINPLUS, and comprises four expression cassettes (1. the pansy F3'5'H promoter (described in PCT/JP2010/053909), the full-length cDNA pansy F3'5'H and the mas terminator, 2. the E1235S promoter, the full-length cDNA *torenia* flavone synthase and the mas terminator, 3. the E1235S promoter, the full-length cDNA NmGT8 and the mas terminator, 4. the E1235S promoter, the full-length cDNA NmGT3 and the mas terminator).

pSPB5437 has the basic skeleton of pBINPLUS, and comprises five expression cassettes (1. the E1235S promoter, the full-length cDNA pansy F3'5'H and the HSP terminator, 2. the *perilla* anthocyanin 3-acyl transferase promoter chromosome gene (described in PCT/JP2010/053909, see SEQ ID NO: 9), 3. the E1235S promoter and the full-length cDNA *torenia* flavone synthase and the HSP terminator, 4. the E1235S promoter, the full-length cDNA NmGT8 and the HSP terminator, 5. E1235S promoter and the full-length cDNA NmGT3 and the HSP terminator).

pSPB5440 has the basic skeleton of pBINPLUS, and comprises five expression cassettes (1. the E1235S promoter, the full-length cDNA pansy F3'5'H and the HSP terminator, 2. the E1235S promoter, cDNA lavender anthocyanin 3-acyl transferase (described in PCT/JP/1996/000348, see SEQ ID NO: 10) and the HSP terminator, 3. the E1235S promoter, the full-length cDNA *torenia* flavone synthase and the HSP terminator, 4. the E1235S promoter, the full-length cDNA NmGT8 and the HSP terminator, 5. the E1235S promoter, the full-length cDNA NmGT3 and the HSP terminator).

Example 11

Acquisition of Candidate Genes of a Gene Encoding a Protein Having an Activity of Transferring a Glycosyl to Both of the Hydroxyl Groups at the 4'- and 7-Positions of a Flavone Derived from *Salvia uliginosa*

Figure 6:
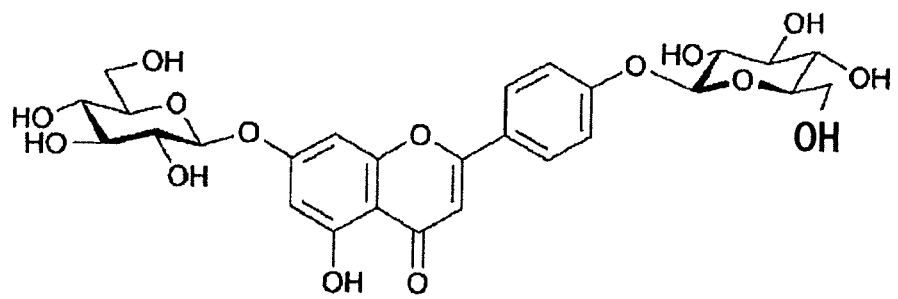
FIG. 6

Petals of *Salvia uliginosa* contains apigenin 4',7-diglucoside (see FIG. 6) as a major flavone. Thus, *Salvia uliginosa* is expected to have a gene encoding a protein having an activity of transferring a glycosyl to both of the hydroxyl groups at the 4'- and 7-positions of a flavone. Thus, petals were obtained from buds of *Salvia uliginosa*, and a cDNA library was generated in a manner similar to that described in PCT/JP2003/010500, and screened for candidate genes of a gene encoding a protein having an activity of transferring a glycosyl to both of the hydroxyl groups at the 4'- and 7-positions of a flavone. After the base sequences of 24 positive clones were determined, three different cDNA sequences (SuGT2, 5, 10) contained in the 7, 3' GT cluster were obtained. For these genes, in a manner similar to that described in Example 4, plasmids (pTOPO-SuGT2, 5, 10) containing cDNA full-length were constructed. The base sequences inserted into the plasmids were analyzed, and the full-length cDNA sequence of the candidate genes (SuGT2, 5, 10) of a gene encoding a protein having an activity of transferring a glycosyl to both of the hydroxyl groups at the 4'- and 7-positions of a flavone derived from *Salvia uliginosa* were obtained (SuGT5, see SEQ ID NO: 12).

SEQ ID NO: 12

Experiment of Determining the Enzyme Activity of Protein Candidates Having an Activity of Transferring a Glycosyl to Both of the Hydroxyl Groups at the 4'-Position and 7-Position of a Flavone Derived from *Salvia uliginosa* (when the His-Tag-Added Protein was Purified)

<Preparation of an *Escherichia coli* Expression Construct>
*Escherichia coli* expression constructs (pET-SuGT2, 5, 10) were created in a manner similar to that described in Example 5.

<Expression of Glycosyltransferase in *Escherichia coli* and Protein Purification>

In a manner similar to that described in Example 5, "SuGT2 protein solution", "SuGT5 protein solution" and "SuGT10 protein solution" were prepared.

<Determination of Enzyme Activity>

20 µl of the protein solution, 20 µl of 5 mM UDP-glucose, 20 µl of 1M Tris HCl (pH 7.5), and 1 µl of 500 ng/µg apigenin were mixed and prepared on ice to 200 µl in water, and the reaction mixture obtained was maintained at 30° C. for 90 minutes. Subsequently, 200 µl of the stopping buffer (a 90% acetonitrile aqueous solution containing 0.1% TFA) was added to stop the reaction, and analyzed with a high performance liquid chromatography (Prominence (Shimadzu)). The detector used is Shimadzu PDA SPD-M10AVP, and the flavone was detected at 330 nm. The column used is Shim-Pack ODS 150 mm×4.6 mm (Shimadzu). In elution, solution A (a 0.1% TFA aqueous solution) and solution B (a 90% methanol aqueous solution containing 0.1% TFA) were used. A linear gradient from a 8:2 mixture of the two solutions to a 3:7 mixture over 10 minutes and then a 3:7 mixture over 6 minutes were used in elution. The flow rate was set at 0.6 ml/minute.

Figure 21:
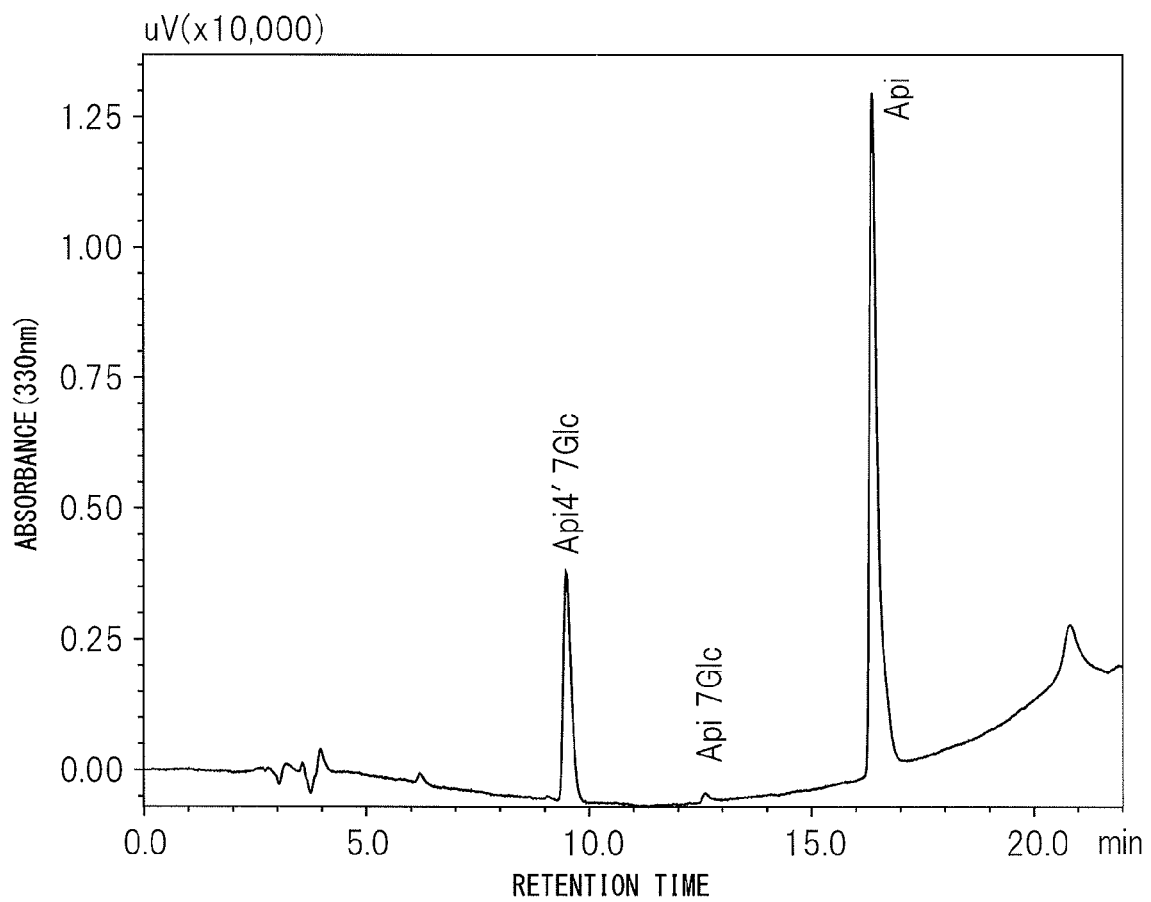
Figure 22:
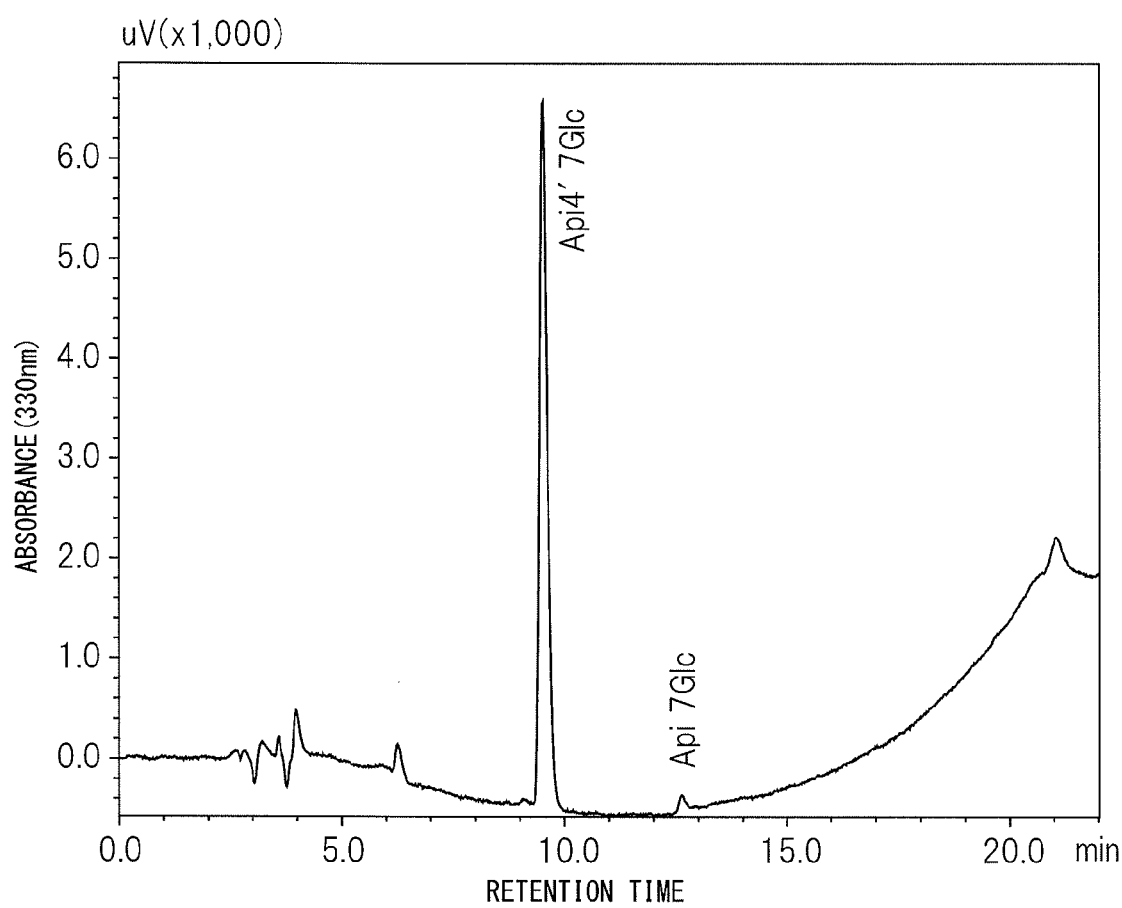

As a result, when the SuGT5 protein solution was used, a flavone exhibiting the same retention time and the same absorption maximum as the purified apigenin 4',7-diglucoside product had been biosynthesized (see FIG. 21). Even if the substrate was replaced with 500 ng/µg apigenin 7-glucoside and subjected to an enzyme reaction under the same condition, a flavone exhibiting the same retention time and the same absorption maximum as the purified apigenin 4',7-diglucoside product was biosynthesized (see FIG. 22). These results demonstrated that the SuGT5 protein solution is a protein having an activity of transferring a glycosyl to both of the hydroxyl groups at the 4'-position and 7-position of a flavone capable of biosynthesizing apigenin 4',7-diglucoside using apigenin or apigenin 7-glucoside as the substrate.

Similarly to the above-mentioned NmGT3 and NmGT4 proteins, SuGT5 was found to have an activity for not only apigenin and its glycosides but for luteolin and its glycosides and flavonol and its glycosides, and to glycosylate them. On the other hand, its reactivity for flavonoid compounds and betanidine was greatly different from that of the glycosyltransferase derived from Livingstone daisy (see FIG. 13).

The identity and homology of the amino acid sequences (SEQ ID NO: 2 and 6, respectively) of SuGT5 and NmGT3 were 38% and 47% (see FIG. 23). In this analysis, the Clustal W program of the MacVector application (version 9.5, Oxford Molecular Ltd., Oxford, England) was used. The identity of SuGT5 and NmGT3 on the nucleic acid level was 47%.

The amino acid sequences (SEQ ID NO: 4 and 6, respectively) of SuGT5 and NmGT4 had an identity of were 51% and a homology of 66% (see FIG. 24). The identity of SuGT5 and NmGT4 on the nucleic acid level was 58%.

INDUSTRIAL APPLICABILITY

In accordance with the present invention, a polynucleotide encoding a protein having an activity of transferring a glycosyl to both of the hydroxyl groups at the 4'-position and 7-position of a flavone was identified for the first time. By expressing the polynucleotide of the present invention in a suitable host cell, a protein having an activity of transferring a glycosyl to both of the hydroxyl groups at the 4'-position and 7-position of a flavone can be produced. In accordance with the present invention, a protein having an activity of specifically transferring a glycosyl to both of the hydroxyl groups at the 4'- and 7-positions of a flavone can be used in altering flower color by expressing it in a constitutive and tissue-specific manner in a plant. Also, in accordance with the present invention, there are provided a method for producing a flavone in which a glycosyl has been added to both of the hydroxyl groups at 4'- and 7-positions thereof, and food products, pharmaceutical products, and cosmetic products obtained by this production method.

The invention claimed is:

1. A polynucleotide selected from the group consisting of:
   (a) a polynucleotide comprising SEQ ID NO: 1; and
   (b) a polynucleotide which encodes a protein comprising an amino acid sequence in which one to five amino acids have been deleted, substituted, inserted, and/or added in the amino acid sequence defined in SEQ ID NO: 2 and having an activity of transferring a glycosyl to both of the hydroxyl groups at 4'- and 7-positions of a flavone.

2. A vector comprising the polynucleotide according to claim 1.

3. A plant or a progeny thereof, or a part or tissue thereof, each containing the polynucleotide according to claim 2.

4. The part of a plant according to claim 3, which is a cut flower.

5. A cut flower artifact comprising the polynucleotide of SEQ ID NO: 1, produced from the cut flower according to claim 4.

* * * * *